US012605353B2

(12) United States Patent
Yang et al.

(10) Patent No.: US 12,605,353 B2
(45) Date of Patent: Apr. 21, 2026

(54) PDIA4 INHIBITORS AND USE THEREOF FOR INHIBITING β-CELL PATHOGENESIS AND TREATING DIABETES

(71) Applicant: Academia Sinica, Taipei City (TW)

(72) Inventors: Wen-Chin Yang, Taichung County (TW); Keng-Chang Tsai, Taipei City (TW)

(73) Assignee: ACADEMIA SINICA, Taipei City (TW)

( * ) Notice: Subject to any disclaimer, the term of this patent is extended or adjusted under 35 U.S.C. 154(b) by 925 days.

(21) Appl. No.: 17/780,482

(22) PCT Filed: Nov. 15, 2020

(86) PCT No.: PCT/US2020/060639

§ 371 (c)(1),
(2) Date: May 26, 2022

(87) PCT Pub. No.: WO2021/113062

PCT Pub. Date: Jun. 10, 2021

(65) Prior Publication Data

US 2023/0046445 A1 Feb. 16, 2023

Related U.S. Application Data

(60) Provisional application No. 62/942,314, filed on Dec. 2, 2019.

(51) Int. Cl.

| | |
|---|---|
| ***A61K 31/216*** | (2006.01) |
| ***A61K 31/196*** | (2006.01) |
| ***A61P 3/10*** | (2006.01) |

(52) U.S. Cl.
CPC .......... *A61K 31/216* (2013.01); *A61K 31/196* (2013.01); *A61P 3/10* (2018.01)

(58) Field of Classification Search
CPC .. A61K 31/216; A61K 31/196; A61K 31/155; A61K 31/4035; A61K 31/695; A61P 3/10
See application file for complete search history.

(56) References Cited

U.S. PATENT DOCUMENTS

| | | | |
|---|---|---|---|
| 3,763,163 | A | 10/1973 | Hardtmann |
| 2008/0319194 | A1 | 12/2008 | Jacobi et al. |
| 2015/0223451 | A1 | 8/2015 | Mousa et al. |
| 2019/0119664 | A1 | 4/2019 | Inui et al. |

FOREIGN PATENT DOCUMENTS

| | | | |
|---|---|---|---|
| CN | 104725327 | A | 6/2015 |
| CN | 105001168 | A1 | 10/2015 |
| WO | 2004046101 | A2 | 6/2004 |
| WO | 2012066578 | A2 | 5/2012 |
| WO | 2013021363 | A1 | 2/2013 |
| WO | 2015066482 | A1 | 5/2015 |
| WO | 2019170543 | A1 | 9/2019 |

OTHER PUBLICATIONS

International Search Report for PCT/US2020/060639, dated Mar. 18, 2021.
Written Opinion of International Search Authority for PCT/US2020/060639, dated Mar. 18, 2021.
Sebastien March et al. "Expedient synthesis of substituted 4-hydroxy-quinolin-2(1H)-ones" Tetrahedron Letters 56 (2015) 5859-5863.
Yang Li et al "Thioxo-dihydroquinazolin-one Compounds as Novel Inhibitors of Myeloperoxidase" ACS Med Chem Lett. Aug. 31, 2015;6(10):1047-1052.
Overmyer, C. J., "A synthesis of substitution derivatives of indigo II. Ethyl nitrotrimethylgallyl acetate and related compounds", Journal of the American Chemical Society, 1927, 49, 499-509.
Helal, C. J. et al, "Use of Structure-Based Design to Discover a Potent, Selective, In Vivo Active Phosphodiesterase 10A Inhibitor Lead Series for the Treatment of Schizophrenia", Journal of Medicinal Chemistry, 2011, 54(13), 4536-47.

*Primary Examiner* — Kevin E Weddington
(74) *Attorney, Agent, or Firm* — Hsiu-Ming Saunders; INTELLECTUAL PROPERTY CONNECTIONS, INC.

(57) ABSTRACT

Disulfide-Isomerase A4 (PDIA4) inhibitors and use thereof for inhibiting pancreatic β-cell pathogenesis and treating diabetes are disclosed. Drug candidates that inhibit PDIA4 with IC50 values ranging from 4 μM to 300 nM are identified. The compounds are highly active in augmenting insulin secretion from pancreatic β-cells. The representative compound No. 8 (4,5-dimethoxy-2-propiolamidobenzoic acid), alone or in combination with metformin, is effective in preserving pancreatic β-cell function, treating and/or reversing, returning blood glucose concentration to a normal level in a diabetic.

18 Claims, 4 Drawing Sheets

A

| P value | CTR |
|---|---|
| CPD 8-100uM | 0.00000170 |
| CPD 8-10uM | 0.0000063 |
| CPD 8-1uM | 0.0000599 |
| CPD 8-0.1uM | 0.00016972 |
| CPD 8-0.01uM | 0.00749043 |

| P value | CTR |
|---|---|
| CPD58v-100uM | 0.00078375 |
| CPD58v-10uM | 0.00000287 |
| CPD58v-1uM | 0.01854009 |
| CPD58v-0.1uM | 0.00003604 |
| CPD58v-0.01uM | 0.13008143 |

| P value | CTR |
|---|---|
| CPD58s-100uM | 0.00000893 |
| CPD58s-10uM | 0.00165748 |
| CPD58s-1uM | 0.00326231 |
| CPD58s-0.1uM | 0.04826152 |
| CPD58s-0.01uM | 0.17427606 |

| P value | CTR |
|---|---|
| CPD58t-10uM | 0.0000118 |
| CPD58t-1uM | 0.0000732 |
| CPD58t-0.1uM | 0.0062923 |
| CPD58t-0.01uM | 0.0053588 |

B

A

B

PDIA4 INHIBITORS AND USE THEREOF FOR INHIBITING β-CELL PATHOGENESIS AND TREATING DIABETES

REFERENCE TO RELATED APPLICATION

This application is a national stage application (under 35 U.S.C. 371) of PCT/US2020/060639 filed 15 Nov. 2020, which claims priority to US provisional application 62/942,314 filed on 2 Dec. 2019, all of which are herein incorporated by reference in their entireties.

FIELD OF THE INVENTION

The present invention relates generally to PDIA4 inhibitors.

BACKGROUND OF THE INVENT ION

Type 2 diabetes (T2D) is characterized by peripheral insulin resistance, insufficient insulin secretion and progressive loss of β cell. Decline in β-cell function and mass is a central hallmark of T2D. Accumulating data suggest that preserving functional β-cell mass at early stages can delay and reverse T20. Therefore, identification of the key players in β-cell dysfunction and death could lead to a better understanding of β-cell pathogenesis and T2D development and new strategies for T2D treatment.

Protein disulfide isomerase (PDI) family (21 members) has multiple roles in cellular function and was reported to be implicated in infection, fertilization, coagulation, immunity, tumor metastasis or cell viability/growth. The role of protein disulfide isomerase (PDI) family in health and disease is poorly studied. Protein Disulfide-isomerase A3 (PDIA3) and protein Disulfide-Isomerase A4 (PDIA4) are two members of this family. Their function may not be redundant since mice deficient Pdia3 but not PDIM were shown to be lethal at embryonic stage. So far, no PDI-based drugs have been developed.

Approaches for preserving β-cell function and mass at the early diabetic stage, which can reverse T2D, are highly demanded.

SUMMARY OF THE INVENTION

In one aspect, the invention relates to a compound of formula (I) or a pharmaceutically acceptable salt thereof, (I)

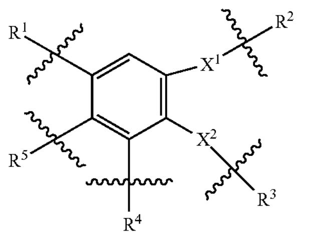

wherein:

$R^1$ is —C(═O)OR$^6$;

$R^2$ is $(C_1\text{-}C_6)$alkyl, benzyl, or -L-R$^{11}$, wherein L is a bond or $(C_1\text{-}C_6)$alkylene, and $R^{11}$ is phenyl, halo, dioxoisoindolin, —NR$^7$R$^8$, or —NR$^7$—CO—R$^8$;

$R^3$ is H, $(C_1\text{-}C_6)$alkyl, or benzyl;

$R^4$ is H, or $(C_1\text{-}C_6)$alkoxy;

$R^5$ is H, $(C_1\text{-}C_6)$amine, nitro, —NR$^7$R$^8$ or —NR$^7$—CO—R$^8$;

$X^1$ and $X^2$ is each independently —O—, —S—, or a covalent bond;

$R^6$ is H, halogen, $(C_1\text{-}C_6)$alkyl, $(C_1\text{-}C_6)$aryl, benzyl, halo$(C_1\text{-}C_6)$alkyl, —$(CH_2)_n$—Si$(CH_3)$, carbonyl$(C_1\text{-}C_6)$alkyne, wherein n is 1 to 6;

$R^7$ and $R^8$ is each independently H, $(C_1\text{-}C_6)$alkoxy, phenyl, benzoyl, halobenzoyl, benzyl, carbonyl$(C_1\text{-}C_6)$alkyne, $(C_1\text{-}C_6)$alkyne, oxazole, thiazole, or imidazole wherein optionally each of $(C_1\text{-}C_6)$alkoxy, phenyl, benzoyl and benzyl is independently substituted with one or more substituents selected from F, Cl, Br, I, $(C_1\text{-}C_6)$alkoxy, $(C_1\text{-}C_6)$alkyl, or halo$(C_1\text{-}C_6)$alkyl; or $R^7$ and $R^8$ together with the N atom form an benzimidic acid.

In one embodiment of the invention, $R^6$ is H or $(C_1\text{-}C_6)$alkyl, benzyl, halo$(C_1\text{-}C_6)$alkyl, —$(CH_2)_n$—Si$(CH_3)_3$, or carbonyl$(C_1\text{-}C_6)$alkyne.

In another embodiment of the invention, $R^2$ is $(C_1\text{-}C_6)$alkyl, or -L-R$^{11}$, in which L is $(C_1\text{-}C_6)$alkylene, and $R^{11}$ is dioxoisoindolin, —NR$^7$R$^8$, or —NR$^7$—CO—R$^8$, in which $R^7$ and $R^8$ is each independently H, phenyl, benzoyl, halobenzoyl, benzyl, carbonyl$(C_1\text{-}C_6)$alkyne, or oxazole.

In another embodiment, L is $(C_1\text{-}C_6)$alkylene, and $R^{11}$ is —NR$^7$—CO—R$^8$.

In another embodiment, L is $(C_1\text{-}C_6)$alkylene, and $R^{11}$ is —NR$^7$—CO—R$^8$, in which $R^7$ is carbonyl$(C_1\text{-}C_6)$alkyne, $R^9$ is oxazole, thiazole, or imidazole.

In another embodiment, $R^{11}$ is 1,3-dioxoisoindolin.

In another embodiment of the invention, the phenyl, benzoyl and/or benzyl is each independently substituted with one or more substituents selected from F, Cl, Br, I, or halo$(C_1\text{-}C_6)$alkyl.

In another embodiment of the invention, $R^5$ is —NR$^7$R$^8$ or —NR$^7$—CO—R$^8$, in which $R^7$ and $R^8$ is each independently H, or carbonyl$(C_1\text{-}C_6)$alkyne.

In another embodiment of the invention, $R^5$ is a nitro group.

In another embodiment of the invention, $R^6$ is carbonyl$(C_1\text{-}C_6)$alkyne.

In another embodiment of the invention, $R^2$ is -L-R$^{11}$, in which L is $(C_1\text{-}C_6)$alkylene, and $R^{11}$ is NR$^7$R$^8$, in which $R^7$ and $R^8$ together with the N atom form a benzimidic acid.

In another embodiment of the invention, $R^7$ and $R^8$ together with the N atom form an benzimidic acid.

In another embodiment of the invention, $R^2$ is -L-R$^{11}$, $R^{11}$ is —NR$^7$R$^8$, or —NR$^7$—CO—R$^8$; $R^7$ is carbonyl$(C_1\text{-}C_6)$alkyne and $R^8$ is benzoyl.

In another embodiment of the invention, $R^2$ is $(C_1\text{-}C_6)$alkyl; $R^3$ is $(C_1\text{-}C_6)$alkyl, $R^4$ is H, $R^5$ is —NR$^7$—CO—R$^8$, in which $R^7$ is H and $R^8$ is $(C_2)$alkyne.

In another embodiment of the invention, $R^5$ is —NR$^7$R$^8$, or —NR$^7$—CO—R$^8$, in which $R^7$ and $R^8$ is each independently H, carbonyl$(C_1\text{-}C_6)$alkyne, or $(C_1\text{-}C_6)$alkyne.

In another embodiment of the invention, $R^2$ is -L-R$^{11}$, in which L is $(C_1\text{-}C_6)$alkylene, and $R^{11}$ is dioxoisoindolin, or —NR$^7$R$^8$, in which $R^7$ and $R^8$ is each independently benzoyl, or carbonyl$(C_1\text{-}C_6)$alkyne.

In another embodiment, the compound or the pharmaceutically acceptable salt thereof of the invention is selected from the group consisting of compounds as listed in Table 6.

In another aspect, the invention relates to a pharmaceutical composition comprising: a compound or a pharmaceutically acceptable salt thereof of the invention; and a pharmaceutically acceptable carrier or excipient. The pharmaceutical composition may further comprise metformin.

In another aspect, the invention relates to a pharmaceutical composition comprising: (a) compound or a pharmaceutically acceptable salt thereof of the invention; and (b) metformin.

Further in another aspect, the invention relates to use of a compound or a pharmaceutically acceptable salt thereof, or a pharmaceutical composition of the invention in the manufacture of a medicament for augmenting insulin secretion from pancreatic β-cells, treating diabetes and/or reversing and returning blood glucose concentration to a normal level in a subject in need thereof.

The invention also relates to a compound or a pharmaceutically acceptable salt thereof, or a pharmaceutical composition of the invention for use in augmenting insulin secretion from pancreatic β-cells, treating diabetes and/or reversing and returning blood glucose concentration to a normal level in a subject in need thereof.

In one embodiment, a compound or a pharmaceutically acceptable salt thereof, or a pharmaceutical composition of the invention is for use in inhibiting PDIA4 activity, inhibiting pancreatic β-cell pathogenesis, treating diabetes and/or reversing and returning blood glucose concentration to a normal level in a subject in need thereof.

The invention also relates to a method of inhibiting pancreatic β-cell pathogenesis, augmenting insulin secretion from pancreatic β-cells, treating diabetes and/or reversing and returning blood glucose concentration to a normal level in a subject in need thereof, said method comprising administering to the subject in need thereof a therapeutically effective amount of a compound or a pharmaceutically acceptable salt thereof, or a pharmaceutical composition of the invention.

Yet in another aspect, the invention relates to a method of inhibiting PDIA4 activity, said method comprising causing a compound or a pharmaceutically acceptable salt thereof of the invention to be in contact with PDIA4 and thereby inhibiting the PDIA4 activity.

These and other aspects will become apparent from the following description of the preferred embodiment taken in conjunction with the following drawings, although variations and modifications therein may be affected without departing from the spirit and scope of the novel concepts of the disclosure.

The accompanying drawings illustrate one or more embodiments of the invention and, together with the written description, serve to explain the principles of the invention. Wherever possible, the same reference numbers are used throughout the drawings to refer to the same or like elements of an embodiment.

DETAILED DESCRIPTION OF THE INVENTION

Definitions

Figure 1:
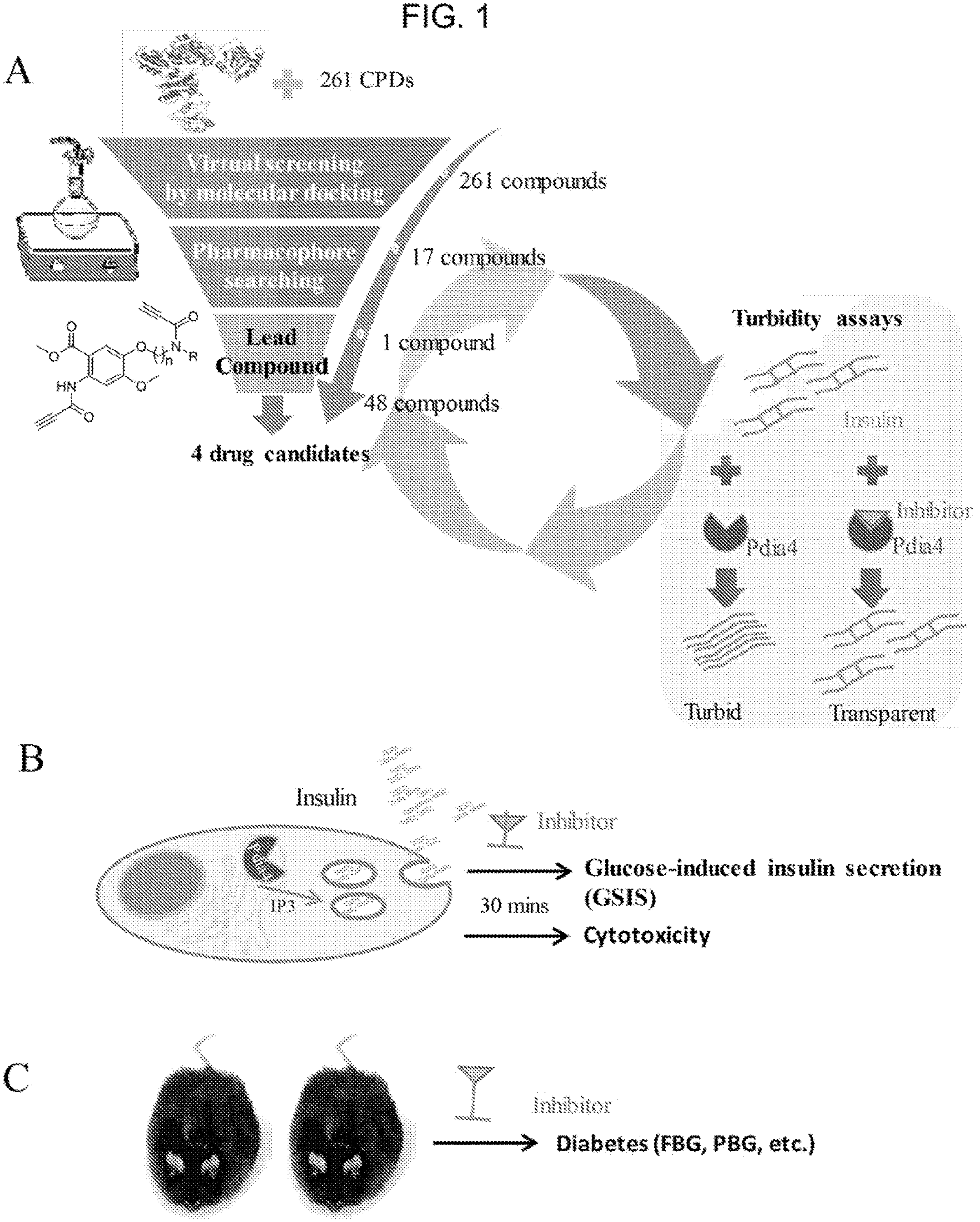
FIG. 1 is a flowchart describing the screening of PDIA4 inhibitors from hits to lead compounds and drug candidates. (A) A scheme describing a strategy of screening PDIA4 inhibitors from hits to leads and drug candidates using a combination of molecular docking, PDIA4 bioassays, and total synthesis. (B) Min6 cell-based assays for glucose-induced insulin secretion (GSIS) and cell viability. (C) Diabetic db/db & mice were used for PDIA4 inhibitors.

Representative acyl groups include acetyl, propionyl, butanoyl and benzoyl groups.

A dash ("-") that is not between two letters or symbols is used to indicate a point of attachment for a moiety or substituent. For example, the moiety $—CONH_2$ is attached through the carbon atom.

The term "ester," as used herein, means compounds containing a substituted carboxylic acid (e.g., —COO-alkyl).

The term "sulfonyl," as used herein, represents a group having the formula: $—S(O)_2—$.

The term "alkylene" refers to a saturated, branched or straight chain or cyclic hydrocarbon radical of 1-18 carbon atoms and having two monovalent radical centers derived by the removal of two hydrogen atoms from the same or different carbon atoms of a parent alkane. Typical alkylene radicals include but are not limited to methylene ($—CH_2—$), 1,2-ethylene ($—CH_2CH_2—$), 1,3-propylene ($—CH_2CH_2CH_2—$), 1,4-butylene ($—CH_2CH_2CH_2CH_2—$), and the like.

The term "($C_m$-$C_n$)", wherein m, n are integers, and n>m, means that all integer unit amounts within the range in to n are specifically disclosed as part of the invention. Thus, by "($C_m$-$C_n$)", it means that $C_m$, $C_{m+1}$, $C_{m+2}$, . . . , $C_{n-2}$, $C_{n-1}$, $C_n$, ($C_m$-$C_{m+1}$), ($C_m$-$C_{m+2}$), ($C_m$-$C_{m+3}$), . . . , ($C_m$-$C_{n-2}$), ($C_m$-$C_{n-1}$), ($C_m$-$C_n$); ($C_{m+1}$-$C_{m+2}$), ($C_{m+1}$-$C_{m+3}$), . . . , ($C_{m+1}$-$C_{n-2}$), ($C_{m+1}$-$C_{n-1}$), ($C_{m+1}$-$C_n$), . . . , ($C_{n-2}$-$C_{n-1}$), ($C_{n-2}$-$C_n$); and ($C_{n-1}$-$C_n$) are included as embodiments of this invention.

By "($C_1$-$C_6$)", it means that all integer unit amounts within the range 1 to 6 are specifically disclosed as part of the invention. Thus, $C_1$, $C_2$, $C_3$, $C_4$, $C_5$, $C_6$; ($C_1$-$C_2$), ($C_1$-$C_3$), ($C_1$-$C_4$), ($C_1$-$C_5$), ($C_1$-$C_6$); ($C_2$-$C_3$), ($C_2$-$C_4$), ($C_2$-$C_5$), ($C_2$-$C_6$); ($C_3$-$C_4$), ($C_3$-$C_5$), ($C_3$-$C_6$); ($C_4$-$C_5$), ($C_4$-$C_6$); and ($C_5$-$C_6$) units amounts are included as embodiments of this invention.

The term "treating" or "treatment" refers to administration of an effective amount of a therapeutic agent to a subject, who has a disease, or a symptom or predisposition toward such a disease, with the purpose to cure, alleviate, relieve, remedy, ameliorate, or prevent the disease, the symptoms of it, or the predispositions towards it.

The "Guidance for Industry and Reviewers Estimating the Safe Starting Dose in Clinical Trials for Therapeutics in Adult Healthy Volunteers" published by the U.S. Department of Health and Human Services Food and Drug Administration discloses "a human equivalent dose" may be obtained by calculations from the following formula:

HED=animal dose in mg/kg×(animal weight in kg/human weight in kg)$^{0.33}$.

Abbreviation: PDIA4, Protein Disulfide Isomerase Family A Member 4; CCTB, carbon/carbon triple bonds; $IC_{50}$, half maximal inhibitory concentration.

The invention relates to the discovery of PDIA4 inhibitors for treating type 2 diabetes. A combination of molecular docking and PDIA4 bioassays was used to identify PDIA4-based hits. A lead compound optimization was taken to improve its bioactivity until drug candidates with the $IC_{50}$ value within a nM range.

EXAMPLES

Materials and Methods

Virtual Screening

To obtain a reliable model of PDIA4 action, a multiple sequence alignment of the A chain of 31DV (catalytic domain (residues 53-284) of human PDIA4), 3EC3 (non-catalytic domain (residues 283-523) of rat PDIA4) and 3F8U (residues 25-501 of human PDIA3) from the Protein Data Bank was performed. The three protein sequences shared 100%, 88%, and 42% homology with human PDIA4, respectively. A homology model of PDIA4 was generated using Discovery Studio v.4.1 and was based on the crystallographic structures of the A chain of 3IDV, 3EC3 and 3F8U of PDIA4, which were used as structural templates. Two hundred sixty-one compounds from an in-house plant chemical library were converted to 3D coordinates using a CHARMM force field to minimize the compound by the Prepare Ligand module in Discovery Studio. The protonation states of residues were adjusted to the dominant ionic forms at pH 7.5. The surrounding residues of the second CGHC motif of PDIA4, which is composed of a binding packet between the first and second active domains, was employed as a docking packet. Molecular docking between the compounds and the second active domain of PDIA4 was performed using Goldscore within the GOLD v.5.1 program (CCDC Software Limited, Cambridge, UK). Finally, among the 100 docking conformations of the compounds, the best candidates (with higher GOLD fitness score) were chosen to explore the "inhibitor-bond" conformations in the second active domain of PDIA4.

Chemistry

The NMR spectrum ($^1$H and $^{13}$C NMR) were obtained with the Bruker Fourier 300 and AVIII 500 spectrometer using standard plus programs. The chemical shifts were cited in parts per million (ppm, δ) using TMS as an internal standard. The MS data were measured on Finnigan Mat. TSQ-7000 mass spectrometer (ESIMS and HRESIMS). The melting point was recorded on Fisher-Johns apparatus (uncorrected). The HPLC was performed on a C18 column (150 min×4.6 mm) by an L-2130 pump (Hitachi, Ibaraki, Japan). The column chromatography was performed on silica gel (70-230 mesh, Merck, Darmstadt, Germany). The TLC analysis was performed on silica gel plates (KG60-F254, Merck). Unless otherwise mentioned, all chemicals and materials were used as received from commercial suppliers without any purification, Anhydrous dichloromethane was distilled from calcium hydride under $N_2$.

Scheme 1

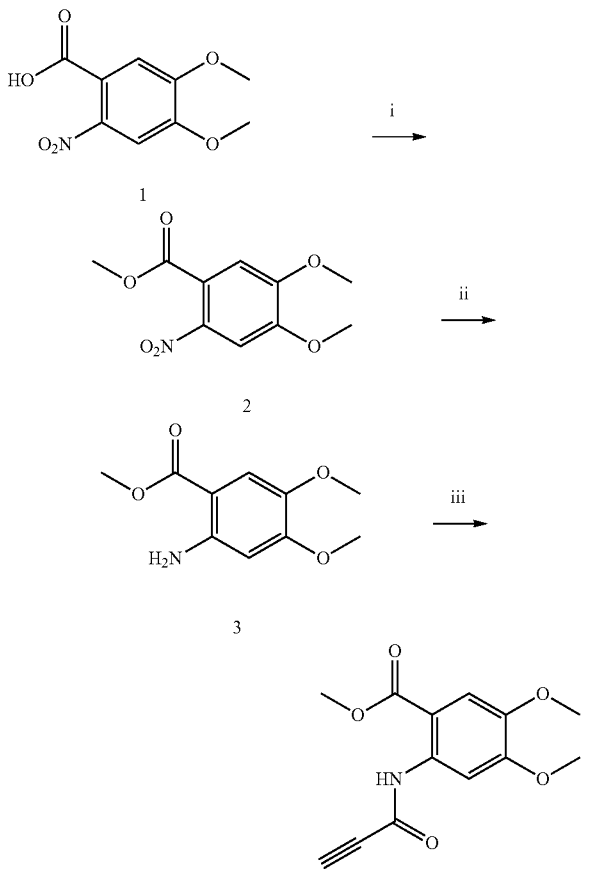

1

2

3

4

Reagents and conditions: (i) MeOH, 60° C; (ii) 10% Pd-C, EtOAc, RT; (iii) propiolic acid, DCC, $CH_2Cl_2$, 0° C.

Methyl 4,5-dimethoxy-2-nitrobenzoate (2)

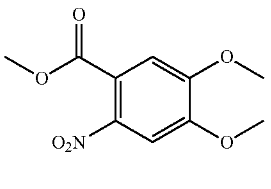

To a mixture of 1 (5.00 g, 22.00 mmol) and $K_2CO_3$ (12.17 g, 88.04 mmol) in DMF (50 mL) was added $CH_3I$ (5.48 mL, 88.04 mmol) dropwise. The resulting solution was heated to 100° C. under $N_2$ for 15 h. The reaction mixture was suspended in $H_2O$ (150 mL) and then extracted with EtOAc (3×150 mL). The combined organic layer was dried over $MgSO_4$, filtered and concentrated in vacuo to get a solid. The solid was washed with. MeOH to afford 2 (5.22 g, 98%). $^1$H NMR (500 MHz, $CDCl_3$) δ 7.43 (s, 1H), 7.06 (s, 1H), 3.96 (s, 3H), 3.95 (s, 3H), 3.89 (s, 3H).

methyl 2-amino-4,5-dimethoxybenzoate (3)

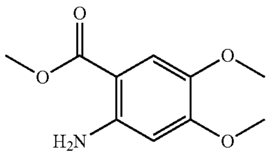

To a solution oft (5.22 g, 21.66 mmol) in EtOAc (10 mL) was added a catalytic amount of 10% Pd/C (1 g). The mixture was stirred at RT under $H_2$ atmosphere for 8 h. The reaction mixture was filtered with celite and the filtrate was concentrated in vacuo. The residue was purified by silica gel chromatography (EtOAc/n-hexane=1:9) to afford 3 (3.00 g, 66%) as yellow solid. $^1$H NMR (500 MHz, $CDCl_3$) δ 7.27 (s, 1H), 6.12 (s, 1H), 5.55 (s, 2H), 3.84 (s, 3H), 3.83 (s, 3H), 3.80 (s, 3H).

methyl 4,5-dimethoxy-2-propiolamidobenzoate (4)

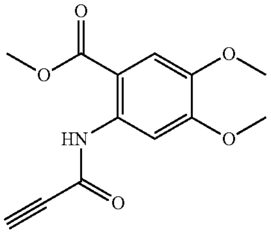

To a solution of 3 (50 mg, 0.24 mmol) in dry $CH_2Cl_2$ (10 ML) was added propiolic acid (0.022 mL, 0.36 mmol) and N, N'-dicyclohexylcarbodiimide (73 mg, 0.36 mmol) in dry $CH_2Cl_2$ (5 mL) dropwise in an ice-bath. The resulting solution was stirred under $N_2$ for 2 h. The reaction mixture was suspended in $H_2O$ (50 mL) and then extracted with $CH_2Cl_2$ (3×50 mL). The combined organic layer was dried over $MgSO_4$, filtered and concentrated in vacuo. The mixture was filtered and washed with EtOAc/n-hexane=1:1 (10 mL). The residue was purified by silica gel chromatography (EtOAc/n-hexane=1:5) to afford 4 (57 mg, 91%), $^1$H NMR (500 MHz, $CDCl_3$), δ 11.56 (s, 1H), 8.31 (s, 1H), 7.44 (s, 1H), 3.93 (s, 3H), 3.90 (s, 3H), 3.87 (s, 3H), 2.92 (s, 1H).

Scheme 2

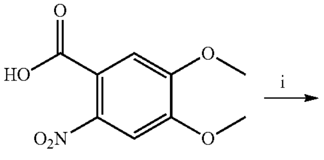

1

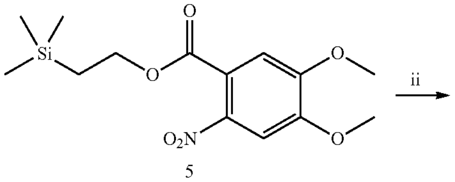

5

-continued

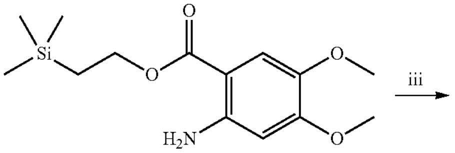

6

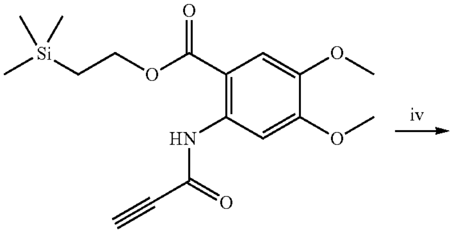

7

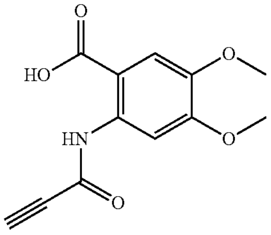

8

Reagents and conditions: (i) DMAP, DCC, $(CH_3)_3Si(CH_2)_2OH$, THF, RT; (ii) 10% Pd-C, EtOAc, $H_2$, RT; (iii) propiolic acid, DCC, $CH_2Cl_2$, 0° C.; (iv) TBAF, THF, RT.

2-(trimethylsilyl)ethyl 4,5-dimethoxy-2-nitrobenzoate (5)

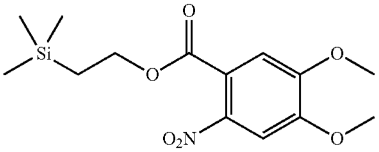

Following the procedure described for compound 4, reaction of 1 (100 mg, 0.44 mmol), N, N'-dicyclohexylcarbodiimide (109 mg, 0.528 mmol) and DMAP (5 mg, 0.04 mmol) in dry THF (10 mL) was added 2-(trimethylsilyl) ethanol (0.094 mL, 0.66 mmol) dropwise to afford 5 (59 mg, 41%). $^1$H NMR (300 MHz, $CDCl_3$) δ 7.43 (s, 1H) 7.05 (s, 1H) 4.38 (m, 2H), 3.06 (s, 3H), 3.95 (s, 3H), 1.08 (m, 2H), 0.04 (s, 9H).

2-(trimethylsilyl)ethyl 2-amino-4,5-dimethoxybenzoate (6)

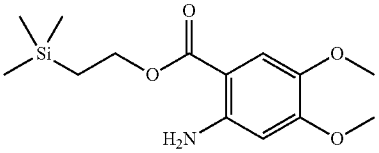

Following the procedure described for compound 3, reaction of 5 (100 mg, 0.31 mmol) in EtOAc (10 mL) was added a catalytic amount of 10% Pd/C (10 mg) to afford 6 (41 mg, 45%), $^1$H NMR (300 MHz, $CDCl_3$) δ 7.29 (s, 1H), 6.12 (s, 1H), 4.34 (m, 2H), 3.84 (s, 3H), 3.80 (s, 3H), 1.10 (m, 2H), 0.07 (s, 9H).

2-(trimethylsilyl)ethyl 4,5-dimethoxy-2-propiolamidobenzoate (7)

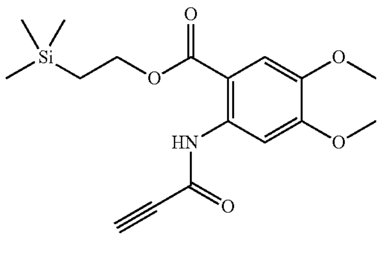

Following the procedure described for compound 4, reaction of 6 (100 mg, 0.34 mmol) in dry $CH_2Cl_2$ (10 mL) was added propiolic acid (0.031 mL, 0.50 mmol) and N, N'-dicyclohexylcarbodiimide (104 mg, 0.50 mmol) in dry $CH_2Cl_2$ (5 mL) dropwise in an ice-bath to afford 7 (108 mg, 92%) $^1$H NMR (300 MHz, $CDCl_3$) δ 11.65 (s, 1H), 8.32 (s, 1H), 7.45 (s, 1H), 4.41 (m, 2H), 3.94 (s, 3H), 3.87 (s, 3H), 1.14 (m, 2H), 0.08 (s, 9H).

4,5-dimethoxy-2-propiolamidobenzoic acid (8)

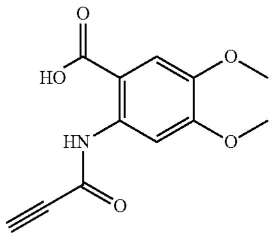 [SMILES: C#CC(=O)Nc1cc(OC)c(OC)cc1C(=O)O]

To a solution of 7 (50 mg, 0.14 mmol) in dry THF (4 mL) was added TBAF (1M in THF, 0.43 ml, 0.43 mmol) dropwise at RT. The resulting solution was stirred under $N_2$ for 24 h. The reaction mixture was extracted with 1 N $HCl_{(aq)}$ (50 mL) and EtOAc (3×50 mL). The combined organic layer was dried over $MgSO_4$, filtered and concentrated in vacuo. The residue was purified by silica gel chromatography ($MeOH/CH_2Cl_2$=3:97) to afford 8 (30 mg, 84%). $^1$H NMR (500 MHz, DMSO) δ 11.87 (s, 1H), 8.06 (s, 1H), 7.45 (s, 1H), 4.45 (s, 1H), 3.80 (s, 3H), 3.77 (s, 3H), Scheme 3

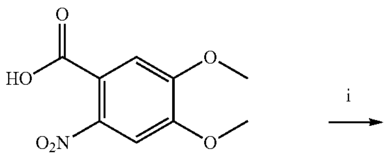

1

-continued

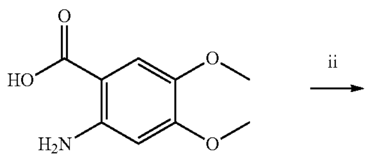

9

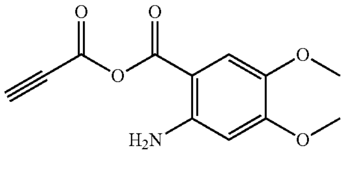

10

Reagents and conditions: (i) 10% Pd-C, EtOAc, $H_2$, MeOH, RT; (ii) propiolic acid, DCC, $CH_2Cl_2$, 0° C.

2-amino-4,5-dimethoxybenzoic acid (9)

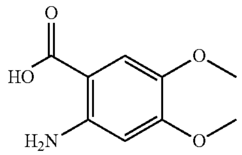

To a solution of 1 (5.00 g, 22.00 mmol) in MOH (20 mL) was added a catalytic amount of 10% Pd/C (1.5 g) and the mixture was stirred at RT under $H_2$ atmosphere for 24 h. The reaction mixture was filtered with celite and concentrated in vacuo to afford 9 (4.00 g, 92%). $^1$H NMR (500 MHz, DMSO) δ 7.14 (s, 1H), 6.33 (s, 1H), 3.73 (s, 3H), 3.63 (s, 3H).

2-amino-4,5-dimethoxybenzoic propiolic anhydride (10)

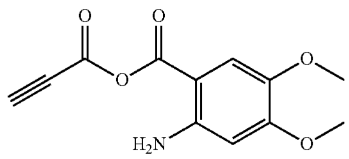 [SMILES: C#CC(=O)OC(=O)c1cc(OC)c(OC)cc1N]

Following the procedure described for compound 4, reaction of 9 (500 mg, 2.54 mmol) in dry $CH_2Cl_2$ (10 mL) was added propiolic acid (0.234 mL, 3.81 mmol) and N, N'-dicyclohexylcarbodiimide (466 mg, 2.26 mmol) in dry $CH_2Cl_2$ (5 mL) dropwise in an ice-bath to afford 10 (15 mg, 2%). $^1$H NMR (300 MHz, $CDCl_3$) δ 7.50 (s, 1H), 7.02 (s, 1H), 3.97 (s, 3H), 3.96 (s, 3H).

Scheme 4

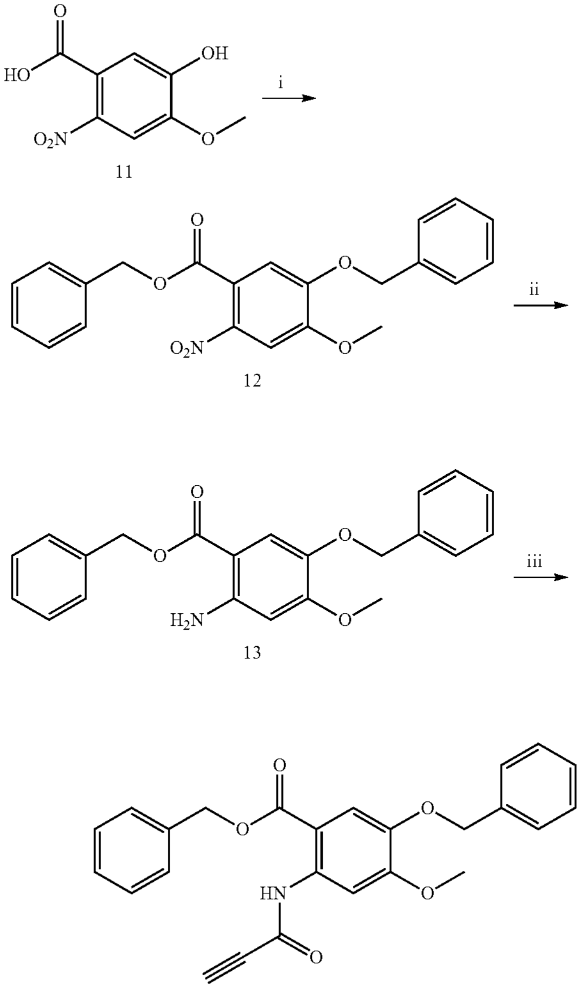

11

12

13

14

Reagents and conditions: (i) BnBr, $K_2CO_3$, DMF, 110° C.; (ii) Zn, AcOH, 50° C.; (iii) propiolic chloride, $K_2CO_3$, $CH_2Cl_2$, 0° C.

benzyl 5-(benzyloxy)-4-methoxy-2-nitrobenzoate (12)

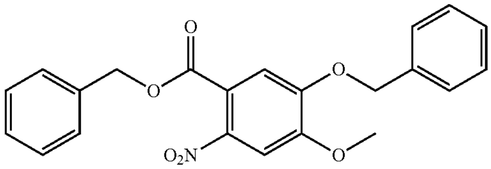

Following the procedure described for compound 2, reaction of 11 (439 mg, 2.00 mmol) and $K_2CO_3$ (710 mg, 5.15 mmol) in DMF (20 mL) was added benzyl bromide (0.61 mL, 5.15 mmol). The resulting solution was heated to 110° C. wider $N_2$ to afford 12 (807 mg, 99%). $^1H$ NMR (500 MHz, $CDCl_3$) δ 7.43 (s, 1H), 7.34 (m, 10H), 7.13 (s, 1H), 5.30 (s, 2H), 5.18 (s, 2H), 3.96 (s, 3H).

benzyl 2-amino-5-(benzyloxy)-4-methoxybenzoate (13)

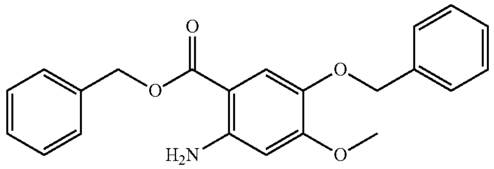 [SMILES: COc1cc([N+](=O)[O-])c(C(=O)OCc2ccccc2)cc1OCc1ccccc1]

To a solution of 12 (1.00 g, 2.54 mmol) HOAc (20 mL) was added Zn (1.66 g, 25.44 mmol) and the mixture was heated to 50° C. under $N_2$ for 24 h. The reaction mixture was filtered with celite. The residue was dissolved in EtOAc (50 mL) and then washed with $NaHCO_3$ (3×50 mL). The combined organic layer was dried over $MgSO_4$, filtered and concentrated in vacuo. The residue was purified by silica gel chromatography (EtOAc/n-hexane=1:3) to afford 13 (330 mg, 36%). $^1H$ NMR (500 MHz, $CDCl_3$) δ 7.37 (m, 1H), 6.15 (s, 1H), 5.64 (s, 2H), 5.28 (s, 2H), 5.04 (s, 2H), 3.87 (s, 3H).

benzyl 5-(benzyloxy)-4-methoxy-2-propiolamidobenzoate (14)

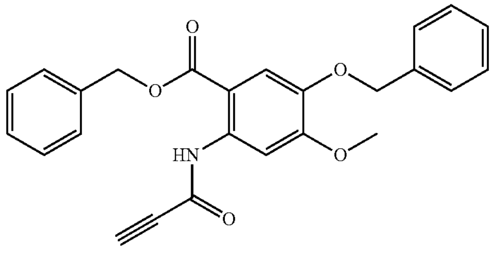 [SMILES: C#CC(=O)Nc1cc(OC)c(OCc2ccccc2)cc1C(=O)OCc1ccccc1]

To a solution of 13 (500 mg, 1.37 mmol) in dry $CH_2Cl_2$ (30 mL) was added propiolic chloride (1.00 g, 11.36 mmol) dropwise and $K_2CO_3$ (475 mg, 3.44 mmol) in an ice-bath. The resulting solution was stirred at 0° C. under $N_2$ for 0.5 h. The reaction mixture was suspended in $H_2O$ (50 mL) and extracted with $CH_2Cl_2$ (3×50 mL). The combined organic layer was dried over $MgSO_4$, filtered and concentrated in vacuo. The residue was purified by silica gel chromatography (EtOAc/n-hexane=1:4) to afford 14 (76 mg, 13%). $^1H$ NMR (500 MHz, $CDCl_3$) δ 11.52 (s, 1H), 8.36 (s, 1H), 7.56 (s, 1H), 7.37 (m, 10H), 5.33 (s, 2H), 5.13 (s, 2H), 4.71 (s, 1H), 3.97 (s, 3H).

Scheme 5

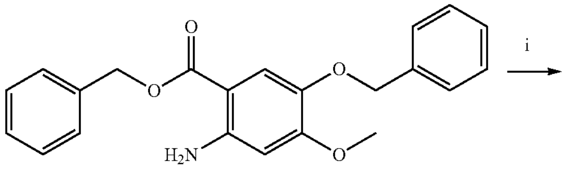

13

-continued

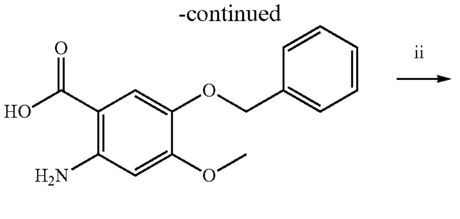

15

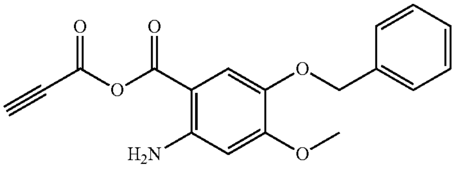

16

Reagents and conditions: (i) LiOH, MeOH, 80° C; (ii) propiolic acid, DCC, $CH_2Cl_2$, 0° C.

2-amino-5-(benzyloxy)-4-methoxybenzoic acid (15)

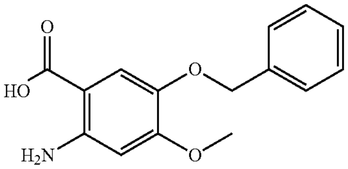 [SMILES: COc1cc(N)c(C(=O)O)cc1OCc1ccccc1]

The solution of 13 (150 mg, 0.41 mmol) and LiOH (100 mg, 2.30 mmol) in MeOH (10 mL) was heated to 70° C. under $N_2$ for 18 h. The resulting solution was acidified to pH 2 and extracted with 1 N HCl (50 mL) and EtOAc (3×50 mL). The combined organic layer was dried over $MgSO_4$, filtered and concentrated in vacuo. The residue was recrystallized to afford 15 (100 mg, 89%). $^1$H NMR (500 MHz, $CDCl_3$) 7.43 (S, 1H), 7.41 (s, 2H), 7.35 (t, J=7.4 Hz, 2H), 7.28 (t, J=7.3 Hz, 1H), 6.1.2 (s, 1H), 5.02 (s, 2H), 3.85 (s, 3H).

2-amino-5-(benzyloxy)-4-methoxybenzoic propiolic anhydride (16)

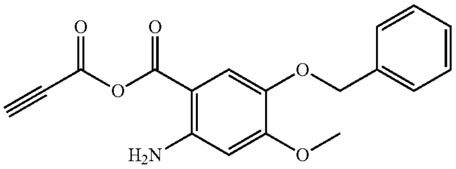 [SMILES: C#CC(=O)OC(=O)c1cc(OCc2ccccc2)c(OC)cc1N]

Following the procedure described for compound 4, reaction of 15 (2.50 mg, 0.92 mmol) in dry $CH_2Cl_2$ (10 mL) was added propiolic acid (0.084 mL, 0.92 mmol) and N, N'-dicyclohexylcarbodiimide (246 mg, 119 mmol) in dry $CH_2Cl_2$ (5 mL) dropwise in an ice-bath to afford 16 (36 mg, 12%). $^1$H NMR (500 MHz, $CDCl_3$) δ 7.57 (s, 1H), 7.44 (d, J=7.3 Hz, 2H), 7.37 (t, J=7.5 Hz, 2H), 7.32 (t, J=7.3 Hz, 1H), 7.04 (s, 1H), 5.21 (s, 2H), 3.97 (s, 3H), 3.20 (s, 1H).

Scheme 6

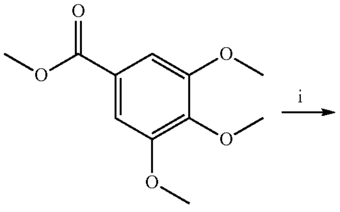

17

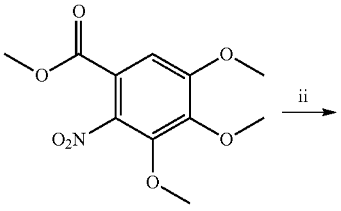

18

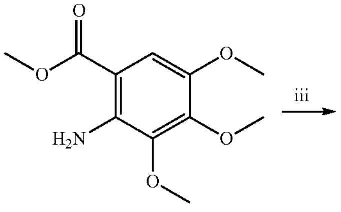

19

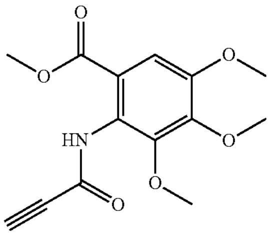

20

Reagents and conditions: (i) $HNO_3$, AcOH, 50° C.; (ii) Zn, AcOH, 50° C.; (iii) propiolic chloride, $K_2CO_3$, $CH_2Cl_2$, 0° C.

3,4,5-trimethoxy-2-nitrobenzoate (18)

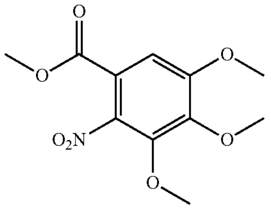

To a solution of 17 (500 mg, 2.21 mmol) in HOAc (4 mL) was added $HNO_3$ (2 mL) and heated to 50° C. under $N_2$ for 1.5 h. The reaction mixture was suspended in $H_2O$ (50 mL) and then extracted with EtOAc (3×50 mL). The combined organic layer was dried over $MgSO_4$, filtered and concentrated in vacuo. The residue was purified by silica gel chromatography (EtOAc/n-hexane=1:4) to afford 18 (231 mg, 38%). $^1H$ NMR (500 MHz, $CDCl_3$) δ 7.25 (s, 1H), 3.94 (s, 3H), 3.93 (s, 3H), 3.92 (s, 3H), 3.85 (s, 3H).

methyl 2-amino-3,4,5-trimethoxybenzoate (19)

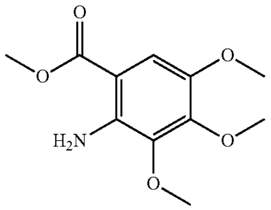

Following the procedure described for compound 13, reaction of 18 (1.00 g, 3.69 mmol) in HOAc (20 mL) was added Zn (2.41 g, 36.90 mmol) and the mixture was heated to 50° C. under $N_2$ for 24 h. The reaction mixture was filtered with celite. The residue was extracted with EtOAc (50 mL) and $NaHCO_3$ (3×50 mL). The combined organic layer was dried over $MgSO_4$, filtered and concentrated in vacuo. The residue was purified by silica gel chromatography. EtOAc/n-hexane=1:4) to afford 19 (590 mg, 66%). $^1H$ NMR (500 MHz, $CDCl_3$) δ 7.13 (s, 3H), 3.93 (s, 3H), 3.84 (s, 6H), 3.79 (s, 3H).

methyl 3,4,5-trimethoxy-2-propiolamidobenzoate (20)

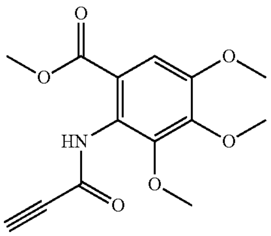

Following the procedure described for compound 14, reaction of 19 (1.36 g, 5.68 mmol) in dry $CH_2Cl_2$ (30 mL) was added propiolic chloride (1.00 g, 11.36 mmol) dropwise and $K_2CO_3$ (1.57 g, 3.11.36 mmol) in an ice-bath to afford 20 (148 mg, 9%). $^1H$ NMR (500 MHz, $CDCl_3$) δ 7.20 (s, 1H), 3.92 (s, 3H), 3.91 (s, 3H), 3.88 (s, 3H), 3.87 (s, 3H), 2.88 (s, 1H).

Scheme 7

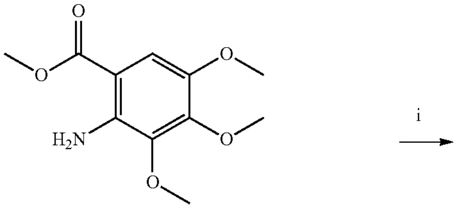

19

-continued

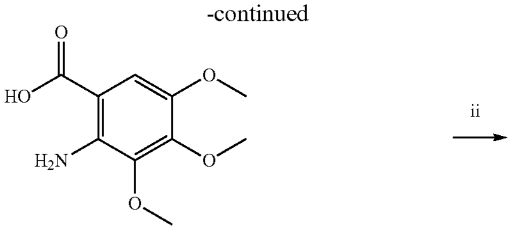

21

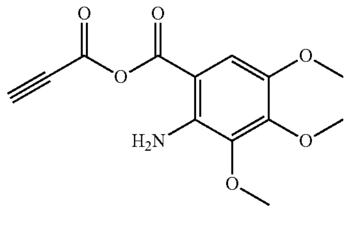

22

Reagents and conditions: (i) LiOH, MeOH, 80° C; (ii) propiolic acid, DCC, $CH_2Cl_2$, 0° C.

2-amino-3,4,5-trimethoxybenzoic acid (21)

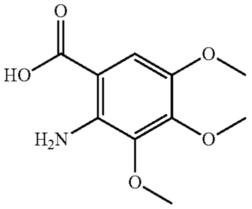 [SMILES: COc1cc(C(=O)O)c(N)c(OC)c1OC]

Following the procedure described for compound 15 reaction of 19 (560 mg, 2.32 mmol) and LiOH (240 mg, 5.72 mmol) in MeOH (10 mL) was heated to 70° C. under $N_2$ for 18 h to afford 21 (380 mg, 73%). $^1H$ NMR (500 MHz, $CDCl_3$) δ 7.19 (s, 1H), 3.95 (s, 3H), 3.86 (s, 3H), 3.80 (s, 3H).

2-amino-3,4,5-trimethoxybenzoic propiolic anhydride (22)

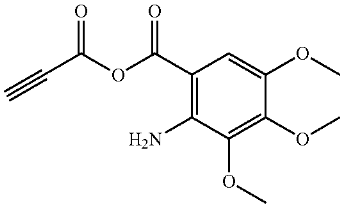 [SMILES: C#CC(=O)OC(=O)c1cc(OC)c(OC)c(OC)c1N]

Following the procedure described for compound 4, reaction of 21 (320 mg, 1.41 mmol) in dry $CH_2Cl_2$ (10 was added propiolic acid (0.130 mL, 2.11 mmol) and N, N'-dicyclohexylcarbodiimide (435 mg, 2.11 mmol) in dry $CH_2Cl_2$ (5 mL) dropwise in an ice-bath to afford 22 (6 mg 2%). $^1$H NMR (500 MHz, $CDCl_3$) δ 7.39 (s, 1H), 4.05 (s, 3H), 4.01 (s, 3H), 3.95 (s, 3H), 3.19 (s, 1H).

Scheme 8

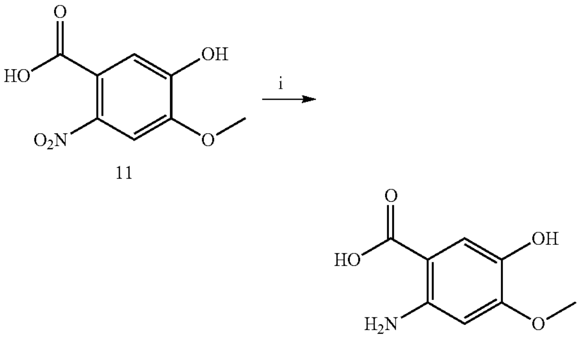

11

23

Reagents and conditions: (i) 10% Pd-C, MeOH, $H_2$, RT; (ii) propiolic acid, DCC, $CH_2Cl_2$, 0° C.

2-amino-5-hydroxy-4-methoxybenzoic acid (23)

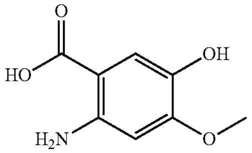

To a solution of 11 (500 mg, 2.35 mmol) in MeOH (30 mL) was added a catalytic amount of 10% Pd/C (200 mg) and the mixture was stirred at RT under $H_2$ atmosphere for 9 h. The reaction mixture was filtered with celite and the filtrate was concentrated in vacuo. The residue was purified by silica gel chromatography ($MeOH/CH_2Cl_2$=1:9) to afford 23 (350 mg, 82%). $^1$H NMR (300 MHz, $CDCl_3$) δ 8.30 (s, 1H), 7.18 (s, 1H), 6.38 (S, 1H), 3.83 (s, 3H) 3.27 (s, 1H).

Scheme 9

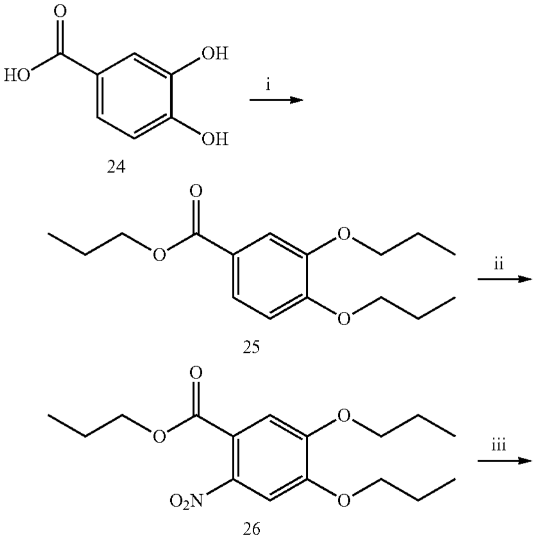

24

25

26

-continued

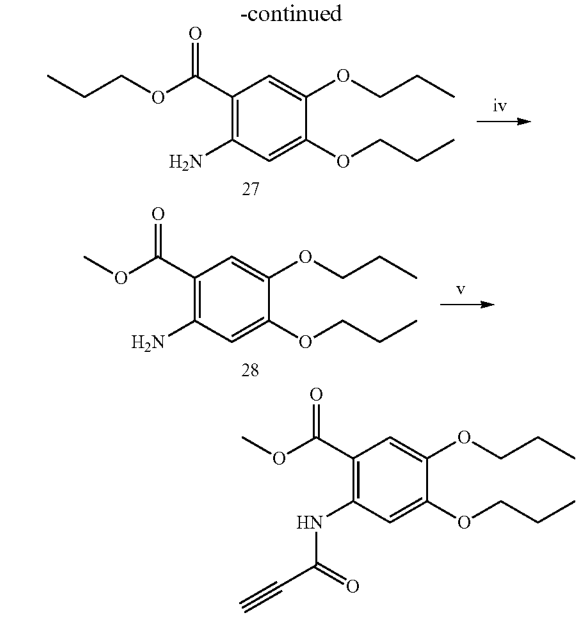

27

28

29

Reagents and conditions: (i) propyl bromide, $K_2CO_3$, DMF, 100° C.; (ii) $HNO_3$, AcOH, 50° C.; (iii) Zn, AcOH, 50° C.; (iv) LiOH, MeOH, 80° C.; (v) propiolic acid, DCC, $CH_2Cl_2$, 0° C.

propyl 3,4-dipropoxybenzoate (25)

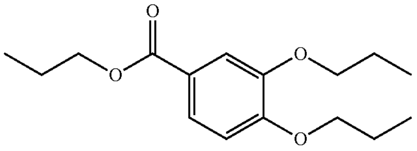 [SMILES: CCCOC(=O)c1ccc(OCCC)c(OCCC)c1]

Following the procedure described for compound 2, reaction of 24 (5 g, 32.47 mmol) and $K_2CO_3$ (22.36 g, 162 mmol) in DMF (50 mL) was added 1-bromopropane (13.2 mL, 145 mmol). The resulting solution was heated to 110° C. under $N_2$ to afford 25 (8.5 g, 89%). $^1$H NMR (300 MHz, $CDCl_3$) δ 7.62 (dd, 8.4, 2.0 Hz, 1H), 7.53 (d, J=2.0 Hz, 1H), 6.85 (d, J=8.4 Hz, 1H), 4.22 (t, J=6.7 Hz, 2H), 3.99 (t, J=6.6 Hz, 4H), 1.80 (m, 6H), 1.02 (m, 9H).

propyl 2-nitro-4,5-dipropoxybenzoate (26)

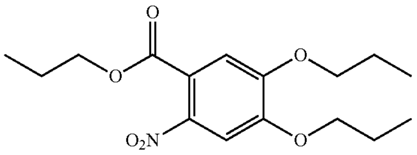

Following the procedure described for compound 18, reaction of 25 (8.10 g, 28.93 mmol) in HOAc (20 mL) was added $HNO_3$ (5 mL) and heated to 50° C. under $N_2$ to afford 26 (8.50 g, 90%). $^1$H NMR (300 MHz, $CDCl_3$) δ 7.40 (s, 1H), 7.04 (s, 1H), 4.24 (t, J=6.7 Hz, 2H), 4.02 (m, 4H), 1.86 (sxt, J=7.1 Hz, 4H), 1.72 (m, 2H), 1.04 (td, J=7.4, 1.5 Hz, 6H), 0.95 (t, J=7.4 Hz, 3H).

propyl 2-amino-4,5-dipropoxybenzoate (27)

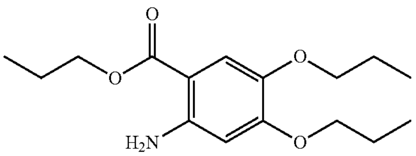 [SMILES: CCCOC(=O)c1cc(OCCC)c(OCCC)cc1[N+](=O)[O-]]

To a solution of 26 (8.50 g, 26.15 mmol) in HOAc (20 mL) was added Zn (17.00 g, 261.54 mmol) and the mixture was stirred at RT under $N_2$ for 2 h. The reaction mixture was filtered with celite. The residue was extracted with EtOAc (150 mL) and $NaHCO_3$ (3×150 mL). The combined organic layer was dried over $MgSO_4$, filtered and concentrated in vacuo. The residue was purified by silica gel chromatography (EtOAc/n-hexane=1.7) to afford 27 (4.90 g, 64%). $^{1}$H NMR (300 MHz, $CDCl_3$) δ 7.36 (s, 1H), 6.10 (s, 1H), 4.18 (t, J=6.7 Hz, 2H), 3.88 (m, 4H), 1.79 (m, 6H), 1.01 (m, 9H).

methyl 2-amino-4,5-dipropoxybenzoate (28)

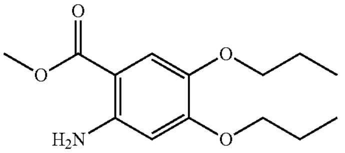 [SMILES: CCCOc1cc(N)c(C(=O)OC)cc1OCCC]

To a solution of 27 (1 g, 3.86 mmol) and LiOH (810 mg, 19.30 mmol) MeOH (20 mL) was heated to 70° C. under $N_2$ for 24 h. The resulting solution was acidified to pH 2 and extracted with 1N HCl (50 mL) and EtOAc (3×50 mL). The combined organic layer was dried over $MgSO_4$, filtered and concentrated in vacuo. The residue was recrystallized to afford 28 (450 mg, 46%). $^{1}$H NMR (300 MHz, $CDCl_3$) δ 7.32 (s, 1H), 6.10 (s, 1H), 3.89 (m, 2H), 3.81 (s, 3H), 1.80 (m, 4H), 1.01 (m, 6H).

methyl 2-propiolamido-4,5-dipropoxybenzoate (29)

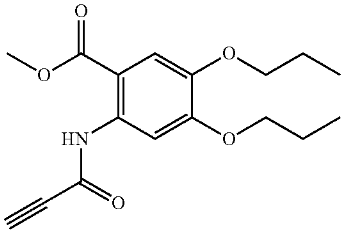 [SMILES: C#CC(=O)Nc1cc(OCCC)c(OCCC)cc1C(=O)OC]

Following the procedure described for compound 4, reaction of 28 (440 mg, 1.74 mmol) in dry $CH_2Cl_2$ (10 mL) was added propiolic acid (0.183 mL, 2.61 mmol) and N, N'-dicyclohexylcarbodiimide (466 mg, 2.26 mmol) in dry $CH_2Cl_2$ (5 mL) dropwise in an ice-bath to afford 29 (66 mg, 12%). $^{1}$H NMR (300 MHz, $CDCl_3$) δ 11.52 (s, 1H), 8.27 (s, 1H), 7.46 (s, 1H), 4.03 (t, J=6.6 Hz, 2H), 3.94 (t, J=6.6 Hz, 2H), 3.89 (s, 3H), 2.91 (s, 1H), 1.83 (m, 4H), 1.02 (t, J=7.4 Hz, 6H).

Scheme 10

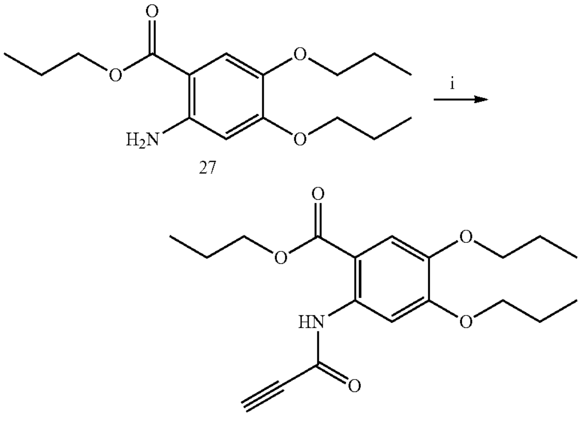

27

30

Reagents and conditions: (i) propiolic acid, DCC, $CH_2Cl_2$, 0° C.

propyl 2-propiolamido-4,5-dipropoxybenzoate (30)

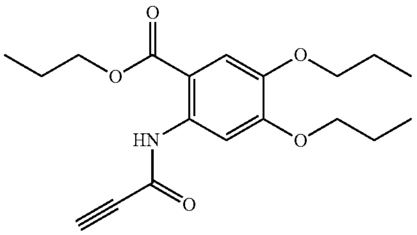 [SMILES: C#CC(=O)Nc1cc(OCCC)c(OCCC)cc1C(=O)OCCC]

Following the procedure described for compound 4, reaction of 27 (590 mg, 2.00 mmol) in dry $CH_2Cl_2$ (10 mL) was added propiolic acid (0.184 mL, 3.00 mmol) and N, N'-dicyclohexylcarbodiimide (453 mg, 2.19 mmol) in dry $CH_2Cl_2$ (5 mL) dropwise in an ice-bath to afford 30 (342 mg, 49%). $^{1}$H NMR (300 MHz, $CDCl_3$) δ 11.56 (s, 8.27 (s, 1H), 7.48 (s, 1H), 4.25 (t, J=6.7 Hz, 2H), 4.03 (t, J=6.6 Hz, 2H), 3.94 (t, J=6.6 Hz, 2H), 2.90 (s, 1H), 1.82 (m, 6H), 1.02 (m, 9H).

Scheme 11

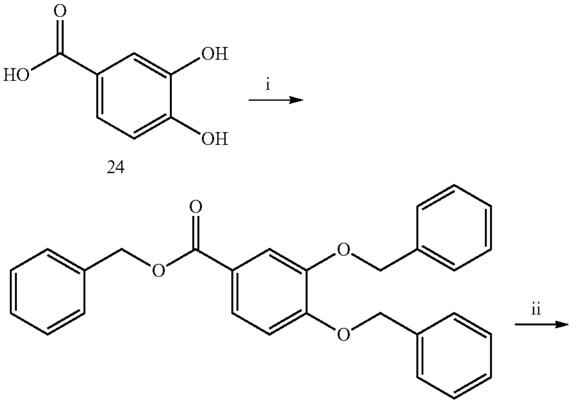

24

31

-continued

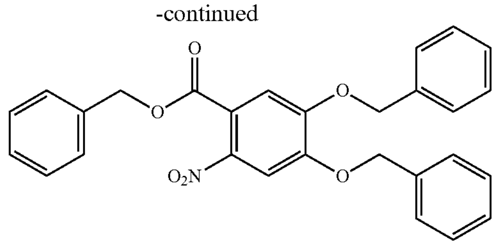

32

Reagents and conditions: (i) propyl bromide, $K_2CO_3$, DMF, 100° C.; (ii) $HNO_3$, AcOH, 50° C.

benzyl 3,4-bis(benzyloxy)benzoate (31)

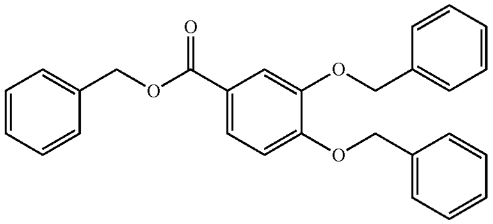 [SMILES: O=C(OCc1ccccc1)c1ccc(OCc2ccccc2)c(OCc2ccccc2)c1]

Following the procedure described for compound 2, reaction of 24 (10.00 g, 64.94 mmol) and $K_2CO_3$ (44.00 g, 318.23 mmol) DMF (100 mL) was added benzyl bromide (27 mL, 227.3 mmol). The resulting solution was heated to 110° C. under $N_2$ to afford 31 (27.10 g, 98%). $^1$H NMR (300 MHz, $CDCl_3$) δ 7.53 (s, 1H) 7.35 (m, 15H), 7.18 (s, 1H), 5.33 (s, 2H), 5.23 (s, 4H).

benzyl 4,5-bis(benzyloxy)-2-nitrobenzoate (32)

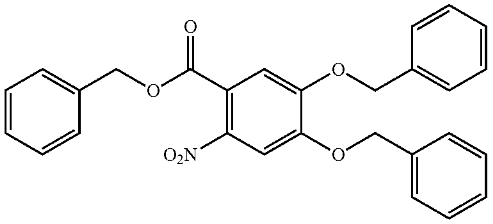 [SMILES: O=C(OCc1ccccc1)c1cc(OCc2ccccc2)c(OCc2ccccc2)cc1[N+](=O)[O-]]

Following the procedure described for compound 18, reaction of 3.1 (16.00 g, 37.69 mmol) its HOAc (30 mL) was added $HNO_3$ (15 mL) and stirred at RT under $N_2$ to afford 32 (16.44 g, 95%). $^1$H NMR (300 MHz, $CDCl_3$) δ 7.50 (s, 1H), 7.36 (m, 15H), 7.15 (s, 1H), 5.30 (s, 2H), 5.20 (s, 4H).

Scheme 12

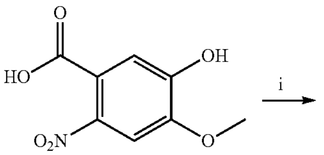

11

-continued

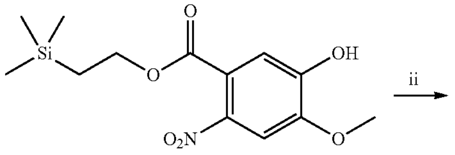

33

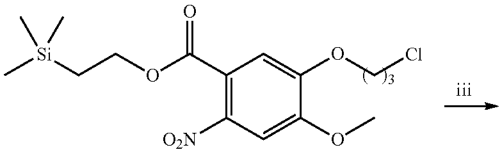

34

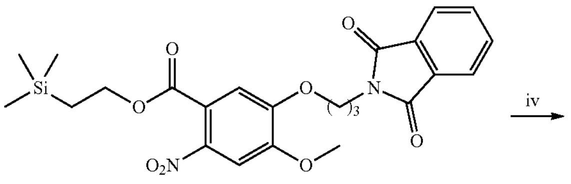

35

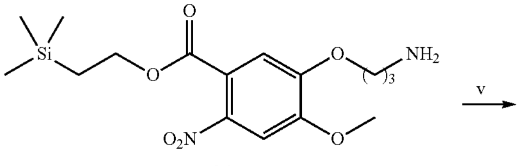

36

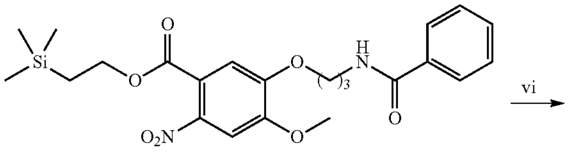

37

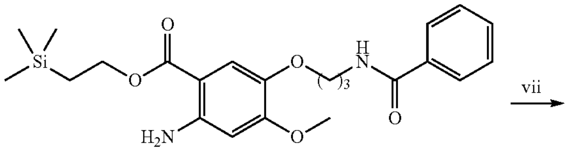

38

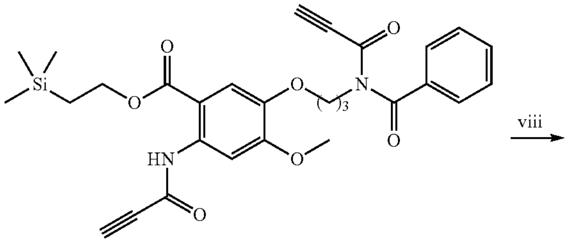

39

-continued

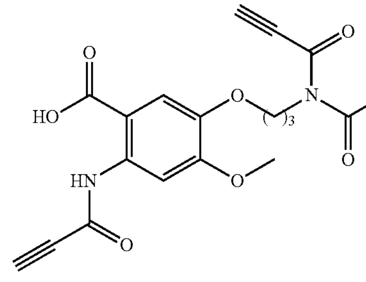

40

Reagents and conditions: (i) $(CH_3)_3Si(CH_2)_2OH$, $Ph_3P$, DIAD, THF, RT; (ii) 1-bromo-3-chloropropane, $K_2CO_3$, DMF, 100° C.; (iii) potassium phthalimide, $K_2CO_3$, DMF, 100° C.; (iv) $NH_2NH_2$—$H_2O$, MeOH, 60° C.; (v) benzoyl chloride, pyridine, $CH_2Cl_2$; (vi) Zn, AcOH, THF, RT; (vii) propiolic acid, DCC, $CH_2Cl_2$, 0° C.; (viii) TBAF, THF, RT.

2-(trimethylsilyl)ethyl 5-hydroxy-4-methoxy-2-nitrobenzoate (33)

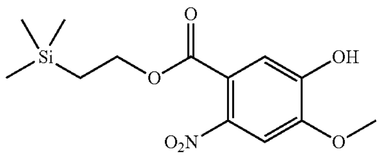

To a solution of 11 (5000 mg, 23.46 mmol) and triphenylphosphine (12.31 g, 46.92 mmol) in dry THF (150 mL) was added 2-(trimethylsilyl)ethanol (5.04 mL, 35.19 mmol) and diisopropyl azodicarboxylate (6.93 mL, 35.19 mmol) dropwise in an ice-bath. The resulting solution was stirred RT under $N_2$ for 7 h. The reaction mixture was suspended in $H_2O$ (150 mL) and then extracted with EtOAc (3×150 mL). The organic layer was collected and dried over anhydrous $MgSO_4$, filtered and concentrated in vacuo. The residue was purified by silica gel chromatography (EtOAc/n-hexane=1:9) to afford 33 (2.03 g, 29%). $^1H$ NMR (300 MHz, $CDCl_3$) δ 7.49 (s, 1H), 7.11 (s, 1H), 4.38 (m, 2H), 3.99 (s, 3H), 1.07 (m, 2H), 0.03 (s, 9H).

2-(trimethylsilyl)ethyl 5-(3-chloropropoxy)-4-methoxy-2-nitrobenzoate (34)

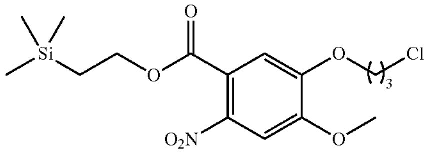

Following the procedure described for compound 2, reaction of 33 (2.43 g, 7.76 mmol) and $K_2CO_3$ (2.15 g, 15.53 mmol) in DMF (150 ml) was added 1-bromo-3-chloropropane (0.921 mL, 9.32 mmol). The resulting solution was heated to 100° C. under $N_2$ to afford 34 (2.88 g, 95%). $^1H$ NMR (300 MHz, $CDCl_3$) δ 7.42 (s, 1H), 7.08 (s, 1H), 4.38 (m, 2H), 4.24 (m, 2H), 3.67 (m, 2H), 2.34 (m 2H), 1.08 (m, 2H), 0.04 (s, 9H).

2-(trimethylsilyl)ethyl 5-(3-(1,3-dioxoisoindolin-2-yl)propoxy)-4-methoxy-2-nitrobenzoate (35)

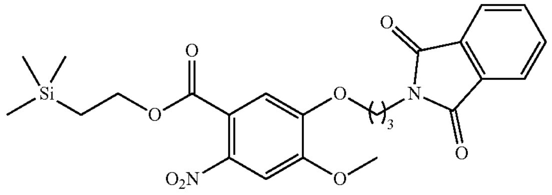

Following the procedure described for compound 2, reaction of 34 (2.88 g, 7.37 mmol) and $K_2CO_3$ (2.04 g, 14.75 mmol) in DMF (100 mL) was added phthalimide potassium salt (1.64 g, 8.85 mmol). The resulting solution was heated to 100° C. under $N_2$ to afford 35 (3.42 g, 93%). $^1H$ NMR (300 MHz, $CDCl_3$) δ 7.81 (m, 2H), 7.70 (m, 2H), 7.32 (s, 1H), 6.99 (s, 1H), 4.36 (m, 2H), 4.14 (q, J=5.5 Hz, 2H), 3.90 (t, J=6.4 Hz, 2H), 3.66 (s, 3H), 2.25 (m, 2H), 1.06 (m, 2H), 0.03 (s, 9H).

2-(trimethylsilyl)ethyl 5-(3-aminopropoxy)-4-methoxy-2-nitrobenzoate (36)

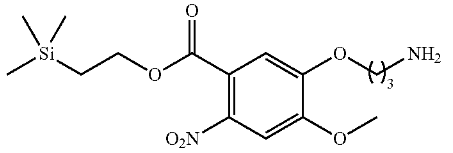

To a solution of 35 (1.50 g, 3.00 mmol) in MeOH (150 mL) was added hydrazine monohydrate (1.45 mL, 29.97 mmol) dropwise. The resulting solution was reflux and stirred under $N_2$ for 24 h. The reaction mixture was concentrated in vacuo and suspended in $H_2O$ (150 mL) and then extracted with EtOAc (3×150 mL). The combined organic layer was dried over $MgSO_4$, filtered and concentrated in vacuo. The residue was purified by silica gel chromatography ($MeOH/CH_2Cl_2$=1:99) to afford 36 (140 mg, 13%), $^1H$ NMR (300 MHz, $CDCl_3$) δ 7.45 (s, 1H), 6.52 (s, 1H), 5.38 (s, 2H), 4.39 (m, 2H), 3.91 (s, 3H), 3.79 (t, J=5.8 Hz, 2H), 3.37 (m, 2H), 1.90 (m, 2H), 1.08 (m, 2H), 0.03 (s, 9H).

2-(trimethylsilyl)ethyl 5-(3-benzamidopropoxy)-4-methoxy-2-nitrobenzoate (37)

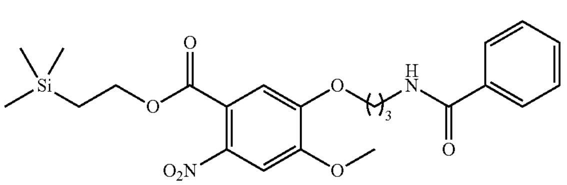

To a solution of 36 (140 mg, 0.38 mmol) in dry $CH_2Cl_2$ (10 mL) was added pyridine (0.122 mL, 1.51 mmol) and benzoyl chloride (0.131 mL, 1.13 mmol) dropwise. The resulting solution was stirred at RT under $N_2$ for 12 h. The reaction mixture was suspended in $H_2O$ (50 mL) and then extracted with $CH_2Cl_2$ (3×50 mL). The combined organic layer was dried over $MgSO_4$, filtered and concentrated in vacuo. The residue was purified by silica gel chromatography (EtOAc/n-hexane=1:4) to afford 37 (177 mg, 99%). $^1H$ NMR (300 MHz, $CDCl_3$) δ 8.02 (d, J=7.1 Hz, 2H), 7.57 (tt, J=7.4, 1.2 Hz, 1H), 7.45 (m, 3H), 6.54 (s, 1H), 5.24 (s, 1H), 4.45 (t, J=5.9 Hz, 2H), 4.38 (m, 2H), 3.85 (s, 3H), 3.42 (q, J=6.3 Hz, 2H), 2.13 (m, 2H), 1.08 (m, 2H), 0.03 (s, 9H).

2-(trimethylsilyl)ethyl 2-amino-5-(3-benzamidopropoxy)-4-methoxybenzoate (38)

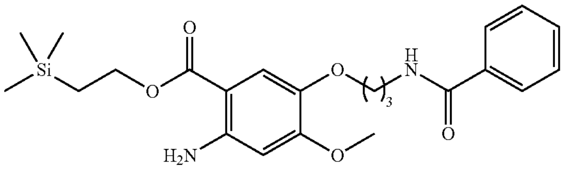

To a solution of 37 (180 mg, 0.38 mmol) in HOAc/THF=1:4 (20 mL) was added Zn (248 mg, 3.79 mmol) and the mixture was stirred at RT under $N_2$ for 24 h. The reaction mixture was filtered with celite. The residue was extracted with EtOAc (50 mL) and $NaHCO_3$ (3×50 mL). The combined organic layer was dried over $MgSO_4$, filtered and concentrated in vacuo. The residue was purified by silica gel chromatography (EtOAc/n-hexane=1:3) to afford 38 (158 mg, 94%). $^1H$ NMR (300 MHz, $CDCl_3$) δ 8.04 (m, 2H), 7.55 (m, 1H), 7.42 (m, 2H), 7.06 (s, 1H), 6.08 (s, 1H), 4.45 (t, J=6.2 Hz, 2H), 4.32 (m, 2H), 3.77 (s, 3H), 3.26 (t, J=6.8 Hz, 2H), 2.11 (tt, J=6.2, 6.8 Hz, 2H), 1.07 (m, 2H), 0.05 (s, 9H).

2-(trimethylsilyl)ethyl 4-methoxy-2-propiolamido-5-(3-(N-propioloylbenzamido)propoxy)benzoate (39)

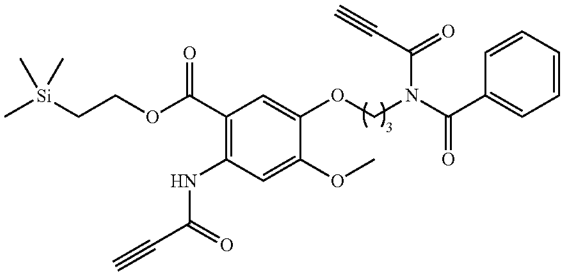

Following the procedure described for compound 4, reaction of 38 (125 mg, 0.28 mmol) in dry $CH_2Cl_2$ (10 mL) was added propiolic acid (0.037 mL, 0.56 mmol) and N, N'-dicyclohexylcarbodiimide (116 mg, 0.56 mmol) in dry $CH_2Cl_2$ (5 mL) dropwise in an ice-bath to afford 39 (149 mg, 97%). $^1H$ NMR (300 MHz, $CDCl_3$) δ 11.82 (s, 1H), 8.38 (s, 1H), 7.94 (dd, J=8.4, 1.4 Hz, 2H), 7.87 (s, 1H), 7.52 (m, 1H), 7.40 (m, 2H), 4.37 (m, 2H), 3.93 (m, 4H), 3.72 (m, 1H), 2.97 (s, 1H), 2.68 (s, 1H), 1.99 (m, 2H), 1.12 (m, 2H), 0.06 (s, 9H).

4-methoxy-2-propiolamido-5-(3-(N-propioloylbenzamido)propoxy)benzoic acid (40)

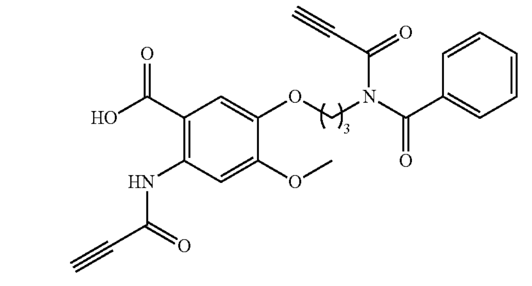

To a solution of 39 (75 mg, (0.14 mmol) in dry THF (3 mL) was added TBAF (1M in THF, 0.75 mL, 0.75 nmol) dropwise at RT. The resulting solution was stirred under $N_2$ for 5 h. The reaction mixture was suspended in 1 N $HCl_{(aq)}$ (50 mL) and extracted with EtOAc (3×50 mL). The combined organic layer was dried over $MgSO_4$, filtered and concentrated in vacuo. The residue was purified by silica gel chromatography ($MeOH/CH_2Cl_2$=3:97) to afford 40 (46 mg, 75%). $^1H$ NMR (300 MHz, DMSO) δ 11.57 (s, 1H), 8.40 (s, 1H), 7.94 (m, 2H), 7.52 (m, 1H), 7.40 (m, 2H), 4.35 (t, J=6.3 Hz, 2H), 3.95 (m, 4H), 3.72 (m, 1H), 2.99 (s, 1H), 2.71 (s, 1H), 2.00 (m, 2H).

Scheme 13

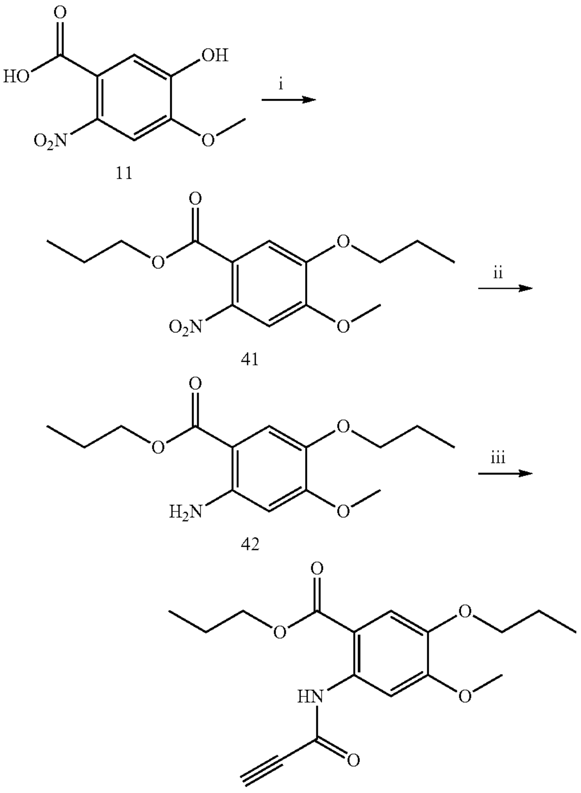

11

41

42

43

Reagents and conditions: (i) propyl bromide, $K_2CO_3$, DMF, RT; (ii) Zn, AcOH, 50° C.; (iii) propiolic acid, DCC, $CH_2Cl_2$, 0° C.

propyl 4-methoxy-2-nitro-5-propoxybenzoate (41)

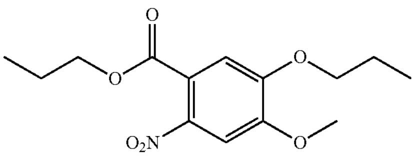

Following, the procedure described for compound 2, reaction of 11 (2.13 g, 10.00 mmol) and $K_2CO_3$ (5.52 g, 39.92 mmol) in DMF (50 mL) was added 1-bromopropane (3.63 mL, 40.00 mmol). The resulting solution was heated to 100° C. under $N_2$ to afford 41 (2.80 g, 94%). $^1$H NMR (500 MHz, $CDCl_3$) δ 7.41 (s, 1H), 7.04 (s, 1H), 4.24 (t, J=6.7 Hz, 2H), 4.04 (t, J=6.7 Hz, 2H), 4.92 (s, 3H), 1.87 (dt, J=6.7, 7.4 Hz, 2H), 1.71 (dt, J=6.7, 7.4 Hz, 2H), 1.03 (t, J=7.4 Hz, 3H), 0.95 (t, J=7.4 Hz, 3H).

propyl 2-amino-4-methoxy-5-propoxybenzoate (42)

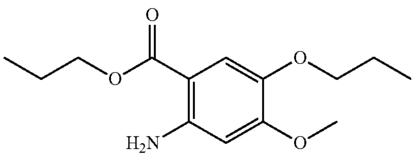 [SMILES: CCCOC(=O)c1cc(OCCC)c(OC)cc1[N+](=O)[O-]]

To a solution of 41 (2.70 g, 9.08 mmol) in HOAc (20 mL) was added Zn (5.94 g, 90.81 mmol) and the mixture was stirred at RT under $N_2$ for 48 h. The reaction mixture was filtered with celite. The residue was extracted with EtOAc (150 mL) and $NaHCO_3$ (3×150 mL). The combined organic layer was dried over $MgSO_4$, filtered and concentrated in vacuo. The residue was purified by silica gel chromatography (EtOAc/n-hexane=1:7) to afford 27 (1.90 g, 78%). $^1$H NMR (500 MHz, $CDCl_3$) δ 7.33 (s, 1H), 6.11 (s, 1H), 4.19 (t, J=6.7 Hz, 2H), 3.87 (t, J=6.7 Hz, 2H), 3.32 (s, 3H), 1.77 (m, 4H), 1.00 (m, 6H).

propyl 4-methoxy-2-propiolamido-5-propoxybenzoate (43)

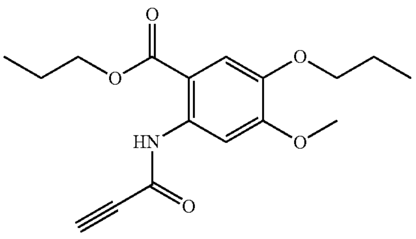 [SMILES: C#CC(=O)Nc1cc(OC)c(OCCC)cc1C(=O)OCCC]

Following the procedure described for compound 4, reaction of 41 (440 mg, 1.74 mmol) in dry $CH_2Cl_2$ (10 mL) was added propiolic acid (0.183 mL, 2.61 mmol) and N, N'-dicyclohexylcarbodiimide (466 mg, 2.26 mmol) in dry $CH_2Cl_2$ (5 mL) dropwise in an ice-bath to afford 43 (202 mg, 38%). $^1$H NMR (300 MHz, $CDCl_3$) δ 11.56 (s, 1H), 8.30 (s, 1H), 7.46 (s, 1H), 4.26 (t, J=6.7 Hz, 2H), 3.95 (t, J=6.8 Hz, 2H), 3.91 (s, 3H), 1.81 (m, 4H), 1.02 (m, 6H).

Scheme 14

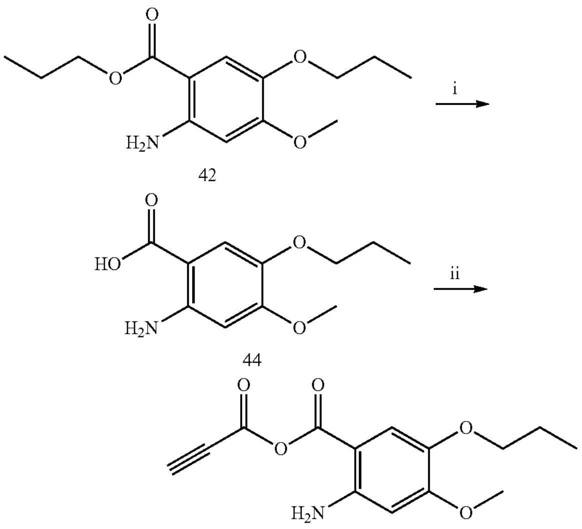

42
44
45

Reagents and conditions: (i) LiOH, MeOH, 70° C.; (ii) propiolic acid, DCC, $CH_2Cl_2$, 0° C.

2-amino-4-methoxy-5-propoxybenzoic acid (44)

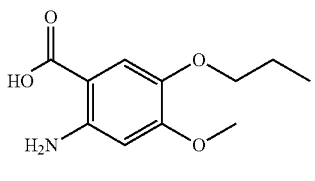

Following the procedure described for compound 15, reaction of 42 (500 mg, 1.87 mmol) and LiOH (790 mg, 18.70 mmol) in MeOH (20 ml was heated to 70° C. under $N_2$ to afford 44 (310 mg, 75%). $^1$H NMR (500 MHz, $CDCl_3$) δ 7.35 (s, 1H), 6.11 (s, 1H), 3.89 (t, J=6.8 Hz, 2H), 3.84 (s, 3H), 1.81 (m, 2H), 1.01 (t, J=7.5 Hz, 3H).

2-amino-4-methoxy-5-propoxybenzoic propiolic anhydride (45)

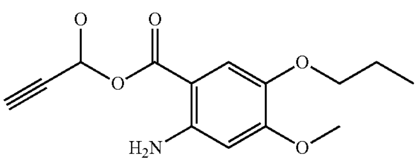

Following the procedure described for compound 4, reaction of 44 (225 mg, 1.00 mmol) in dry $CH_2Cl_2$ (10 mL) was added propiolic add (0.092 mL, 1.50 mmol) and N, N'-dicyclohexylcarbodiimide (267 mg, 1.29 mmol) in dry $CH_2Cl_2$ (5 mL) dropwise in an ice-bath to afford 45 (5 mg, 2%). $^1$H NMR (300 MHz, $CDCl_3$) δ 7.49 (s, 1H), 7.02 (s, 1H), 4.06 (t, J=6.7 Hz, 2H), 3.96 (s, 3H), 3.20 (s, 1H), 1.89 (m, 2H), 1.05 (t, J=7.4 Hz, 3H).

Scheme 15

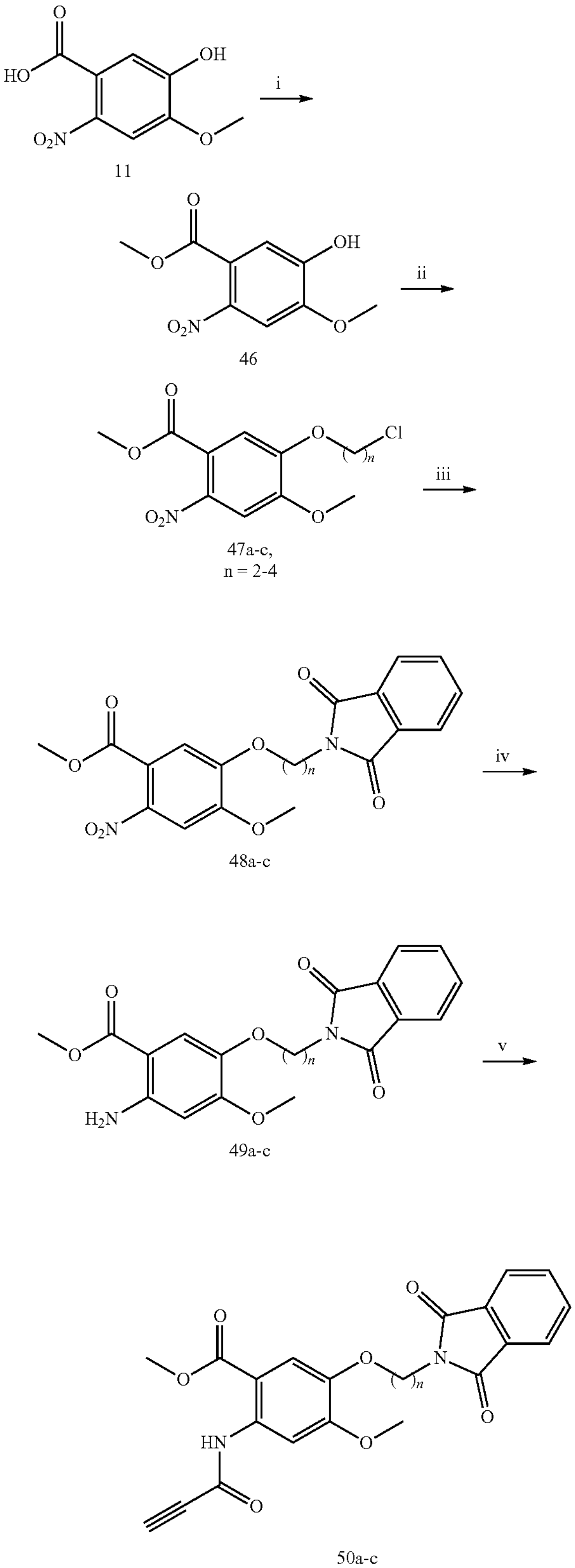

11

46

47a-c,
n = 2-4

48a-c 49a-c 50a-c

Reagents and conditions: (i) HCl, MeOH, 60° C.; (ii) $Cl(CH_2)nBr$, $K_2CO_3$, DMF, 100° C.; (iii) potassium phthalimide, $K_2CO_3$, DMF, 100° C.; (iv) Zn, AcOH, THF, RT; (v) propiolic acid, DCC, $CH_2Cl_2$, 0° C.

methyl 5-hydroxy-4-methoxy-2-nitrobenzoate (46)

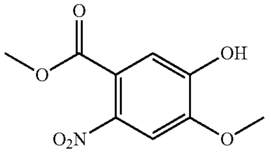

To a solution of 11 (20.00 g, 93.83 mmol) in MeOH (300 mL) was added 12 N $HCl_{(aq)}$ (30 mL) dropwise. The resulting solution was reflux under $N_2$ for 72 h. The reaction mixture was concentrated in vacuo. The residue was washed with $H_2O$ (100 mL) and filtered to afford 46 (19.05 g, 89%) as white solid. $^1H$ NMR (300 MHz, $CDCl_3$) δ 7.50 (s, 1H), 7.12 (S, 1H), 6.17 (s, 1H), 3.99 (s, 3H), 3.88 (s, 3H).

methyl 5-(2-chloroethoxy)-4-methoxy-2-nitrobenzoate (47a)

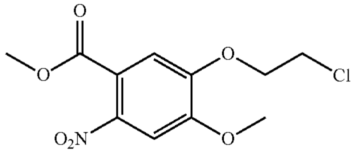 [SMILES: COC(=O)c1cc(OCCCl)c(OC)cc1[N+](=O)[O-]]

Following the procedure described for compound 2, reaction of 46 (1.00 g, 4.40 mmol) and $K_2CO_3$ (1.21 g, 8.80 mmol) in DMF (50 mL) was added 1-bromo-2-chloroethane (0.44 mL, 5.28 mmol). The resulting solution was heated to 100° C. under $N_2$ to afford 47a (414 mg, 32%). $^1H$ NMR (300 MHz, $CDCl_3$) δ 7.24 (s, 1H), 7.09 (s, 1H), 4.34 (t, J=5.9 Hz, 2H), 3.95 (s, 3H), 3.88 (s, 3H), 3.86 (t, J=5.9 Hz, 2H).

methyl 5-(3-chloropropoxy)-4-methoxy-2-nitrobenzoate (47b)

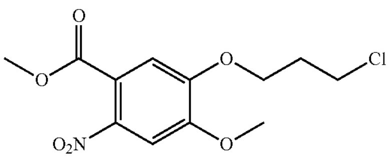 [SMILES: COC(=O)c1cc(OCCCCl)c(OC)cc1[N+](=O)[O-]]

Following the procedure described for compound 2, reaction of 11 (19.05 g, 83.86 mmol), (23.18 g, 167.71 mmol) and 1-bromo-3-chloropropane (12.44 mL, 125.79 mmol) DMF (350 mL) was heated to 100° C. under $N_2$ to afford 47b (21.45 g, 84%). $^1H$ NMR (300 MHz, $CDCl_3$) δ 7.43 (1, sH), 7.09 (s, 1H), 4.24 (t, J=5.9 Hz, 2H), 3.93 (s, 3H), 3.89 (s, 3H), 3.74 (t, J=6.1 Hz, 2H), 2.30 (tt, J=5.9, 6.1 Hz, 2H).

methyl 5-(4-chlorabutoxy)-4-methoxy-2-nitrobenzoate (47c)

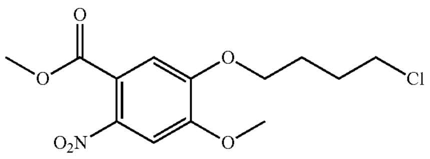 [SMILES: COC(=O)c1cc(OCCCCCl)c(OC)cc1[N+](=O)[O-]]

Following the procedure described for compound 2, reaction of 11 (1.00 g, 83.86 mmol), $K_2CO_3$ (1.21 g, 8.80 mmol) and 1-bromo-4-chlorobutane (0.61 mL, 5.28 mmol) in DMF (50 mL) was heated to 100° C. under $N_2$ to afford 47c (1.09 g, 78%). $^1H$ NMR (300 MHz, $CDCl_3$) δ 7.43 (s, 1H), 7.04 (s, 1H), 4.12 (t, J=5.9 Hz, 2H), 3.93 (s, 3H), 3.88 (s, 3H), 3.61 (t, J=6.2 Hz, 3H), 1.99 (m, 4H).

methyl 5-(2-(1,3-dioxoisoindolin-2-yl)ethoxy)-4-methoxy-2-nitrobenzoate (48a)

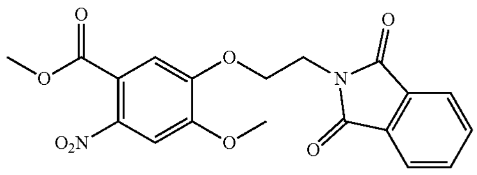 [SMILES: COC(=O)c1cc(OCCN2C(=O)c3ccccc3C2=O)c(OC)cc1[N+](=O)[O-]]

Following the procedure described for compound 2, reaction of 47a (390 mg, 1.35 mmol), $K_2CO_3$ (372 mg, 2.69 mmol) and phthalimide potassium salt (299 mg, 1.61 mmol) m DMF (50 mL) was heated to 100° C. under $N_2$ to afford 48a (463 mg, 86%) as white solid. $^1H$ NMR (300 MHz, $CDCl_3$) δ 7.85 (m, 2H), 7.72 (m, 2H), 7.36 (s, 1H), 7.10 (s, 1H), 4.35 (t, J=5.8 Hz, 2H), 4.14 (t, J=5.9 Hz, 2H), 3.86 (s, 3H), 3.85 (s, 3H).

methyl 5-(3-(1,3-dioxoisoindolin-2-yl)propoxy)-4-methoxy-2-nitrobenzoate (48b)

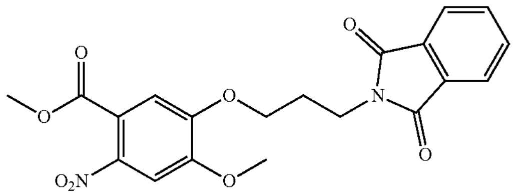 [SMILES: COC(=O)c1cc(OCCCN2C(=O)c3ccccc3C2=O)c(OC)cc1[N+](=O)[O-]]

Following the procedure described for compound 2, reaction of 47b (21.45 g, 70.63 mmol), $K_2CO_3$ (19.52 g, 141.26 mmol) and phthalimide potassium salt (19.62 g, 105.95 mmol) int DMF (300 mL) was heated to 100° C. under $N_2$ to afford 48b (29.00 g, 99%) as white solid. $^1H$ NMR (300 MHz, $CDCl_3$) δ 7.84 (m, 2H), 7.72 (m, 2H), 7.33 (s, 1H), 7.00 (s, 1H), 4.15 (t, J=5.9 Hz, 2H), 3.90 (t, J=6.4 Hz, 2H), 3.87 (s, 3H), 3.67 (s, 3H), 2.26 (tt, 5.9, 6.4 Hz, 2H).

methyl 5-(4-(1,3-dioxoisoindolin-2-yl)butoxy)-4-methoxy-2-nitrobenzoate (48c)

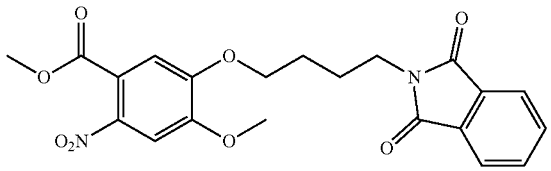 [SMILES: COC(=O)c1cc(OCCCCN2C(=O)c3ccccc3C2=O)c(OC)cc1[N+](=O)[O-]]

Following the procedure described for compound 2, reaction of 47c (950 mg, 2.99 mmol), $K_2CO_3$ (826 mg, 5.98 mmol) and phthalimide potassium salt (665 mg, 3.59 mmol) in DMF (50 mL) was heated to 100° C. under $N_2$ to afford 48c (1064 mg, 83%) as white solid. $^1H$ NMR (300 MHz, $CDCl_3$) δ 7.82 (m, 2H), 7.70 (m, 2H), 7.40 (s, 1H), 7.03 (s, 1H), 4.11 (t, J=5.9 Hz, 2H), 3.91 (s, 3H), 3.88 (s, 3H), 3.76 (t, J=6.2 Hz, 3H), 1.89 (m, 4H).

methyl 2-amino-5-(2-(1,3-dioxoisoindolin-2yl) ethoxy-4-methoxybenzoate (49a)

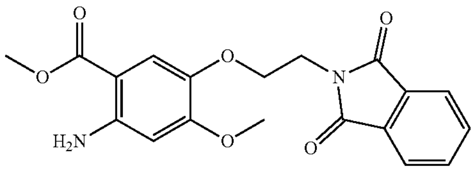 [SMILES: COC(=O)c1cc(OCCN2C(=O)c3ccccc3C2=O)c(OC)cc1N]

Following the procedure described for 3, reaction of 48a (100 mg, 0.25 mmol), 10% Pd/C (10 mg) in EtOH/EtOAc=1:1 (10 mL) under $H_2$ afforded 49a (74 mg, 80%), $^1H$ NMR (300 MHz, $CDCl_3$) δ 7.84 (m, 2H), 7.70 (m, 2H), 7.35 (s, 1H), 6.03 (s, 1H), 5.55 (s, 2H), 4.16 (t, J=5.8 Hz, 2H), 4.06 (t, J=5.9 Hz, 2H), 3.79 (s, 3H), 3.67 (s, 3H).

methyl 2-amino-5-(3-(1,3-dioxoisoindolin-2-yl) propoxy-4-methoxybenzoate (49b)

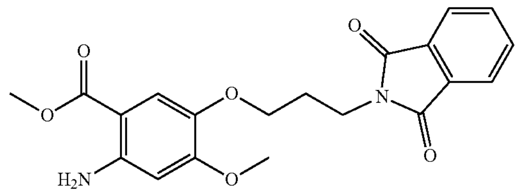 [SMILES: COC(=O)c1cc(OCCCN2C(=O)c3ccccc3C2=O)c(OC)cc1N]

Following the procedure described for 3, reaction of 48b (100 mg, 0.24 mmol), 10% Pd/C (10 mg) in EtOH/EtOAc=1:1 (10 mL) under $H_2$ afforded 49b (76 mg, 82%), NMR (300 MHz, $CDCl_3$) δ 7.81 (m, 2H), 7.68 (m, 2H), 7.30 (s, 1H), 6.05 (s, 1H), 5.54 (s, 2H), 3.99 (t, J=6.2 Hz, 2H), 3.88 (t, J=6.9 Hz, 2H), 3.80 (s, 3H) 3.68 (s, 3H), 2.16 (tt, J=6.2, 6.9 Hz, 2H).

methyl 2-amino-5-(4-(1,3-dioxoisoindolin-2-yl)butoxy)-4-methoxybenzoate (49c)

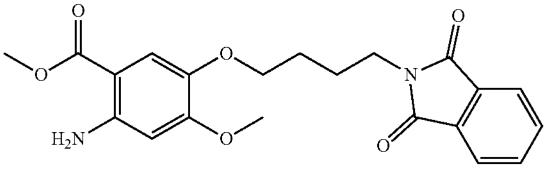

Following the procedure described for 3, reaction of 48c (100 mg, 0.23 mmol), 10% pd/C (10 mg) in EtOH/EtOAc=1:1 (10 mL) under $H_2$ afforded 49c (74 mg, 80%). $^1H$ NMR (300 MHz, $CDCl_3$) δ 7.80 (m, 2H), 7.68 (m, 2H), 7.28 (s, 1H), 6.08 (s, 1H), 5.55 (s, 2H), 3.93 (t, J=6.0 Hz, 2H), 3.80 (s, 2H), 3.79 (s, 3H), 3.74 (t, 6.7 Hz, 3H), 1.83 (m, 4H).

methyl 5-(2-(1,3-dioxoisoindolin-2-yl)ethoxy)-4-methoxy-2-propiolamidobenzoate (50a)

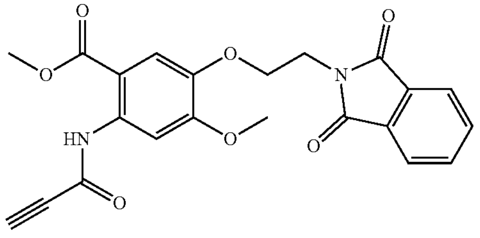 [SMILES: C#CC(=O)Nc1cc(OC)c(OCCN2C(=O)c3ccccc3C2=O)cc1C(=O)OC]

Following the procedure described for compound 4, reaction of 49a (50 mg, 0.14 mmol), propiolic acid (0.013 mL, 0.20 mmol) and N, N'-dicyclohexylcarbodiimide (42 mg, 0.20 mmol) in $CH_2Cl_2$ (15 mL) under $N_2$ afforded 50a (57 mg 99%). $^1H$ NMR (500 MHz, $CDCl_3$) δ 11.52 (s, 1H), 8.25 (s, 1H), 7.84 (dd, J=3.1 Hz, 2H), 7.71 (dd, J=5.5, 3.1 Hz, 2H), 7.51 (s, 1H), 4.25 (t, J=5.9 Hz, 2H) 4.10 (t, J=5.9 Hz, 2H), 3.88 (s, 3H), 3.79 (s, 3H) 2.90 (s, 2H).

methyl 5-(3-(1,3-dioxoisoindolin-2-yl)propoxy)-4-methoxy-2-propiolamidobenzoate (50b)

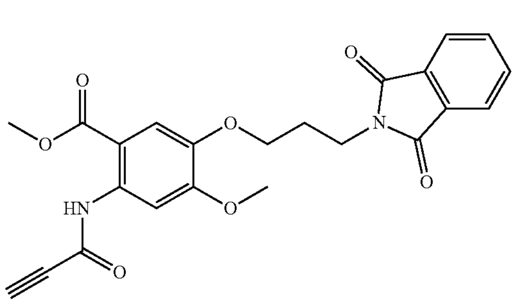 [SMILES: C#CC(=O)Nc1cc(OC)c(OCCCN2C(=O)c3ccccc3C2=O)cc1C(=O)OC]

Following the procedure described for compound 4, reaction of 49b (50 mg, 0.13 mmol), propiolic acid (0.012 mL, 0.20 mmol) and N, N'-dicyclohexylcarbodiimide (40 mg, 020 mmol) in $CH_2Cl_2$ (15 mL) under $N_2$ afforded 50b (34 mg, 60%). $^1H$ NMR (500 MHz, $CDCl_3$) δ 11.53 (s, 1H), 8.22 (s, 1H), 7.80 (dd, 5.4, 3.1 Hz, 2H), 7.69 (dd, 5.4, 3.0 Hz, 2H), 7.43 (s, 1H), 4.08 (t, J=6.0 Hz, 2H), 3.90 (m, 5H), 3.68 (s, 3H), 2.91 (s, 1H), 2.21 (tt, J=6.0, 6.6 Hz, 2H).

methyl 5-(4-(1,3-dioxoisoindolin-2-yl)butoxy)-4-methoxy-2-propiolamidobenzoate (50c)

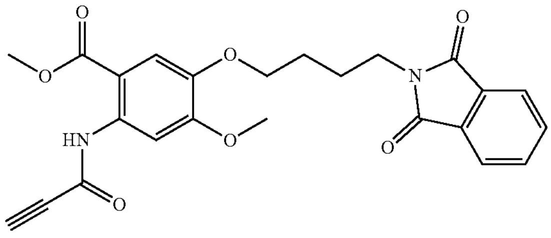 [SMILES: C#CC(=O)Nc1cc(OC)c(OCCCCN2C(=O)c3ccccc3C2=O)cc1C(=O)OC]

Following the procedure described for compound 4, reaction of 49c (50 mg, 0.13 mmol), propiolic acid (0.012 mL, 0.19 mmol) and N, N'-dicyclohexylcarbodiimide (39 mg, 0.19 mmol) in $CH_2Cl_2$ (15 mL) under $N_2$ afforded 50c (56 mg, 99%). $^1H$ NMR (500 MHz, $CDCl_3$) δ 11.52 (s, 1H), 8.28 (s, 1H), 7.81 (dd, J=5.3, 3.0 Hz, 2H), 7.69 (dd, J=5.5, 3.0 Hz, 2H), 7.43 (s, 1H), 4.02 (t, J=6.0 Hz, 2H), 3.89 (m, 6H), 3.75 (t, J=6.6 Hz, 2H), 2.91 (s, 1H), 1.87 (m, 4H).

Scheme 16

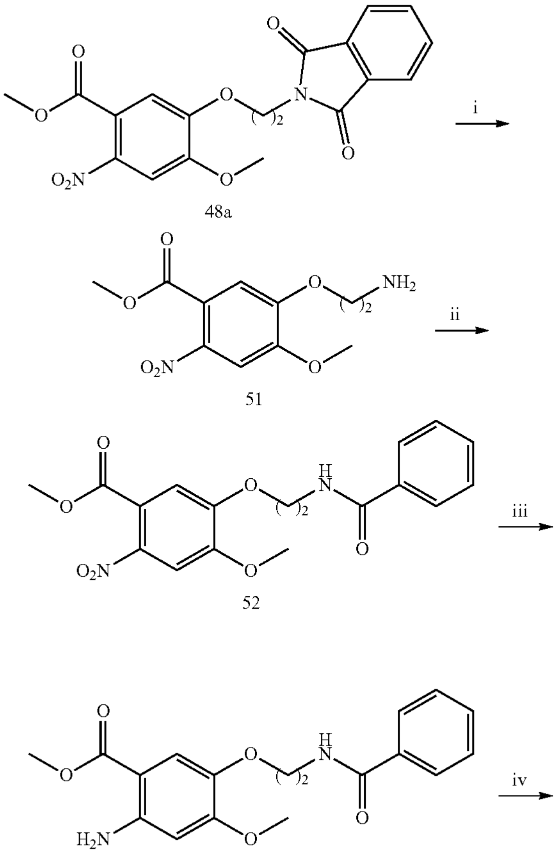

-continued

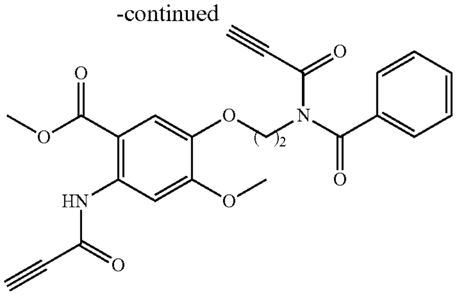

54

Reagents and conditions: (i) $NH_2NH_2$—$H_2O$, MeOH, 60° C.; (ii) RCOCl, pyridine, $CH_2Cl_2$, RT; (iii) Zn, AcOH, THF, RT; (iv) propiolic acid, DCC, $CH_2Cl_2$, 0° C.

methyl 5-(2-aminoethoxy)-4-methoxy-2-nitrobenzoate (51)

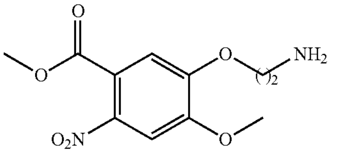 [SMILES: COC(=O)c1cc(OCN)c(OC)cc1[N+](=O)[O-]]

To a solution of 48a (250 mg, 0.62 mmol) in MeOH (25 mL) was added hydrazine monohydrate (0.303 mL, 6.24 mmol) dropwise. The resulting solution was reflux and stirred under $N_2$ for 4 h. The reaction mixture was concentrated in vacuo and suspended in $H_2O$ (150 ML) and then extracted with EtOAc (3×150 mL). The combined organic layer was dried over $MgSO_4$, filtered and concentrated in vacuo. The residue was purified by silica gel chromatography (MeOH/$CH_2Cl_2$=1:99) to afford 51 (121 mg, 72%) as brown oil, $^1$H NMR (300 MHz, $CDCl_3$) δ 7.47 (s, 1H), 6.55 (s, 1H), 5.36 (s, 2H), 3.93 (2, 3H), 3.89 (m, 5H), 3.39 (m, 2H).

methyl 5-(2-benzamidoethoxy)-4-methoxy-2-nitrobenzoate (52)

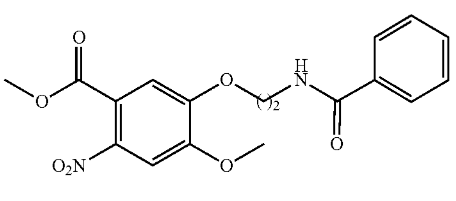

To a solution of 51 (50 mg, 0.19 mmol) in dry $CH_2Cl_2$ (10 mL) was added pyridine (0.060 mL, 0.74 mmol) and benzoyl chloride (0.065 mL, 0.56 mmol) dropwise. The resulting solution was stirred at RT under $N_2$ for 2.5 h. The reaction mixture was suspended in $H_2O$ (50 mL) and then extracted with $CH_2Cl_2$ (3×50 mL). The combined organic layer was dried over $MgSO_4$, filtered and concentrated in vacuo. The residue was purified by silica gel chromatography EtOAc/n-hexane=1:5) to afford 52 (65 mg, 94%). $^1$H NMR (300 MHz, $CDCl_3$) δ 8.00 (d, 7.2 Hz, 2H), 7.56 (m, 1H), 7.44 (m, 3H), 6.66 (s, 1H), 5.34 (s, 1H), 4.54 (t, 5.4 Hz, 2H), 4.10 (q, J=7.2 Hz, 2H), 3.93 (s, 3H), 3.89 (s, 3H), 3.3.65 (m, 2H).

methyl 2-amino-5-(2-benzamidoethoxy)-4-methoxybenzoate (53)

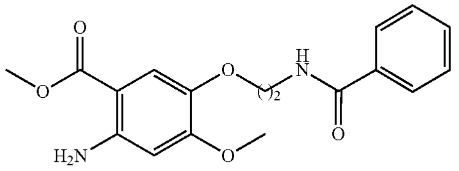 [SMILES: COC(=O)c1cc(OCNC(=O)c2ccccc2)c(OC)cc1[N+](=O)[O-]]

Following the procedure described for compound 38, reaction of 52 (63 mg, 0.17 mmol) its HOAc/THF=1:4 (10 mL) was added Zn (253 mg, 3.86 mmol) and the mixture was stirred at RT under $N_2$ to afford 53 (45 mg, 78%). $^1$H NMR (300 MHz, $CDCl_3$) δ 8.03 (dd, 8.3, 1.4 Hz, 2H), 7.53 (tt, J=3.7, 1.6 Hz, 2H), 7.42 (t, J=7.5 Hz, 2H), 7.12 (s, 1H), 6.09 (s, 1H), 5.38 (s, 2H), 4.52 (t, J=5.2 Hz, 2H), 3.81 (s, 3H), 3.80 (s, 3H), 3.50 (t, J=5.4 Hz, 2H).

methyl 4-methoxy-2-propiolamido-5-(2-(N-propioloylbenzamido)ethoxy)benzoate) (54)

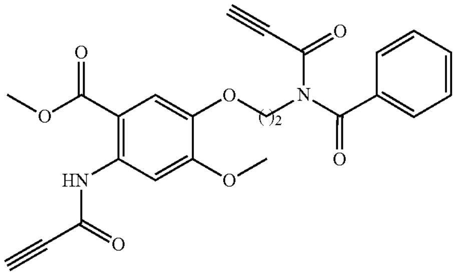

Following the procedure described for compound 4, reaction of 53 (40 mg, 0.12 mmol) in dry $CH_2Cl_2$ (10 mL) was added propiolic acid (0.011 mL, 0.17 mmol) and N, N'-dicyclohexylcarbodiimide (36 mg, 0.17 mmol) in dry $CH_2Cl_2$ (5 mL) dropwise in an ice-bath to afford 54 (49 mg, 94%), $^1$H NMR (300 MHz, $CDCl_2$) δ 11.70 (s, 1H), 8.34 (s, 1H), 7.90 (s, 1H), 7.83 (m, 2H), 7.51 (tt, J=7.4, 1.6 Hz, 2H), 7.35 (m, 2H), 4.44 (m, 2H), 4.25 (m, 1H), 3.89 (m, 1H), 3.83 (s, 3H), 3.76 (s, 3H), 2.98 (s, 2H), 2.71 (s, 1H).

Scheme 17

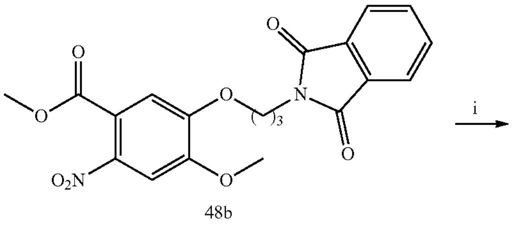

48b

-continued

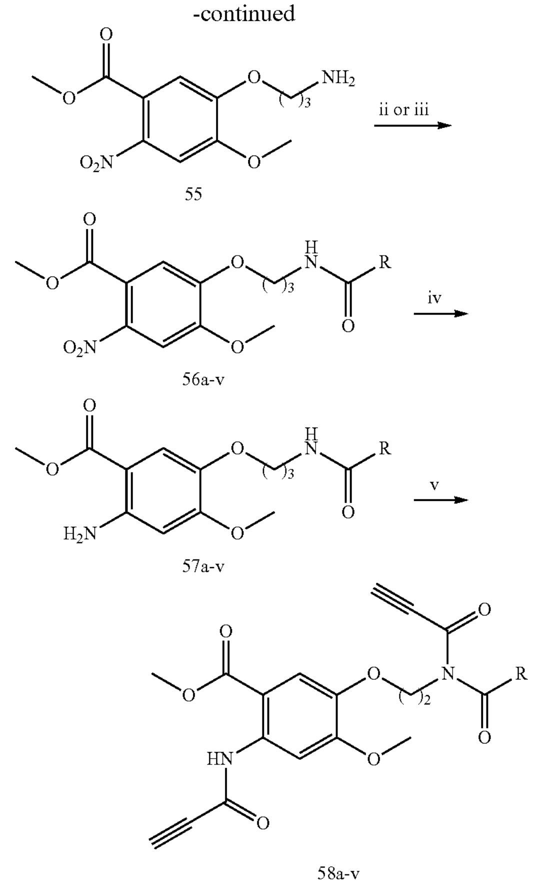

55

56a-v 57a-v 58a-v a: R = Phenyl
b: R = 2-F-Ph
c: R = 3-F-Ph
d: R = 4-F-Ph
e: R = 2,6-Difluoro-Ph
f: R = 2,6-DiOMe-Ph
g: R = 3-OMe-Phe
h: R = 4-OMe-Ph
i: R = Bn
j: R = 2-F-Bn
k: R = 3-F-Bn
l: R = 4-F-Bn
m: R = 2-OMe-Bn
n: R = 3-OMe-Bn
o: R = 4-OMe-Bn
p: R = 3,4,5-TrioMe-Bn
q: R = 2-C-Bn
r: R = 3-Cl-Bn
s: R = 2-$CF_3$-Bn
t: R = 3-$CF_3$-Bn
u: R = 4-$CF_3$-Bn
v:

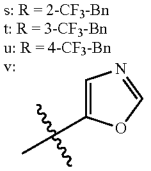

Reagents and conditions: (i) $NH_2NH_2$—$H_2O$, MeOH, 60° C.; (ii) RCOCl, pyridine, $CH_2Cl_2$, RT; (iii) $RCO_2H$ DMAP, DCC, $CH_2Cl_2$, RT; (iv) Zn, AcOH, THF, RT; (v) propiolic acid, DCC, $CH_2Cl_2$, 0° C.

methyl 5-(3-aminopropoxy)-4-methoxy-2-nitrobenzoate (55)

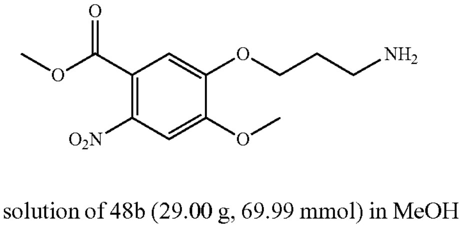

To a solution of 48b (29.00 g, 69.99 mmol) in MeOH (500 mL) was added hydrazine monohydrate (33.95 mL, 699.86 mmol) dropwise. The resulting solution was reflux and stirred under $N_2$ for 24 h. The reaction mixture was concentrated in vacuo and suspended in $H_2O$ (150 mL) and then extracted with EtOAc (3×150 mL). The combined organic layer was dried over $MgSO_4$, filtered and concentrated in vacuo. The residue was purified by silica gel chromatography ($MeOH/CH_2Cl_2$=1:99) to afford 55 (3.25 g, 16%) as brown oil. $^1H$ NMR (300 MHz, $CDCl_3$) δ 7.46 (s, 1H), 6.53 (s, 1H), 5.38 (s, 2H), 3.92 (2, 3H), 3.89 (s, 3H), 3.80 (t, J=5.7 Hz, 2H), 3.38 (dt, J=5.6, 6.6 Hz, 2H), 1.91 (tt, J=5.7, 6.5 Hz, 2H).

methyl 5-(3-benzamidopropoxy)-4-methoxy-2-nitrobenzoate (56a)

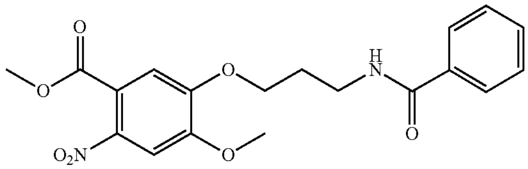

To a solution of 55 (100 mg, 0.35 mmol) as dry $CH_2Cl_2$ (10 mL) was added pyridine (0.113 mL, 1.41 mmol) and benzoyl chloride (0.113 mL, 1.41 mmol) dropwise. The resulting solution was stirred at RT under $N_2$ for 2.5 h. The reaction mixture was suspended in $H_2O$ (50 mL) and then extracted with $CH_2Cl_2$ (3×50 mL). The combined organic layer was dried over $MgSO_4$, filtered and concentrated in vacuo. The residue was purified by silica gel chromatography (EtOAc/n-hexane=1:5) to afford 56a (124 mg, 91%). $^1H$ NMR (300 MHz, $CDCl_3$) δ 8.02 (d, J=7.1 Hz, 2H), 7.57 (tt, J=7.4, 1.2 Hz, 1H), 7.45 (m, 3H), 6.54 (s, 1H), 5.26 (s, 1H), 4.45 (t, J=5.9 Hz, 3.87 (s, 3H), 3.85 (s, 3H), 3.42 (t, 5.6 Hz, 2H), 2.14 (tt, J=5.9, 5.6 Hz, 2H).

methyl 5-(3-(2-fluorobenzamido)propoxy)-4-methoxy-2-nitrobenzoate 56b)

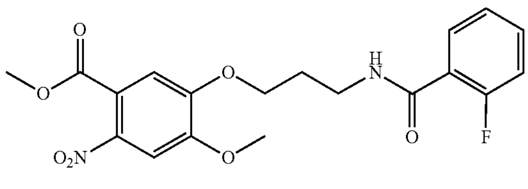 [SMILES: COC(=O)c1cc(OCCCNC(=O)c2ccccc2F)c(OC)cc1[N+](=O)[O-]]

Following the procedure described for 56a, reaction of 55 (90 mg, 0.32 mmol), pyridine (0.102 mL, 1.27 mmol) and 2-fluorobenzoyl chloride (0.113 mL, 0.95 mmol) in $CH_2Cl_2$ (10 mL) under $N_2$ afforded 56b (116 mg, 90%). $^1H$ NMR (300 MHz, $CDCl_3$) δ 7.93 (td, J=7.5, 1.8 Hz, 1H), 7.53 (m, 1H), 7.45 (s, 1H), 7.23 (m, 1H), 7.16 (dd, J=11.1, 2.8 Hz, 1H), 6.55 (s, 1H), 5.24 (t, J=5.7 Hz, 1H), 4.45 (t, J=5.9 Hz, 2H), 3.87 (s, 6H), 3.44 (dt, J=6.0, 6.5 Hz, 2H), 2.12 (tt, J=5.9, 6.5 Hz, 2H).

methyl 5-(3-(2-fluorobenzamido)propoxy-4-methoxy-2-nitrobenzoate (56b)

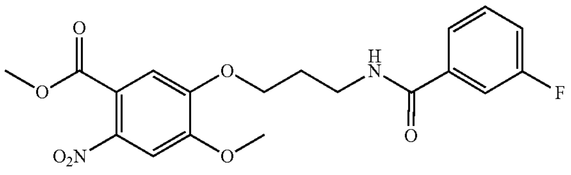

To a mixture of 56a (100 g, 0.35 mmol), 4-(dimethylamino)pyridine (43 mg, 0.35 mmol) and 3-fluorobenzoic acid (148 mg, 1.05 mmol) in dry $CH_2Cl_2$ (10 mL) was added N, N'-dicyclohexylcarbodiimide (363 mg, 1.76 mmol) in dry $CH_2Cl_2$ (5 mL) dropwise in an ice-bath. The resulting solution was stirred at $N_2$ under $N_2$ for 12 h. The reaction mixture was suspended in $H_2O$ (50 mL) and then extracted with $CH_2Cl_2$ (3×50 mL). The combined organic layer was dried over $MgSO_4$, filtered and concentrated in vacuo. The mixture was filtered and washed with EtOAc/n-hexane=1:1 (10 mL). The residue was purified by silica gel chromatography (EtOAc/n-hexane=1:5) to afford 56c (129 mg, 90%). $^1H$ NMR (300 MHz, $CDCl_3$) δ 7.82 (dt, J=7.6, 1.3 Hz, 1H), 7.69 (m, 1H), 7.46 (s, H), 7.42 (m, 1H), 7.28 (m, 1H), 6.54 (s, 1H), 5.22 (s, 1H), 4.45 (t, J=5.9 Hz, 2H), 3.88 (s, 6H), 3.42 (dt, J=5.0, 6.2 Hz, 2H), 2.14 (tt, J=5.9 Hz, 2H).

methyl 5-(3-(4-fluorobenzamido)propoxy)-4-methoxy-2-nitrobenzoate (56d)

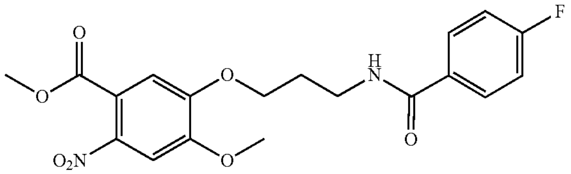 [SMILES: COC(=O)c1cc(OCCCNC(=O)c2ccc(F)cc2)c(OC)cc1[N+](=O)[O-]]

Following the procedure described for 56a, reaction of 55 (150 mg, 0.53 mmol), pyridine (0.171 mL, 2.11 mmol) and 4-fluorobenzoyl chloride (0.187 mL, 1.58 mmol) in $CH_2Cl_2$ (10 mL) wider $N_2$ afforded 56d (191 mg, 89%). $^1H$ NMR (300 MHz, $CDCl_3$) δ 8.04 (m, 2H), 7.46 (s, 1H), 7.11 (m, 2H), 6.54 (s, 1H), 5.21 (s, 1H), 4.43 (t, J=5.9 Hz, 2H), 3.88 (s, 6H), 3.41 (dt, J=5.9, 6.7 Hz, 2H), 2.13 (tt, J=6.7, 5.9 Hz, 3H).

methyl 5-(3-(2,6-difluorobenzamido)propoxy)-4-methoxy-2-nitrobenzoate (56e)

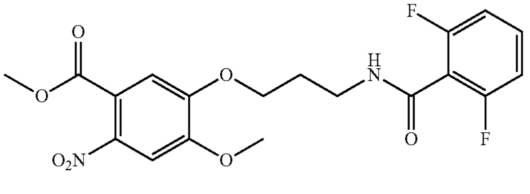

Following the procedure described for 56c, reaction of 55 (100 mg, 0.35 mmol), 2,6-difluorobenzoic acid (167 mg, 1.05 mmol), 4-(dimethylamino)pyridine (43 mg, 0.35 mmol) and N, N'-dicyclohexylcarbodiimide (363 mg, 1.76 mmol) in $CH_2Cl_2$ (15 mL) under $N_2$ afforded 56e (147 mg, 98%). $^1H$ NMR (300 MHz, $CDCl_3$) δ 7.46 (s, 1H), 7.38 (m, 1H), 6.96 (m, 2H), 6.54 (s, 1H), 5.20 (s, 1H), 4.47 (t, J=5.9 Hz, 2H), 3.88 (s, 3H), 3.88 (s, 3H), 3.42 (t, J=6.8 Hz, 2H), 2.10 (tt, J=5.9, 6.8 Hz, 3H).

methyl 5-(3-(2,6-dimethoxybenzamido)propoxy)-4-methoxy-2-nitrobenzoate (56f)

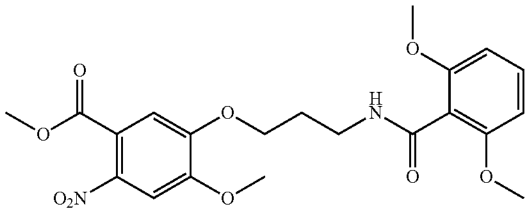

Following the procedure described for 56a, reaction of 55 (120 mg, 0.42 mmol), pyridine (0.136 mL, 1.69 mmol) and 2,6-dimethoxybenzoyl chloride (254 mg, 1.27 mmol) $CH_2Cl_2$ (10 mL) under $N_2$ afforded 56f (189 mg, 99%). $^1H$ NMR (300 MHz, $CDCl_3$) δ 7.45 (s, 1H), 7.29 (t, J=8.5 Hz, 1H), 6.56 (d, J=8.5 Hz, 2H), 6.52 (s, 1H), 5.37 (s, 1H), 4.45 (t, J=5.8 Hz, 2H), 3.86 (s, 3H), 3.83 (s, 3H), 3.78 (s, 6H), 3.42 (dt, J=6.1, 6.4 Hz, 2H), 2.07 (tt, J=5.8, 6.4 Hz, 3H).

methyl 4-methoxy-5-(3-(3-methoxybenzamido)propoxy)-2-nitrobenzoate (56g)

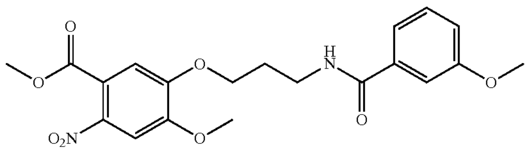

Following the procedure described for 56a, reaction of 55 (150 mg, 0.53 mmol), pyridine (0.171 mL, 2.11 mmol) and 3-methoxybenzoyl chloride (222 mL, 1.58 mmol) in $CH_2Cl_2$ (10 mL) under $N_2$ afforded 56g (218 mg, 99%), $^1H$ NMR (300 MHz, $CDCl_3$) δ 7.78 (dt, J=7.8, 1.2 Hz, 1H), 7.69 (m, 1H), 7.61 (s, 1H), 7.51 (t, J=7.9 Hz, 1H), 7.27 (ddd, J=8.3, 2.7, 0.9 Hz, 1H), 6.69 (s, 1H), 5.41 (s, 1H), 4.60 (t, J=5.9 Hz, 2H), 4.04 (s, 3H), 4.02 (s, 3H), 4.00 (s, 3H), 3.58 (dt, J=6.0, 6.5 Hz, 2H), 2.11 (tt, J=5.9, 6.5 Hz, 2H).

methyl 4-methoxy-5-(3-(4-methoxybenzamido)propoxy)-2-nitrobenzoate (56h)

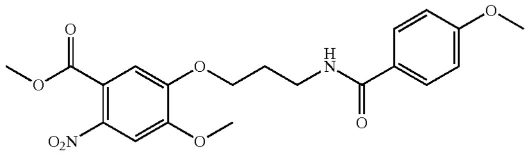

Following the procedure described for 56a, reaction of 55 (90 mg, 0.32 mmol), pyridine (0.102 mL, 1.27 mmol) and 4-methoxybenzoyl chloride (0.128 mL, 0.95 mmol) in $CH_2Cl_2$ (10 mL) under $N_2$ afforded 56h (131 mg, 99%). $^1$H NMR (300 MHz, $CDCl_3$) δ 7.97 (d, J=9.0 Hz, 2H), 7.45 (s, 1H), 6.91 (d, 9.0 Hz, 2H), 6.54 (s, 2H), 5.26 (s, 2H), 4.41 (t, 5.9 Hz, 2H), 3.88 (s, 3H), 3.87 (s, 3H), 3.85 (s, 3H), 3.41 (dt, J=6.0, 6.5 Hz, 2H), 2.11 (tt, J=5.9, 6.0 Hz, 2H).

methyl 4-methoxy-2-nitro-5-(3-(2-phenylacetamido) propoxy)benzoate (56i)

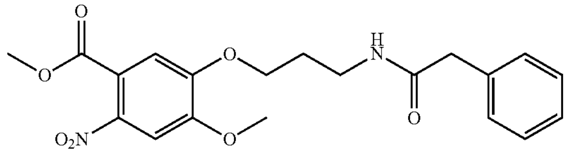

Following the procedure described for 56c, reaction of 55 (50 mg, 0.18 mmol), phenylacetic acid (48 mg, 0.35 mmol), 4-(dimethylamino)pyridine (21 mg, 0.18 mmol) and N, N'-dicyclohexylcarbodiimide (73 mg, 0.35 mmol) in $CH_2Cl_2$ (15 mL) under $N_2$ afforded 56i (68 mg, 96%). $^1$H NMR (300 MHz, $CDCl_3$) δ 7.47 (s, 1H), 7.29 (m, 5H), 6.47 (s, 1H), 5.11 (s, 1H) 4.20 (t, J=6.0 Hz, 2H), 3.92 (s, 3H), 3.90 (s, 3H), 3.63 (s, 2H), 3.24 (dt, J=6.0, 6.5 Hz, 2H), 1.96 (tt, J=6.0, 6.9 Hz 2H).

methyl 5-(3-(2-(2-fluorophenyl)acetamido) propoxy)-4-methoxy-2-nitrobenzoate (56k)

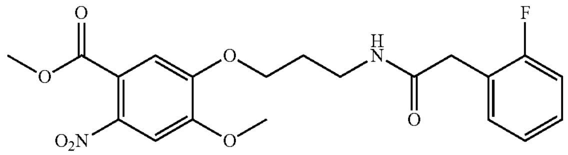

Following the procedure described for 56a, reaction of 55 (120 mg, 0.42 mmol), 2-fluorophenylacetic acid (195 mg, 1.27 mmol), 4-(dimethylamino)pyridine (51 mg, 0.42 mmol) and N, N'-dicyclohexylcarbodiimide (435 mg, 2.11 mmol) in $CH_2Cl_2$ (15 mL) under $N_2$ afforded 56j (176 mg, 99%). $^1$H NMR (300 MHz, $CDCl_3$) δ 7.47 (s, 1H), 7.24 (m, 2H), 7.10 (m, 1H), 7.06 (m, 1H), 6.48 (m, 1H), 5.14 (s, 1H), 4.22 (t, J=6.0 Hz, 2H), 3.92 (s, 3H), 3.90 (s, 3H), 3.68 (d, J=1.1 Hz, 2H), 3.27 (dt, J=5.9, 6.7 Hz, 2H), 1.97 (tt, J=6.0, 6.7 Hz, 2H).

methyl 5-(3-(2-(3-fluorophenyl)acetamido) propoxy)-4-methoxy-2-nitrobenzoate (56k)

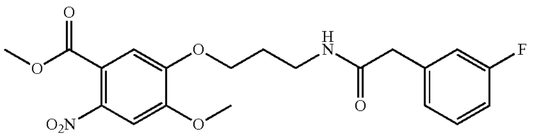 [SMILES: COC(=O)c1cc(OCCCNC(=O)Cc2cccc(F)c2)c(OC)cc1[N+](=O)[O-]]

Following the procedure described for 56a, reaction of 55 (150 mg, 0.53 mmol), pyridine (0.170 mL, 2.11 mmol) and 3-fluorophenyl chloride (109 mg, 0.63 mmol) in $CH_2Cl_2$ (10 mL) under $N_2$ afforded 56k (210 mg, 95%). $^1$H NMR (300 MHz, $CDCl_3$) δ 7.47 (s, 1H), 7.27 (m, 1H), 7.03 (d, J=8.5 Hz, 1H), 6.96 (m, 2H), 6.48 (s, 1H), 5.10 (s, 1H), 4.21 (t, J=6.1 Hz, 2H), 3.92 (s, 3H), 3.90 (s, 3H), 3.62 (s, 2), 3.26 (dt, J=5.9, 6.6 Hz, 2H), 1.98 (tt, J=6.1, 6.6 Hz, 2H).

methyl 5-(3-(2-(4-fluorophenyl)acetamido) propoxy)-4-methoxy-2-nitrobenzoate (56l)

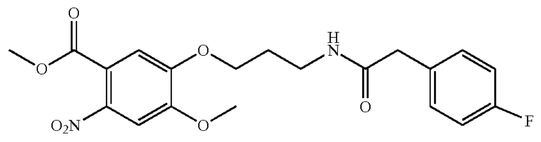 [SMILES: COC(=O)c1cc(OCCCNC(=O)Cc2ccc(F)cc2)c(OC)cc1[N+](=O)[O-]]

Following the procedure described for 56c, reaction of 55 (150 mg, 0.53 mmol), 4-fluorophenylacetic acid (244 mg, 1.58 mmol), 4-(dimethylamino)pyridine (64 mg, 0.53 mmol) and N, N'-dicyclohexylcarbodiimide (544 mg, 2.64 mmol) in $CH_2Cl_2$ (15 mL) under $N_2$ afforded 56l (219 mg, 99%). $^1$H NMR (300 MHz, $CDCl_3$) δ 7.47 (s, 1H), 7.22 (m, 2H), 6.99 (m, 2H), 6.49 (s, 1H), 5.11 (s, 1H), 4.20 (t, J=6.0 Hz, 2H), 3.92 (s, 3H), 3.90 (s, 3H), 3.60 (s, 2H), 3.26 (dt, J=5.9, 6.6 Hz, 2H), 1.97 (tt, J=6.0, 6.6 Hz, 2H).

methyl 4-methoxy-5-(3-(2-(2-methoxyphenyl)acetamido)propoxy)-2-nitrobenzoate (56m)

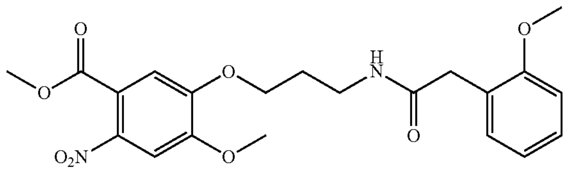

Following the procedure described for 56c, reaction of 55 (120 mg, 0.42 mmol), 2-methoxyphenylacetic acid (210 mg, 1.27 mmol), 4-(dimethylamino)pyridine (51 mg, 0.42 mmol) and N, N'-dicyclohexylcarbodiimide (435 mg, 2.11 mmol) in $CH_2Cl_2$ (15 mL) under $N_2$ afforded 56m (118 mg, 65%). $^1$H NMR (300 MHz, $CDCl_3$) δ 7.46 (s, 1H), 7.25 (td, J=7.8, 1.7 Hz, 1H), 7.16 (dd, J=7.4, 1.7 Hz, 1H), 6.89 (td, J=7.4, 1.1 Hz, 1H), 6.86 (d, 8.2 Hz, 1H), 6.47 (s, 1H), 5.19 (s, 1H), 4.21 (t, J=6.0 Hz, 2H), 3.91 (s, 3H), 3.90 (s, 3H), 3.77 (s, 3H), 3.63 (s, 2H), 3.26 (dt, J=5.9, 6.6 Hz, 2H), 1.96 (tt, J=6.0, 6.6 Hz, 2H).

methyl 4-methoxy-5-(3-(2-(3-methoxyphenyl)acetamido)propoxy)-2-nitrobenzoate (56n)

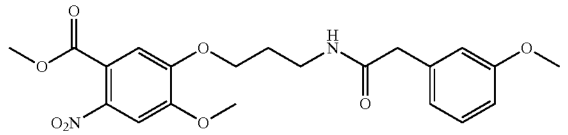

Following the procedure described for 56a, reaction of 55 (150 mg, 0.53 minor), pyridine (0.128 mL, 1.58 mmol) and 3-methoxyphenyl chloride (0.089 mL, 0.63 minor) in $CH_2Cl_2$ (10 mL) under $N_2$ afforded 56n (206 mg, 90%). $^1H$ NMR (300 MHz, $CDCl_3$) δ 7.46 (s, 1H), 7.25 (td, J=7.5, 1.2 Hz, 1H), 6.81 (m, 3H), 6.48 (s, 1H), 5.13 (s, 1H), 4.20 (t, J=6.0 Hz, 2H), 3.92 (s, 3H), 3.90 (s, 3H), 3.77 (s, 3H), 3.60 (s, 2H), 3.25 (dt J=5.9, 6.6 Hz, 2H), 1.97 (tt, J=6.0, 6.6 Hz, 2H).

methyl 4-methoxy-5-(3-(2-(4-methoxyphenyl)acetamido)propoxy)-2-nitrobenzoate (56o)

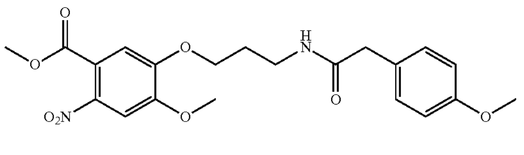

Following the procedure described for 56c, reaction of 55 (130 mg, 0.46 mmol), 4-methoxyphenylacetic acid (228 mg, 1.37 mmol), 4-(dimethylamino)pyridine (51 mg, 0.46 mmol) and N, N'-dicyclohexylcarbodiimide (472 mg, 2.29 mmol) in $CH_2Cl_2$ (15 mL) under $N_2$ afforded 56o (172 mg, 87%). $^1H$ NMR (300 MHz, $CDCl_3$) δ 7.47 (s, 1H), 7.17 (m, 2H), 6.84 (m, 2H), 6.49 (s, 1H), 5.48 (t, J=5.5 Hz, 1H), 4.19 (t, J=6.0 Hz, 2H), 3.92 (s, 3H), 3.90 (s, 3H) 3.77 (s, 3H), 3.56 (s, 2H), 3.26 (dt, J=6.0, 6.6 Hz, 2H), 1.96 (tt, J=6.0, 6.6 Hz, 2H).

4-methoxy-5-(3-(2-(3,4,5-trimethoxyphenyl)acetamido)propoxy)-2-nitrobenzoate (56p)

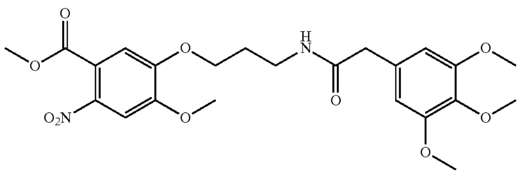

Following the procedure described for 56c, reaction of 55 (120 mg, 0.42 mmol), 3,4,5-trimethoxyphenylacetic acid (286 mg 1.27 mmol), 4-(dimethylamino)pyridine (52 mg, 0.42 mmol) and N, N'-dicyclohexylcarbodiimide (435 mg, 2.11 mmol) is $CH_2Cl_2$ (15 mL) under $N_2$ afforded 56p (168 mg, 81%). $^1H$ NMR (300 MHz, $CDCl_3$) δ 7.47 (s, 1H), 6.52 (s, 1H), 6.48 (s, 2H), 5.14 (s, 1H), 4.21 (t, J=6.0 Hz, 2H), 3.92 (s, 3H), 3.90 (s, 3H), 3.82 (s, 6H), 3.80 (s, 3H), 3.56 (s, 2H), 3.30 (dt, J=5.9, 6.7 Hz, 2H), 1.99 (tt, J=6.0, 6.7 Hz, 2H).

methyl 5-(3-(2-(2-chlorophenyl)acetamido)propoxy)-4-methoxy-2-nitrobenzoate (56q)

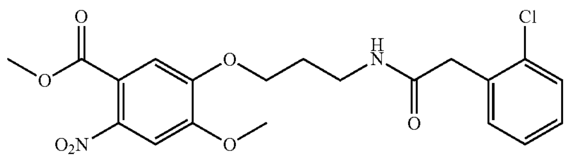

Following the procedure described for 56a, reaction of 55 (150 mg, 0.53 mmol), pyridine (0.128 mL, 1.58 mmol) and 2-chlorophenylacetyl chloride (0.092 mL, 0.63 mmol) in $CH_2Cl_2$ (10 mL) under $N_2$ afforded 56q (207 mg, 90%). $^1H$ NMR (300 MHz, $CDCl_3$) δ 7.47 (s, 1H), 7.37 (m, 1H), 7.24 (m, 3H), 6.47 (s, 1H), 5.13 (s, 1H), 4.23 (t, J=6.0 Hz, 2H), 3.92 (s, 3H), 3.90 (s, 3H), 3.78 (s, 2H), 3.26 (dt, J=6.0, 6.6 Hz, 2H), 1.97 (tt, J=6.0, 6.6 Hz, 2H).

methyl 5-(3-(2-(3-chlorophenyl)acetamido)propoxy)-4-methoxy-2-nitrobenzoate (56r)

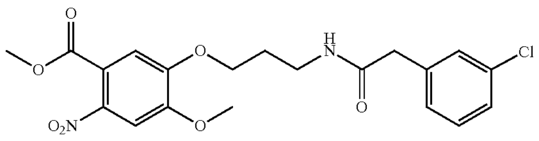

Following the procedure described for 56c, reaction of 55 (120 mg, 0.42 mmol), 3-chlorophenylacetic acid (216 mg, 1.27 mmol), 4-dimethylamino)pyridine (51 mg, 0.42 mmol) and N, N'-dicyclohexylcarbodiimide (435 mg, 2.11 mmol) in $CH_2Cl_2$ (15 mL) under $N_2$ afforded 56r (182 mg, 99%). $^1H$ NMR (300 MHz, $CDCl_3$) δ 7.47 (s, 1H), 7.25 (m, 3H), 7.15 (m, 1H), 6.49 (s, 1H), 5.10 (t, J=5.3 Hz, 1H), 4.21 (t, J=6.1 Hz, 2H), 3.92 (s, 3H), 3.90 (s, 3H), 3.60 (s, 2H), 3.27 (dt, J=5.9, 6.7 Hz, 2H), 1.98 (tt, J=6.1, 6.7 Hz, 2H).

methyl 4-methoxy-5-(3-(2-(2-(trifluoromethyl)phenyl)acetamido)propoxy)-2-nitro benzoate (56s)

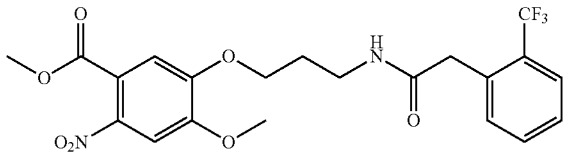

Following the procedure described for 56c, reaction of 55 (150 mg, 0.53 mmol), 2-(trifluoromethyl)phenylacetic acid (323 mg, 1.58 mmol), 4-(dimethylamino)pyridine (64 mg, 0.53 mmol) and N, N'-dicyclohexylcarbodiimide (544 mg, 2.64 mmol) in $CH_2Cl_2$ (15 mL) under $N_2$ afforded 56s (230 mg, 93%). $^1H$ NMR (300 MHz, $CDCl_3$) δ 7.65 (d, J=7.9 Hz, 1H), 7.51 (t, 7.4 Hz, 1H), 7.46 (s, 1H), 7.38 (t, J=6.1 Hz, 2H), 6.47 (s, 1H), 5.12 (s, 1H), 4.21 (t, J=6.0 Hz, 2H), 3.92 (s, 3H), 3.90 (s, 3H), 3.84 (d, J=1.1 Hz, 2H), 3.26 (dt, J=6.0, 6.7 Hz, 2H), 1.96 (tt, J=6.0, 6.7 Hz, 2H).

methyl 4-methoxy-5-(3-(2-(3-(trifluoromethyl)phenyl)acetamido)propoxy)-2-nitro benzoate (56t)

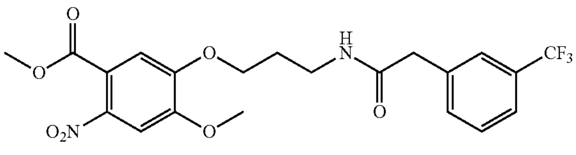 [SMILES: COC(=O)c1cc(OCCCNC(=O)Cc2cccc(C(F)(F)F)c2)c(OC)cc1[N+](=O)[O-]]

Following the procedure described for 56c, reaction of 55 (150 mg, 0.53 mmol), 3-(trifluoromethyl)phenylacetic acid (323 mg, 1.58 mmol), 4-(dimethylamino)pyridine (64 mg, 0.53 mmol) and N, N'-dicyclohexylcarbodiimide (544 mg, 2.64 mmol) in $CH_2Cl_2$ (15 mL) under $N_2$ afforded 56t (240 mg, 97%). $^1H$ NMR (300 MHz, $CDCl_3$) δ 7.53 (m, 2H), 7.45 (m, 3H), 6.49 (s, 1H), 5.10 (t, J=5.4 Hz, 1H), 4.22 (t, J=6.0 Hz, 2H), 3.92 (s, 3H), 3.90 (s, 3H), 3.69 (s, 2H), 3.27 (dt, J=5.9, 6.7 Hz, 2H), 1.98 (tt, J=6.0, 6.7 Hz, 2H).

methyl 4-methoxy-5-(3-(2-(4-(trifluoromethyl)phenyl)acetamido)propoxy)-2-nitro benzoate (56u)

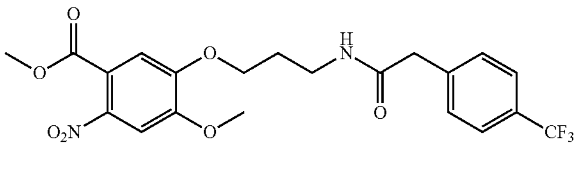 [SMILES: COC(=O)c1cc(OCCCNC(=O)Cc2ccc(C(F)(F)F)cc2)c(OC)cc1[N+](=O)[O-]]

Following the procedure described for 56a, reaction of 55 (150 mg, 0.53 mmol), pyridine (0.171 mL, 2.11 mmol) and 4-(trifluoromethyl)phenylacetyl chloride (141 mg, 0.63 mmol) $CH_2Cl_2$ (10 mL) under $N_2$ afforded 56u (223 mg, 90%). $^1H$ NMR (300 MHz, $CDCl_3$) δ 7.58 (d, J=8.1 Hz, 2H), 7.47 (s, 1H), 7.39 (d, J=8.1 Hz, 2H), 6.51 (s, 1H), 5.11 (s, 1H), 4.21 (t, J=6.1 Hz, 2H) 3.92 (s, 3H), 3.90 (s, 3H), 3.69 (s, 2H), 3.29 (dt, J=5.9, 6.5 Hz, 2H), 1.98 (tt, J=6.1, 6.5 Hz, 2H).

methyl 4-methoxy-5-(3-(oxazole-5-carboxamido) propoxy)-2-nitro benzoate (56v)

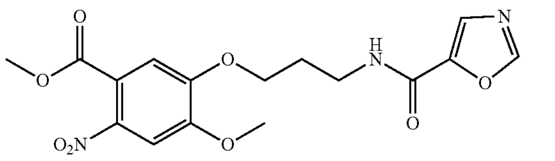 [SMILES: COC(=O)c1cc(OCCCNC(=O)c2cnco2)c(OC)cc1[N+](=O)[O-]]

Following the procedure described for 56c, reaction of 55 (150 mg, 0.53 mmol), oxazole-5-carboxylic acid (179 mg, 1.58 mmol), 4-(dimethylamino)pyridine (64 mg, 0.53 mmol) and N, N'-dicyclohexylcarbodiimide (544 mg, 2.64 mmol) in $CH_2Cl_2$ (15 mL) under $N_2$ afforded 56v (185 mg, 92%). $^1H$ NMR (300 MHz, $CDCl_3$) δ 8.02 (s, 1H), 7.79 (s, 1H), 7.46 (s, 1H), 6.54 (s, 1H), 5.18 (t, J=5.6 Hz, 1H), 4.45 (t, J=6.0 Hz, 2H), 3.92 (s, 3H), 3.88 (s, 3H), 3.40 (dt, J=6.0, 6.6 Hz, 2H), 2.11 (tt, J=6.0, 6.6 Hz, 2H).

methyl 2-amino-5-(3-benzamidopropoxy)-4-methoxybenzoate (57a)

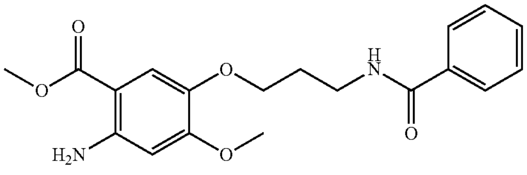

Following the procedure described for compound 38, reaction of 56a (150 mg, 0.39 mmol) in HOAc/TH=1:4 (10 mL) was added Zn (253 mg, 3.86 mmol) and the mixture was stirred at RT under $N_2$ to afford 57a (113 mg, 82%). $^1H$ NMR (300 MHz, $CDCl_3$) δ 8.05 (m, 2H), 7.54 (tt, J=7.4, 1.6 Hz, 1H), 7.42 (m, 2H), 7.04 (s, 1H), 6.08 (s, 1H), 4.44 (t, 6.1 Hz, 2H), 3.79 (s, 3H), 3.77 (s, 3H), 3.27 (t, J=5.8 Hz, 2H), 2.11 (tt, J=6.1, 5.8 Hz 2H).

methyl 2-amino-5-(3-(2-fluorobenzamido)propoxy)-4-methoxybenzoate (57b)

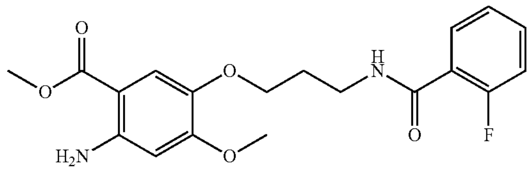

Following the procedure described for compound 38, reaction of 56b (100 mg, 0.25 mmol) Zn (161 mg, 2.46 mmol) in HOAc/THF=1:4 (10 mL) under $N_2$ afforded 57b (89 mg, 96%) $^1H$ NMR (300 MHz, $CDCl_3$) δ 7.93 (td, J=7.5, 1.9 Hz, 1H), 7.51 (m, 1H), 7.18 (tt, J=7.6, 1.1 Hz, 1H), 7.12 (ddd, J=10.8, 8.3, 1.0 Hz, 1H), 7.04 (s, 1H), 6.08 (s, 1H), 4.45 (t, J=6.1 Hz, 2H), 3.79 (s, 3H), 3.78 (s, 3H), 3.28 (t, J=6.7 Hz, 2H), 2.10 (tt, J=6.7 Hz, 2H).

methyl 2-amino-5-(3-(3-fluorobenzamido)propoxy)-4-methoxybenzoate (57c)

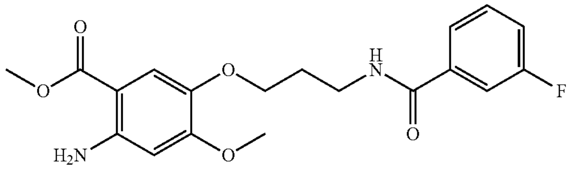 [SMILES: COC(=O)c1cc(OCCCNC(=O)c2cccc(F)c2)c(OC)cc1N]

Following the procedure described for compound 38, reaction of 56c (200 mg, 0.49 mmol), Zn (321 mg, 4.92 mmol) in HOAc/THF=1:4 (20 under $N_2$ afforded 57c (120 mg, 65%). $^1H$ NMR (300 MHz, $CDCl_3$) δ 7.82 (d, J=7.7 Hz, 1H), 7.72 (m, 1H), 7.41 (m, 1H), 7.25 (m, 1H), 7.03 (s, 1H), 6.09 (s, 1H), 5.35 (t, J=6.1 Hz, 2H), 3.80 (s, 3H), 3.79 (s, 3H), 3.27 (t, J=6.7 Hz, 2H), 2.11 (tt, J=6.1, 6.7 Hz, 2H).

methyl 2-amino-5-(3-(4-fluorobenzamido)propoxy)-4-methoxybenzoate (57d)

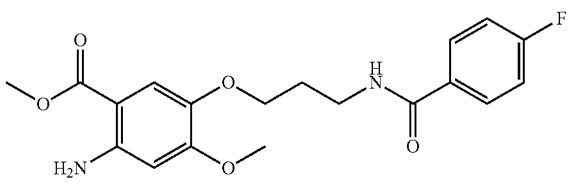

Following the procedure described for compound 38, reaction of 56d (180 mg, 0.44 mmol), Zn (289 mg, 4.43 mmol) HOAc/THF=1:4 (20 mL) under $N_2$ afforded 57d (125 mg, 75%). $^1$H NMR (300 MHz, $CDCl_3$) δ 8.06 (m, 2H), 7.10 (m, 2H), 7.03 (s, 1H), 6.09 (s, 1H), 5.02 (s, 2H), 4.43 (t, J=6.2 Hz, 2H), 3.80 (s, 3H), 3.78 (s, 3H), 3.26 (t, J=6.7 Hz, 2H), 2.10 (tt, J=6.2, 6.7 Hz, 3H).

methyl 2-amino-5-(3-(2,6-difluorobenzamido)propoxy)-4-methoxybenzoate (57e)

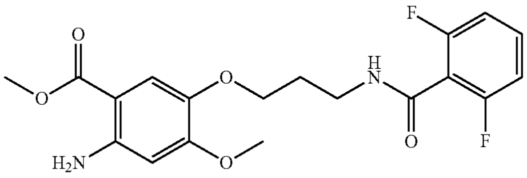

Following the procedure described for compound 38, reaction of 56e (200 mg, 0.47 mmol), Zn (308 mg, 4.71 mmol) HOAc/THF=1:4 (20 mL) under $N_2$ afforded 57e (149 mg, 80%). $^1$H NMR (300 MHz, $CDCl_3$) δ 7.40 (m, 1H), 7.03 (s, 1H), 6.94 (t, J=8.2 Hz, 2H), 6.08 (s, 1H), 4.48 (t, J=6.2 Hz, 2H), 3.80 (s, 3H), 3.79 (s, 3H), 3.26 (t, J=6.8 Hz, 2H), 2.08 (tt, J=6.2, 6.8 Hz, 3H).

methyl 2-amino-5-(3-(2,6-dimethoxybenzamido)propoxy)-4-methoxybenzoate (57f)

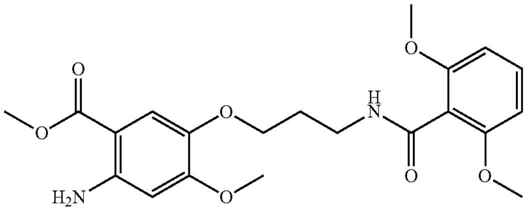

Following the procedure described for compound 38, reaction of 56f (150 mg, 0.34 mmol), Zn (218 mg, 3.35 mmol) in HOAc/THF=1:4 (20 mL) under $N_2$ afforded 57f (70 mg, 50%). $^1$H NMR (300 MHz, $CDCl_3$) δ 7.27 (t, J=8.5 Hz, 1H), 7.03 (s, 1H), 6.54 (d, J=8.3 Hz, 2H), 6.08 (s, 1H), 4.44 (t, J=6.0 Hz, 2H), 3.78 (s, 3H), 3.77 (s, 9H), 3.25 (t, J=6.9 Hz, 2H), 2.05 (tt, J=6.0, 6.9 Hz, 3H).

methyl 2-amino-4-methoxy-5-(3-(3-methoxybenzamido)propoxy)benzoate (57g)

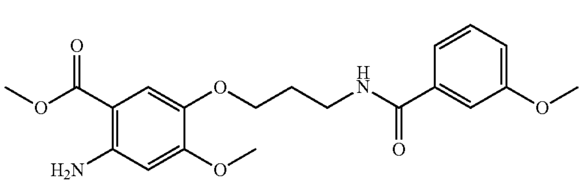

Following the procedure described for compound 38, reaction of 56g (200 mg, 0.48 mmol), Zn 313 mg, 4.79 mmol) in HOAc/THF=1:4 (20 mL) under $N_2$ afforded 57g (166 mg, 89%). $^1$H NMR (300 MHz, $CDCl_3$) δ 7.64 (dt, J=7.6, 1.2 Hz, 1H), 7.56 (dd, J=2.6, 1.5 Hz, 1H), 7.33 (t, J=8.0 Hz, 1H), 7.09 (ddd, J=8.2, 2.7, 1.0 Hz, 1H), 7.04 (s, 1H), 6.08 (s, 1H), 4.44 (t, J=6.1 Hz, 2H), 4.83 (s, 3H), 3.79 (s, 3H), 3.78 (s, 3H), 3.27 (t, J=6.7 Hz, 2H), 2.10 (tt, J=6.1, 6.7 Hz, 2H).

methyl 2-amino-4-methoxy-5-(3-(4-methoxybenzamido)propoxy)benzoate (57h)

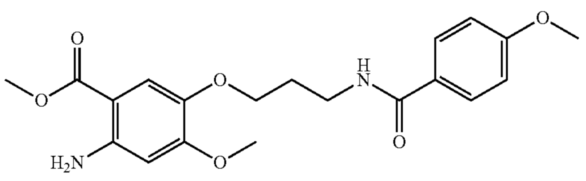

Following the procedure described for compound 38, reaction of 56h (115 mg, 0.27 mmol), Zn (180 mg, 2.75 mmol) in HOAc/THF=1:4 (10 mL) under $N_2$ afforded 57h (85 mg, 80%). $^1$H NMR (300 MHz, $CDCl_3$) δ 8.00 (m, 2H), 7.04 (s, 1H), 6.90 (m, 2H), 6.08 (s, 1H), 4.41 (t, J=6.1 Hz, 2H), 3.84 (s, 3H), 3.80 (s, 3H), 3.78 (s, 3H), 3.26 (t, J=6.8 Hz, 2.14), 2.09 (tt, J=6.1, 6.8 Hz, 2H).

methyl 2-amino-4-methoxy-5-(3-(2-phenylacetamido)propoxy)benzoate (57i)

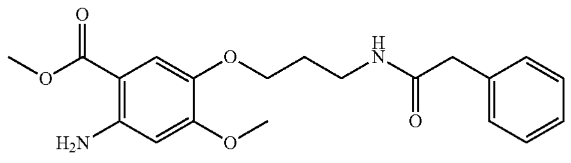

Following the procedure described for compound 38, reaction of 56i (81 mg, 0.20 mmol), Zn (132 mg, 2.01 mmol) its HOAc/THF=1:4 (10 mL) under $N_2$ afforded 57i (69 mg, 92%). $^1$H NMR (300 MHz, $CDCl_3$) δ 7.28 (m, 5H), 7.00 (s, 1H), 6.09 (s, 1H), 4.21 (t, J=6.2 Hz, 2H), 3.83 (s, 3H), 3.81 (s, 3H), 3.62 (s, 2H), 3.13 (t, J=6.8 Hz, 2H), 1.94 (tt, J=6.2, 6.8 Hz, 2H).

methyl 2-amino-5-(3-(2-(2-fluorophenyl)acetamido)propoxy)-4-methoxybenzoate (57j)

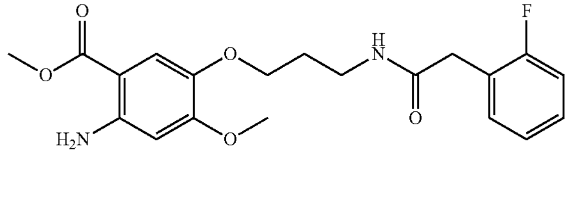

Following the procedure described for compound 38, reaction of 56j (150 mg, 0.36 mmol), Zn (233 mg, 3.57 mmol) in HOAc/THF=1:4 (20 mL) under $N_2$ afforded 57j (74 mg, 53%). $^1$H NMR (300 MHz, $CDCl_3$) δ 7.24 (m, 2H), 7.05 (m, 2H), 7.00 (s, 1H), 6.09 (s, 1H), 4.23 (t, J=6.2. Hz, 1H), 3.83 (s, 3H), 3.81 (s, 3H), 3.68 (s, 2H), 3.13 (t, J=6.8 Hz, 2H), 1.95 (tt, J=6.2, 6.8 Hz, 2H).

methyl 2-amino-5-(3-(2-(3-fluorophenyl)acetamido) propoxy)-4-methoxybenzoate (57k)

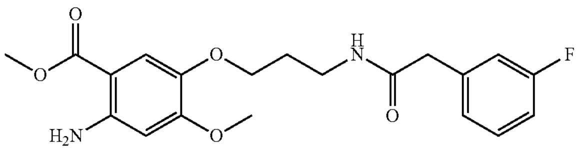

Following the procedure described for compound 38, reaction of 56k (150 mg, 0.36 mmol), Zn (233 mg, 3.57 mmol) in HOAc/THF=1:4 (20 mL) under $N_2$ afforded 57k (110 mg, 79%). $^1$H NMR (300 MHz, $CDCl_3$) δ 7.26 (m, 1H), 6.98 (m, 4H), 6.09 (s, 2H), 4.22 (t, J=6.3 Hz, 2H), 3.83 (s, 3H), 3.81 (s, 3H), 3.61 (s, 2H), 3.13 (t, J=6.8 Hz, 2H), 1.95 (tt, 6.3, 6.8 Hz, 2H).

methyl 2-amino-5-(2-(4-fluorophenyl)acetamido) propoxy)-4-methoxybenzoate (57l)

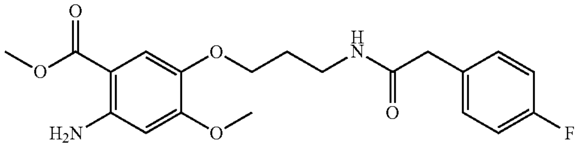 [SMILES: COC(=O)c1cc(OCCCNC(=O)Cc2ccc(F)cc2)c(OC)cc1N]

Following the procedure described for compound 38, reaction of 56l (175 mg, 0.42 mmol), Zn (272 mg, 4.16 mmol) in HOAc/THF=1:4 (20 mL) under $N_2$ afforded 57l (120 mg, 74%). $^1$H NMR (300 MHz, $CDC_3$) δ 7.23 (m, 2H), 6.98 (m, 3H), 6.09 (s, 1H), 4.21 (t, J=6.2 Hz, 2H), 3.83 (s, 3H), 3.81 (s, 3H), 3.59 (s, 2H), 3.13 (t, J=6.8 Hz, 2H), 1.95 (tt, J=6.2, 6.8 Hz, 2H).

methyl 2-amino-4-methoxy-5-(3-(2-(2-methoxyphenyl)acetamido)propoxy)benzoate (57m)

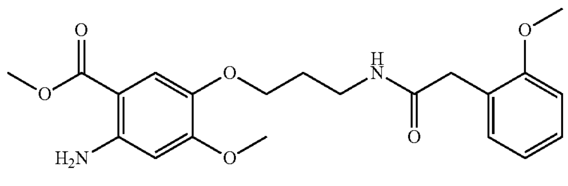

Following the procedure described for compound 38, reaction of 56m (100 mg, 0.23 mmol), Zn (151 mg, 2.31 mmol) in HOAc/THF=1:4 (20 mL) under $N_2$ afforded 57m (73 mg, 78%). $^1$H NMR (300 MHz, $CDCl_3$) δ7.25 (td, J=7.9, 1.7 Hz, 1H), 7.16 (dd, J=7.5, 1.7 Hz, 1H), 7.00 (s, 2H), 6.89 (td, J=7.4, 1.0 Hz, 1H), 6.84 (d, 8.2 Hz, 1H), 6.09 (s, 1H), 4.21 (t, J=6.2 Hz, 2H), 3.83 (s, 3H), 3.80 (s, 3H), 3.77 (s, 3H), 3.63 (s, 2H), 3.12 (t, J=6.8 Hz, 2H), 1.94 (tt, J=6.2, 6.8 Hz, 2H).

methyl 2-amino-4-methoxy-5-(3-(2-(3-methoxyphenyl)acetamido)propoxy)benzoate (57n)

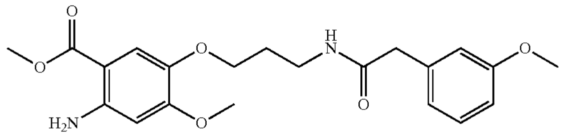

Following the procedure described for compound 38, reaction of 56n (150 mg, 0.35 mmol), Zn (227 mg 3.47 mmol) in HOAc/THF=1:4 (20 mL) under $N_2$ afforded 57n (97 mg, 69%). $^1$H NMR (300 MHz, $CDCl_3$) δ 7.21 (t, J=7.8 Hz, 1H), 6.99 (s, 1H), 6.85 (m, 1H), 6.79 (m, 2H), 6.09 (s, 1H), 4.21 (t, J==6.3 Hz, 2H), 3.82 (s, 3H), 3.81 (s, 3H) 3.76 (s, 3H), 3.59 (s, 2H), 3.13 (t, J=6.8 Hz, 2H), 1.95 (tt, J=6.3, 6.8 Hz, 2H).

methyl 2-amino-4-methoxy-5-(3-(2-(4-methoxyphenyl)acetamido)propoxy)benzoate (57o)

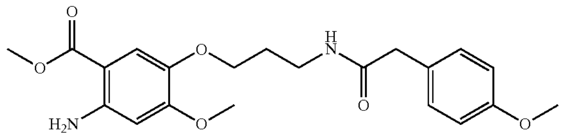

Following the procedure described for compound 38, reaction of 56o (150 mg, 0.35 mmol), Zn (227 mg 3.47 mmol) inn HOAc/THF=1:4 (20 mL) under afforded 57o (120 mg 86%). $^1$H NMR (300 MHz, $CDCl_3$) δ 7.18 (m, 2H), 7.00 (s, 1H), 6.83 (m, 2H), 6.09 (s, 1H), 4.20 (t, J=6.3 Hz, 2H), 3.83 (s, 3H), 3.81 (s, 3H), 3.76 (s, 3H), 3.56 (s, 2H), 3.13 (t, 6.8 Hz, 2H), 1.94 (tt, J=6.3, 6.8 Hz, 2H).

methyl 2-amino-4-methoxy-5-(3-(2-(3,4,5-trimethoxyphenyl)acetamido)propoxy)benzoate (57p)

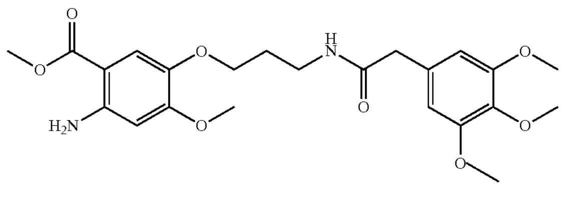

Following the procedure described for compound 38, reaction of 56p (130 mg, 0.26 mmol), Zn (173 mg, 2.64 mmol) in HOAc/THF=1:4 (20 mL) under $N_2$ afforded 57p (99 mg, 81%). $^1$H NMR (300 MHz, $CDCl_3$) δ 7.00 (s, 1H), 6.48 (s, 2H), 6.09 (s, 1H), 4.23 (t, J=6.2 Hz, 2H), 3.82 (s, 3H), 3.81 (s, 9H), 3.80 (s, 3H), 3.55 (s, 2H), 3.16 (t, J=6.7 Hz, 2H), 1.97 (tt, J=6.2, 6.7 Hz, 2H).

methyl 2-amino-5-(3-(2-(2-chlorophenyl)acetamido)propoxy)-4-methoxybenzoate (57q)

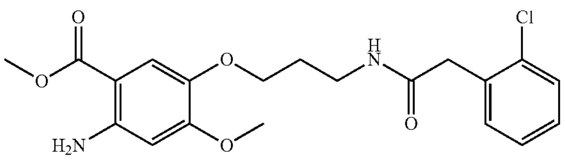 [SMILES: COC(=O)c1cc(OCCCNC(=O)Cc2ccccc2Cl)c(OC)cc1N]

Following the procedure described for compound 38, reaction of 56q (150 mg, 0.34 mmol), Zn (224 mg, 3.43 mmol) in HOAc*THF=1:4 (20 mL) under $N_2$ afforded 57q (118 mg, 84%). $^1$H NMR (300 MHz, $CDCl_3$) δ 7.36 (m, 1H), 7.23 (m, 3H), 7.00 (s, 1H), 6.09 (s, 2H), 4.24 (t, J=6.2 Hz, 2H), 3.83 (s, 3H), 3.81 (s, 3H), 3.78 (s, 2H), 3.13 (t, 6.8 Hz, 2H), 1.95 (tt, J=6.2, 6.8 Hz, 2H).

methyl 2-amino-5-(3-(2-(3-chlorophenyl)acetamido)propoxy)-4-methoxybenzoate (57r)

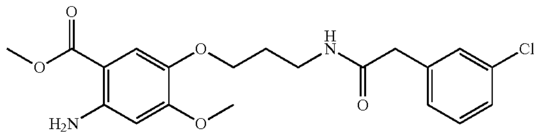

Following the procedure described for compound 38, reaction of 56r (150 mg, 0.34 mmol), (224 mg, 3.43 mmol) in HOAc/THF=1:4 (20 mL) under $N_2$ afforded 57r (100 mg, 72%). $^1$H NMR (300 MHz, $CDCl_3$) δ 7.27 (s, 1H), 7.22 (m, 2H), 7.15 (m, 1H), 7.00 (s, 2H), 6.09 (s, 2H), 4.22 (t, J=6.2 Hz, 2H), 3.83 (s, 3H), 3.81 (s, 3H), 3.59 (s, 2H), 3.14 (t, J=6.8 Hz, 2H), 1.95 (tt, J=6.2, 6.8 Hz, 2H).

methyl 2-amino-4-methoxy-5-(3-(2-(2-trifluoromethyl)phenyl)acetamido)propoxy)benzoate (57s)

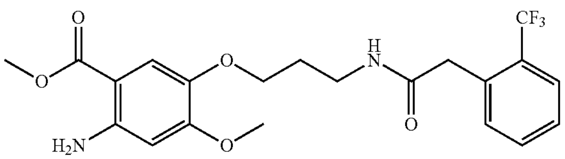

Following the procedure described for compound 38, reaction of 56s (175 mg, 0.37 mmol), Zn (243 mg, 3.72 mmol) in HOAc/THF=1:4 (20 mL) under $N_2$ afforded 57s (151 mg, 92%). $^1$H NMR (300 MHz, $CDCl_3$) δ 7.64 (d, J=7.4 Hz, 1H), 7.49 (t, J=7.2 Hz, 1H), 7.36 (m, 2H), 6.99 (s, 1H), 6.09 (s, 1H), 4.23 (t, 6.2 Hz, 2H), 3.83 (s, 6H), 3.80 (s, 2H), 3.12 (t, J=6.8 Hz, 2H), 1.94 (tt, J=6.2, 6.8 Hz, 2H).

methyl 2-amino-4-methoxy-5-(3-(2-(3-(trifluoromethyl)phenyl)acetamido)propoxy)benzoate (57t)

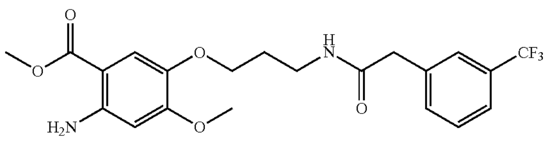 [SMILES: COC(=O)c1cc(OCCCNC(=O)Cc2cccc(C(F)(F)F)c2)c(OC)cc1N]

Following the procedure described for compound 38, reaction of 56t (200 mg, 0.43 mmol), Zn (278 mg, 4.25 mmol) HOAc/THF=1:4 (20 mL) under $N_2$ afforded 57t (112 mg, 60%). $^1$H NMR (300 MHz, $CDCl_3$) δ 7.46 (m, 4H), 7.00 (s, 1H), 6.09 (s, 1H) 4.23 (t, J=6.3 Hz, 2H), 3.82 (s, 3H), 3.81 (s, 3H), 3.68 (s, 2H), 3.14 (t, J=6.8 Hz, 2H), 1.96 (tt, J=6.3, 6.8 Hz, 2H).

methyl 2-amino-4-methoxy-5-(3-(2-(4-(trifluoromethyl)phenyl)acetamido)propoxy)benzoate (57u)

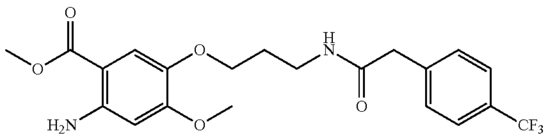 [SMILES: COC(=O)c1cc(OCCCNC(=O)Cc2ccc(C(F)(F)F)cc2)c(OC)cc1N]

Following the procedure described for compound 38, reaction of 56u (200 mg, 0.43 mmol), Zn (278 mg, 4.25 mmol) in HOAc/THF=1:4 (20 mL) under $N_2$ afforded 57u (136 mg, 71%). $^1$H NMR (300 MHz, $CDCl_3$) δ 7.56 (d, 8.2 Hz, 2H), 7.39 (d, J=8.2 Hz, 2H), 7.01 (s, 1H), 6.09 (s, 1H), 4.23 (t, J=6.3 Hz 2H), 3.82 (s, 3H), 3.81 (s, 3H), 3.68 (s, 2H), 3.14 (dt, J=6.8 Hz, 2H), 1.96 (tt, J=6.3, 6.8 Hz, 2H).

methyl 2-amino-4-methoxy-5-(3-(oxazole-5-carboxamido)propoxy)benzoate (57v)

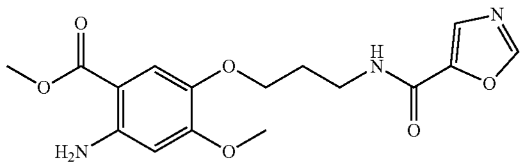 [SMILES: COC(=O)c1cc(OCCCNC(=O)c2cnco2)c(OC)cc1N]

Following the procedure described for compound 38, reaction of 56v (150 mg, 0.40 mmol), Zn (259 mg, 3.95 mmol) in HOAc/THF=1:4 (20 mL) under $N_2$ afforded 57v (132 mg, 96%), $^1$H NMR (300 MHz, $CDCl_3$) δ 8.00 (s, 1H), 7.78 (s, 1H), 7.02 (s, 1H), 6.09 (s, 1H), 4.46 (t, J=6.2 Hz, 2H), 3.81 (s, 3H), 3.81 (s, 3H), 3.24 (t, J=6.7 Hz, 2H), 2.09 (tt, J=6.2, 6.7 Hz, 2H).

methyl 4-methoxy-2-propiolamido-5-(3-(N-propioloylbenzamido)propoxy benzoate (58a)

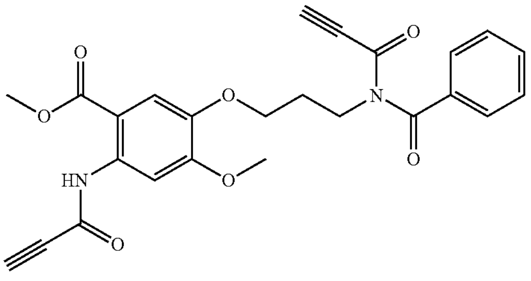 [SMILES: C#CC(=O)Nc1cc(OC)c(OCCCN(C(=O)C#C)C(=O)c2ccccc2)cc1C(=O)OC]

Following the procedure described for compound 4, reaction of 57a (50 mg, 0.14 mmol), propiolic acid (0.018 mL, 0.28 mmol) and N, N'-dicyclohexylcarbodiimide (58 mg, 0.28 mmol) in $CH_2Cl_2$ (15 mL) under $N_2$ afforded 58a (61 mg 94%). $^1$H NMR (500 MHz, $CDCl_3$) δ 11.71 (s, 2H), 8.38 (s, 1H), 7.95 (d, J=7.9 Hz, 2H), 7.88 (s, 1H) 7.52 (t, J=7.4 Hz, 1H), 7.39 (t, J=7.7 Hz, 2H), 4.34 (t, J=6.4 Hz, 2H) 3.95 (M, 1H), 3.90 (s, 3H), 3.89 (s, 3H), 3.71 (m, 1H), 2.98 (s, 1H), 2.69 (s, 1), 2.00 (tt, J=6.4, 6.7 Hz, 2H).

methyl 5-(3-(2-fluoro-N-propioloylbenzamido)propoxy)-4-methoxy-propiolamidobenzoate (58b)

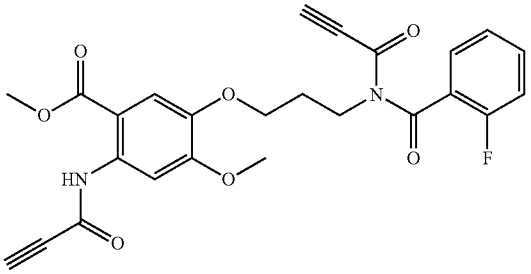 [SMILES: C#CC(=O)Nc1cc(OC)c(OCCCN(C(=O)C#C)C(=O)c2ccccc2F)cc1C(=O)OC]

Following the procedure described for compound 4, reaction of 57b (50 mg, 0.13 mmol), propiolic acid (0.016 mL, 0.27 mmol) and N, N'-dicyclohexylcarbodiimide (55 mg, 0.27 mmol) $CH_2Cl_2$ (15 mL) under $N_2$ afforded 58b (57 mg, 89%). $^1$H NMR (500 MHz, $CDCl_3$) δ 11.71 (s, 1H), 8.38 (s, 1H), 7.88 (s, 1H), 7.86 (td, J=7.6, 1.8 Hz, 1H), 7.48 (m, 1H), 7.16 (t, J=7.2 Hz, 1H), 7.07 (dd, 10.5, 8.4 Hz, 1H), 4.35 (t, J=6.5 Hz, 2H), 3.94 (m, 1H), 3.91 (s, 3H), 3.90 (s, 3H), 3.72 (m, 1H), 2.98 (s, 1H), 2.68 (s, 1H), 2.00 (tt, J=6.5, 7.0 Hz, 2H).

methyl 5-(3-(3-fluoro-N-propioloylbenzamido)propoxy)-4-methoxy-2-propiolamidobenzoate (58c)

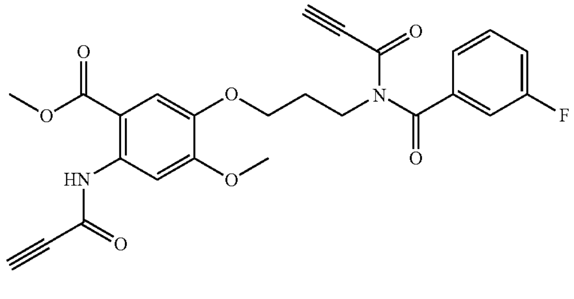 [SMILES: C#CC(=O)Nc1cc(OC)c(OCCCN(C(=O)C#C)C(=O)c2cccc(F)c2)cc1C(=O)OC]

Following the procedure described for compound 4, reaction of 57c (90 mg, 0.24 mmol), propiolic acid (0.029 mL, 0.48 mmol) and N, N'-dicyclohexylcarbodiimide (99 mg, 0.47 mmol) in $CH_2Cl_2$ (15 mL) under $N_2$ afforded 58c (113 mg, 98%). $^1$H NMR (500 MHz, $CDCl_3$) δ 11.71 (s, 1H), 8.39 (s, 1H), 7.75 (d, 7.8 Hz, 1H), 7.61 (ddd, J=9.3, 2.4, 1.5 Hz, 1H), 7.37 (m, 1H), 7.22 (m, 1H), 4.35 (t, J=6.3 Hz, 2H), 3.93 (m, 1H), 3.91 (s, 3H), 1.90 (s, 3H), 3.73 (m, 1H), 2.98 (s, 1H), 2.69 (s, 1H), 1.99 (tt, J=6.3, 6.7 Hz, 2H).

methyl 5-(3-(4-fluoro-N-propioloylbenzamido)propoxy)-4-methoxy-2-propiolamidobenzoate (58d)

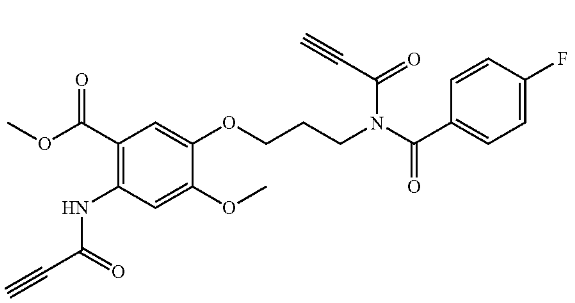 [SMILES: C#CC(=O)Nc1cc(OC)c(OCCCN(C(=O)C#C)C(=O)c2ccc(F)cc2)cc1C(=O)OC]

Following the procedure described for compound 4, reaction of 57d (70 mg, 0.19 mmol), propiolic acid (0.023 mL, 0.37 mmol) and N, N'-dicyclohexylcarbodiimide (77 mg, 0.37 mmol) in $CH_2Cl_2$ (15 mL) under $N_2$ afforded 58d (68 mg, 76%). $^1$H NMR (500 MHz, $CDCl_3$) δ 11.71 (s, 1H), 8.39 (s, 1H), 7.98 (m, 2H), 7.87 (s, 1H), 7.06 (m, 1H), 4.33 (td, J=6.3, 1.6 Hz, 2H), 3.93 (m, 1H), 3.91 (s, 3H), 3.90 (s, 3H), 3.72 (m, 1H), 2.99 (s, 1H), 2.69 (s, 1H), 1.98 (tt, J=6.3, 6.9 Hz, 2H).

methyl 5-(3-(2,6-difluoro-N-propioloylbenzamido)propoxy-4-methoxy-2-propiolamidobenzoate (58e)

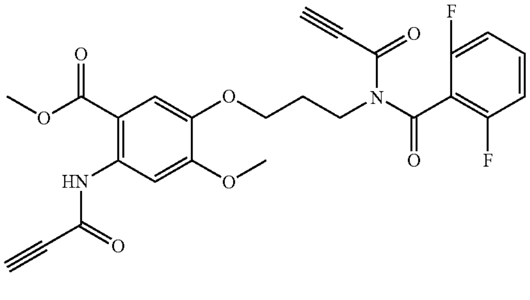 [SMILES: C#CC(=O)Nc1cc(OC)c(OCCCN(C(=O)C#C)C(=O)c2c(F)cccc2F)cc1C(=O)OC]

Following the procedure described for compound 4, reaction of 57e (100 mg, 0.25 mmol), propiolic acid (0.031 mL, 0.51 mmol) and N, N'-dicyclohexylcarbodiimide (105 mg, 0.51 mmol) in $CH_2Cl_2$ (15 mL) under $N_2$ afforded 58e (113 mg, 89%). $^1$H NMR (500 MHz, $CDCl_3$) δ 11.73 (s, 1H), 8.39 (s, 1H), 7.89 (s, 1H), 7.37 (tt, J=8.5, 6.2 Hz, 1H), 6.90 (t, J=8.2 Hz, 2H), 4.38 (t, J=6.3 Hz, 2H), 3.91 (s, 6H), 3.86 (m, 1H), 3.70 (m, 1H), 2.98 (s, 1H), 2.69 (s, 1H), 1.99 (tt, J=6.3, 6.9 Hz, 2H).

methyl 5-(3-(2,6-dimethoxy-N-propioloylbenzamido)propoxy)-4-methoxy-2-propiolamidobenzoate (58f)

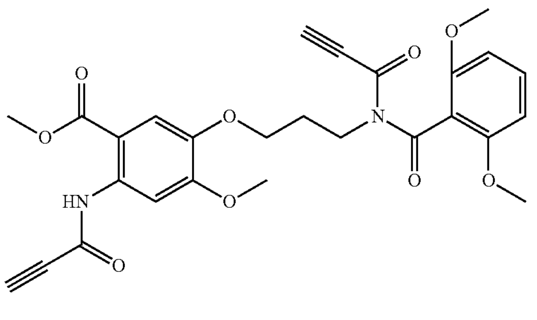

Following the procedure described for compound 4, reaction of 57f (50 mg, 0.12 mmol), propiolic acid (0.015 mL, 0.24 mmol) and N, N'-dicyclohexylcarbodiimide (49 mg 0.24 mmol) in $CH_2Cl_2$ (15 mL) under $N_2$ afforded 58f (61 mg, 98%). $^1$H NMR (500 MHz, $CDCl_3$) δ 11.74 (s, 1H), 8.39 (s, 1H), 7.88 (s, 1H), 7.24 (m, 1H), 6.50 (d, J=8.4 Hz, 2H), 4.34 (t, J=6.3 Hz, 2H), 3.90 (s, 6H), 3.88 (m, 1H), 3.74 (s, 6H), 3.68 (m, 1H), 2.98 (s, 1H), 2.67 (s, 1H), 1.96 (tt, J=6.9, 7.2 Hz, 2H).

methyl 4-methoxy-5-(3-(3-methoxy-N-propioloylbenzamido)propoxy-2-propiolamidobenzoate (58g)

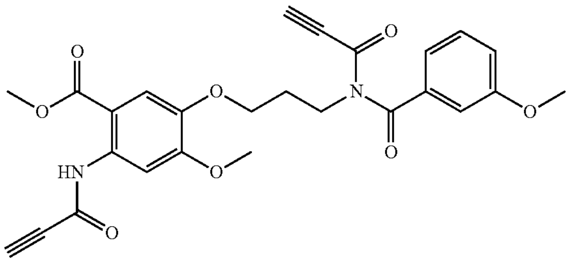

Following the procedure described for compound 4, reaction of 57g (130 mg, 0.33 mmol) propiolic acid (0.041 mL, 0.67 mmol) and N, N'-dicyclohexylcarbodiimide (138 mg, 0.67 mmol) $CH_2Cl_2$ (15 mL) under $N_2$ afforded 58g (127 mg, 77%). $^1$H NMR (500 MHz, $CDCl_3$) δ 11.70 (s, 2H), 8.37 (s, 2H) 7.88 (s, 2H) 7.53 (d, J=7.6 Hz, 1H), 7.45 (dd, J=2.5, 1.6 Hz, 1H), 7.29 (t, J=8.0 Hz, 1H), 7.06 (dd, J=8.6, 2.2 Hz, 1H), 4.33 (t, J=6.4 Hz, 2H), 3.94 (m, 1H), 3.90 (s, 3H), 3.89 (s, 3H), 3.81 (s, 3H), 3.72 (m, 1H), 2.98 (s, 1H), 2.69 (s, 1H), 2.00 (tt, J=6.4, 6.8 Hz, 2H).

4-methoxy-5-(3-(4-methoxy-N-propioloylbenzamido)propoxy)-2-propiolamidobenzoate (58h)

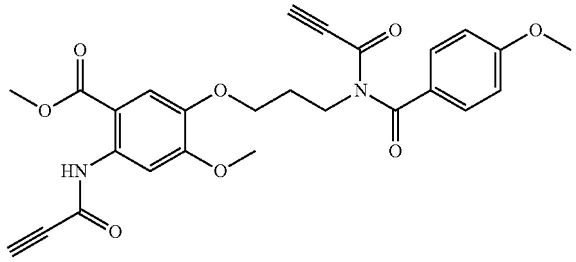

Following the procedure described for compound 4, reaction of 57h (60 mg, 0.15 mmol), propiolic acid (0.019 mL, 0.31 mmol) and N, N'-dicyclohexylcarbodiimide (64 mg, 0.31 mmol) in $CH_2Cl_2$ (15 mL) under $N_2$ afforded 58h (72 mg, 95%). $^1$H NMR (500 MHz, $CDCl_3$) δ 11.71 (s, 1H), 8.37 (s, 1H), 7.89 (m, 3H), 6.86 (d, J=8.8 Hz, 2H), 4.30 (t, J=6.0 Hz, 2H), 3.93 (m, 1H), 3.90 (s, 3H), 3.89 (s, 3H), 3.83 (s, 3H), 3.70 (m, 1H), 2.98 (s, 1H), 2.69 (s, 1H), 1.98 (tt, J=6.0, 6.8 Hz, 2H).

methyl 4-methoxy-5-(3-(N-(2-phenylacetyl)propiolamido)propoxy)-2-propiolamidobenzoate (58i)

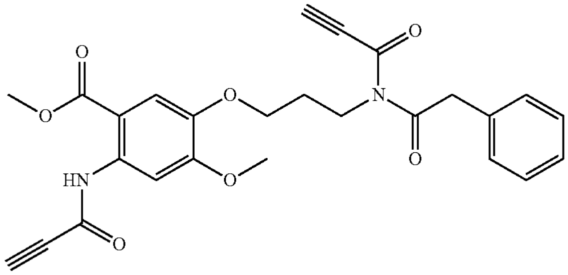 [SMILES: C#CC(=O)Nc1cc(OC)c(OCCCN(C(=O)C#C)C(=O)Cc2ccccc2)cc1C(=O)OC]

Following the procedure described for compound 4, reaction of 57i (50 mg, 0.13 mmol), propiolic acid (0.017 mL, 0.27 mmol) and N, N'-dicyclohexylcarbodiimide (55 mg, 0.27 mmol) in $CH_2Cl_2$ (15 mL) under $N_2$ afforded 58i (63 mg, 98%). $^1$H NMR (500 MHz, $CDCl_3$) δ 11.75 (s, 1H), 8.39 (s, 1H), 7.85 (s, 1H), 7.26 (m, 5H), 4.11 (t, J=6.3 Hz, 2H), 3.91 (s, 3H), 3.88 (s, 3H), 3.78 (m, 1H), 3.56 (s, 2H), 3.55 (m, 1H), 3.00 (s, 1H), 2.70 (s, 1H), 1.83 (tt, J=6.3, 6.8 Hz, 2H).

methyl-5-(3-(N-(2-(2-fluorophenyl)acetyl)propiolamido)propoxy-4-methoxy-2-propiolamidobenzoate (58j)

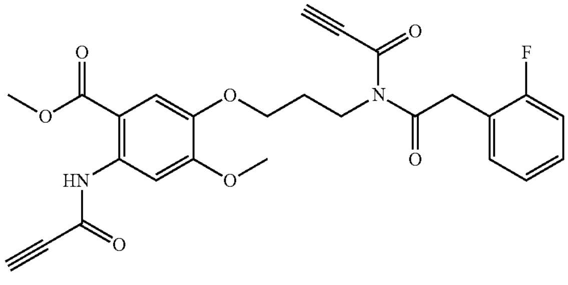

Following the procedure described for compound 4, reaction of 57j (50 mg, 0.13 mmol), propiolic acid (0.018 mL, 0.26 mmol) and N, N'-dicyclohexylcarbodiimide (53 mg, 0.26 mmol) in $CH_2Cl_2$ (15 mL) under $N_2$ afforded 58j (58 mg, 92%). $^1$H NMR (500 MHz, $CDCl_3$) δ 11.75 (s, 1H) 8.40 (s, 1H), 7.86 (s, 1H), 7.21 (m, 2H), 7.05 (m, 1H), 6.98 (d, J=9.1 Hz, 1H), 4.13 (t, J=6.3, 2.2 Hz, 2H), 3.91 (s, 3H), 3.89 (s, 3H), 3.79 (m, 1H), 3.61 (s, 2H), 3.56 (m, 1H), 2.99 (s, 1H), 2.68 (s, 1H), 1.84 (tt, J=6.3, 6.8 Hz, 2H).

methyl 5-(3-(N-(2-(3-fluorophenyl)acetyl)propiolamido)propoxy)-4-methoxy-2-propiolamidobenzoate (58k)

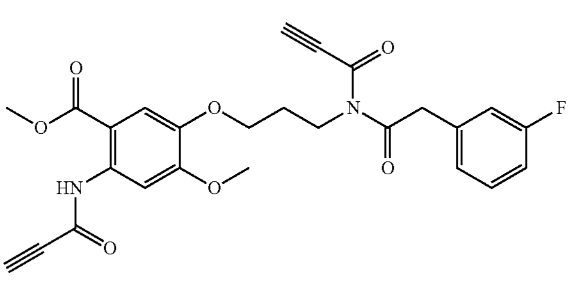 [SMILES: C#CC(=O)Nc1cc(OC)c(OCCCN(C(=O)C#C)C(=O)Cc2cccc(F)c2)cc1C(=O)OC]

Following the procedure described for compound 4, reaction of 57k (65 mg, 0.17 mmol), propiolic acid (0.020 mL, 0.33 mmol) and N, N'-dicyclohexylcarbodiimide (69 mg, 0.33 mmol) in $CH_2Cl_2$ (15 mL) under $N_2$ afforded 58k (79 mg, 96%). $^1$H NMR (500 MHz, $CDCl_3$) δ 11.74 (s, 1H), 8.39 (s, 1H), 7.85 (s, 1H), 7.23 (m, 1H), 6.99 (d, 7.5 Hz, 1H), 6.92 (m, 2H), 4.12 (t, J=6.0 Hz, 2H), 3.91 (s, 3H), 3.89 (s, 3H), 3.78 (m, 1H), 3.56 (m, 3H), 2.99 (s, 1H), 2.68 (s, 1H), 1.84 (tt, J=6.0, 6.9 Hz, 2H).

methyl 5-(3-(N-(2-(4-fluorophenylacetyl)propiolamido)propoxy)-4-methoxy-2-propiolamidobenzoate (58l)

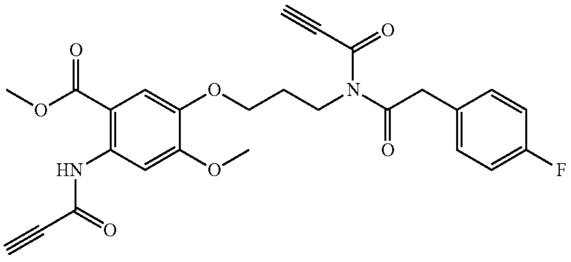 [SMILES: C#CC(=O)Nc1cc(OC)c(OCCCN(C(=O)C#C)C(=O)Cc2ccc(F)cc2)cc1C(=O)OC]

Following the procedure described for compound 4, reaction of 57l (90 mg, 0.23 mmol), propiolic acid (0.028 mL, 0.46 mmol) and N, N'-dicyclohexylcarbodiimide (95 mg, 0.46 mmol) in $CH_2Cl_2$ (15 mL) under $N_2$ afforded 58l (112 mg, 98%). $^1$H NMR (500 MHz, $CDCl_3$) δ 11.74 (s, 2H), 8.40 (s, 1H), 7.84 (s, 1H), 7.18 (dd, J=8.5, 5.4 Hz, 2H), 6.95 (t, J=8.7 Hz, 2H), 4.11 (t, J=6.3 Hz, 2H), 3.91 (s, 3H), 3.89 (s, 3H), 3.77 (m, 1H), 3.57 (m, 1H), 3.54 (s, 2H), 2.99 (s, 1H), 2.68 (s, 1H), 1.83 (tt, J=6.8 Hz, 2H).

methyl 4-methoxy-5-(3-(N-(2-(2-methoxyphenyl)acetyl)propiolamido)propoxy-2-propiolamidobenzoate (58m)

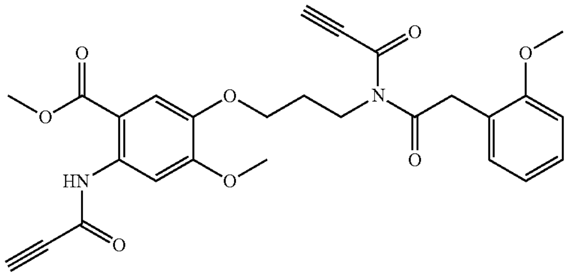

Following the procedure described for compound 4, reaction of 57m (50 mg, 0.12 mmol), propiolic acid (0.015 mL, 0.25 mmol) and N, N'-dicyclohexylcarbodiimide (51 mg, 0.25 mmol) $CH_2Cl_2$ (15 mL) under $N_2$ afforded 58m (49 mg, 78%). $^1$H NMR (500 MHz, $CDCl_3$) δ 11.75 (s, 1H), 8.39 (s, 1H), 7.86 (s, 1H), 7.20 (td, J=3.9, 1.5 Hz, 1H), 7.11 (dd, J=7.4, 1.4 Hz, 1H), 6.85 (m, 1H), 6.81 (d, J=8.3 Hz, 1H), 4.11 (td, J=6.3, 2.1 Hz, 2H), 3.90 (s, 3H), 3.89 (s, 3H), 3.80 (m, 1H), 3.75 (s, 3H), 3.56 (s, 2H), 3.59 (m, 1H), 2.99 (s, 1H), 2.68 (s, 1H), 1.83 (tt, J=6.3, 6.8 Hz, 2H).

methyl 4-methoxy-5-(3-(N-(2-(3-methoxyphenyl)acetyl)propiolamido)propoxy)-2-propiolamidobenzoate (58n)

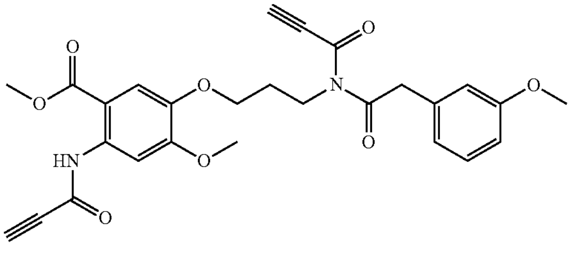

Following the procedure described for compound 4, reaction of 57n (65 mg, 0.16 mmol), propiolic acid (0.020 mL, 0.32 mmol) and N, N'-dicyclohexylcarbodiimide (67 mg, 0.32 mmol) $CH_2Cl_2$ (15 mL) under $N_2$ afforded 58n (70 mg, 86%). $^1$H NMR (500 MHz, $CDCl_3$) δ 11.74 (s, 1H), 8.39 (s, 1H), 7.84 (s, 1H), 7.17 (dd, J=8.9, 7.7 Hz, 1H), 6.78 (m, 3H), 4.11 (t, J=6.3 Hz, 2H), 3.91 (s, 3H), 3.89 (s, 3H), 3.79 (m, 1H), 3.76 (s, 3H), 3.57 (m, 1H), 3.53 (s, 2H), 2.99 (s, 2H), 2.68 (s, 2H), 1.84 (tt, J=6.3, 6.8 Hz, 2H).

methyl 4-methoxy-5-(3-(N-(2-(4-methoxyphenyl) acetyl)propiolamido)propoxy)-2-propiolamidobenzoate (58o)

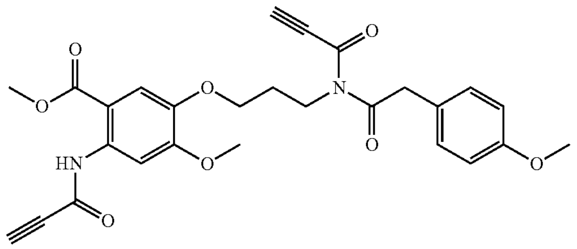

Following the procedure described for compound 4, reaction of 57o (90 mg, 0.22 mmol), propiolic acid (0.028 mL, 0.45 mmol) and N, N'-dicyclohexylcarbodiimide (92 mg, 0.45 mmol) in $CH_2Cl_2$ (15 mL) under $N_2$ afforded 58o (80 mg, 71%). $^1H$ NMR (500 MHz, $CDCl_3$) δ 11.74 (s, 1H), 8.39 (s, 1H), 7.85 (s, 1H), 7.12 (d, J=8.6 Hz, 2H), 6.79 (m, 2H), 4.10 (t, 6.3 Hz, 2H), 3.91 (s, 3H), 3.89 (s, 3H), 3.80 (m, 1H), 3.76 (s, 3H), 3.56 (m, 1H), 4.49 (s, 2H), 2.99 (s, 1H), 2.68 (s, 1H), 1.83 (tt, J=6.3, 6.7 Hz, 2H).

methyl 4-methoxy-2-propiolamido-5-(3-(N-(2-(3,4,5-trimethoxyphenyl)acetyl)propiolamido)propoxy) benzoate (58p)

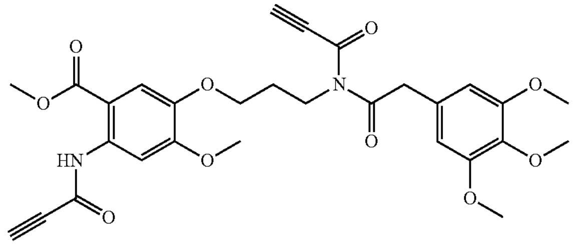

Following the procedure described for compound 4, reaction of 57p (75 mg, 0.16 mmol), propiolic acid (0.020 mL, 0.32 mmol) and N, N'-dicyclohexylcarbodiimide, (67 mg, 0.32 mmol) in $CH_2Cl_2$ (15 mL) under $N_2$ afforded 58p (80 mg, 87%). $^1H$ NMR (500 MHz, $CDCl_3$) δ 11.73 (s, 1H), 8.40 (s, 1H), 7.86 (s, 1H), 6.47 (s, 2H), 4.12 (t, J=6.3 Hz, 2H), 3.91 (s, 3H), 3.90 (s, 3H), 3.82 (m, 7H), 3.80 (s, 3H), 3.60 (m, 1H), 3.51 (s, 2H), 2.99 (s, 1H), 2.68 (s, 1H), 1.84 (tt, J=6.3, 6.7 Hz, 2H).

methyl 5-(3-(N-(2-(2-chlorophenyl)acetyl)propiolamido)propoxy-4-methoxy-2-propiolamidobenzoate (58q)

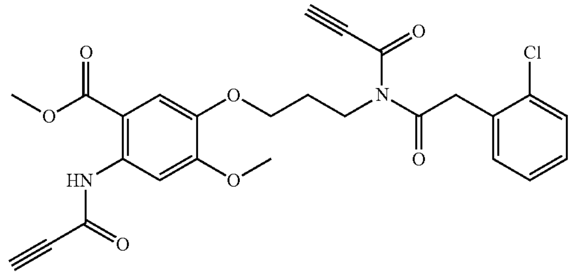 [SMILES: C#CC(=O)Nc1cc(OC)c(OCCCN(C(=O)C#C)C(=O)Cc2ccccc2Cl)cc1C(=O)OC]

Following the procedure described for compound 4, reaction of 57q (80 mg, 0.20 mmol), propiolic acid (0.024 mL, 0.39 mmol) and N, N'-dicyclohexylcarbodiimide (81 mg, 0.39 mmol) $CH_2Cl_2$ (15 mL) under $N_2$ afforded 58q (100 mg, 99%). $^1H$ NMR (500 MHz, $CDCl_3$) δ 11.75 (s, 1H), 8.40 (s, 1H), 7.85 (s, 1H), 7.30 (dd, J=5.6, 3.6 Hz, 1H), 7.22 (m, 1H), 7.18 (m, 2H), 4.13 (t, J=6.1 Hz, 2H), 3.91 (s, 3H), 3.89 (s, 3H), 3.78 (m, 1H), 3.70 (s, 2H), 3.56 (m, 1H), 2.99 (s, 1H), 2.68 (s, 1H), 1.85 (tt, J=6.1, 6.7 Hz, 2H).

methyl 5-(3-(N-(2-(3-chlorophenyl)acetyl)propiolamido)propoxy)-4-methoxy-2-propiolamidobenzoate (58r)

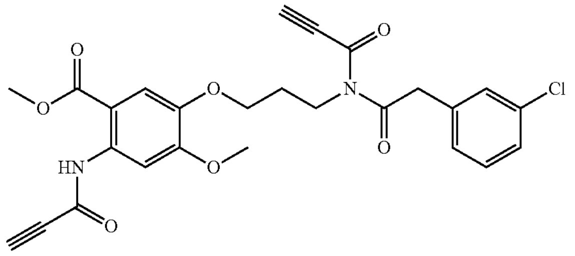 [SMILES: C#CC(=O)Nc1cc(OC)c(OCCCN(C(=O)C#C)C(=O)Cc2cccc(Cl)c2)cc1C(=O)OC]

Following the procedure described for compound 4, reaction of 57r (75 mg, 0.18 mmol), propiolic acid (0.023 mL, 0.37 mmol) and N, N'-dicyclohexylcarbodiimide (76 mg, 0.37 mmol) in $CH_2Cl_2$ (15 mL) under $N_2$ afforded 58r (84 mg, 89%). $^1H$ NMR (500 MHz, $CDCl_3$) δ 11.74 (s, 1H), 8.39 (s, 1H), 7.85 (s, 1H), 7.21 (s, 1H), 7.19 (m, 2H), 7.10 (m, 1H), 4.12 (t, J=6.4 Hz, 2H), 3.91 (s, 3H), 3.89 (s, 3H), 3.78 (m, 1H), 3.57 (m, 1H), 3.54 (s, 2H), 2.99 (s, 1H), 2.68 (s, 1H), 1.84 (tt, J=6.4, 6.8 Hz, 2H).

methyl 4-methoxy-2-propiolamido-5-(3-(N-(2-(2-(trifluoromethyl)phenyl)acetyl)propiolamido) propoxy)benzoate (58s)

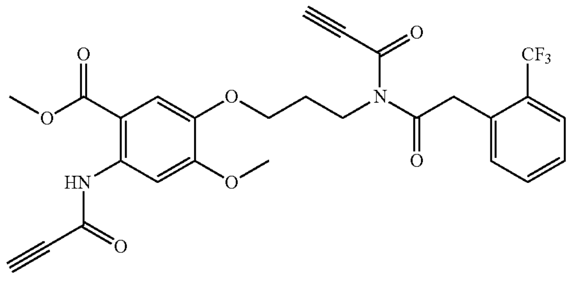

Following the procedure described for compound 4, reaction of 57s (100 mg, 0.23 mmol), propiolic acid (0.028 mL, 0.45 mmol) and N, N'-dicyclohexylcarbodiimide, (94 mg, 0.45 mmol) in $CH_2Cl_2$ (15 mL) under $N_2$ afforded 58s (116 mg, 94%), $^1H$ NMR (500 MHz, $CDCl_3$) δ 11.75 (s, 1H), 8.39 (s, 1H), 7.85 (s, 1H), 7.59 (d, J=7.8 Hz, 1H), 7.47 (t, J=7.7 Hz, 1H), 7.34 (t, J=7.4 Hz, 2H), 4.12 (t, J=6.0 Hz, 2H), 3.91 (s, 3H), 3.89 (s, 3H), 3.76 (m, 3H), 3.55 (m, 1H), 2.99 (s, 2H), 2.68 (s, 2H), 1.83 (tt, J=6.0, 6.8 Hz, 2H).

methyl 4-methoxy-2-propiolamido-5-(3-(N-(2-(3-(trifluoromethyl)phenyl)acetyl)propiolamido) propoxy)benzoate (58t)

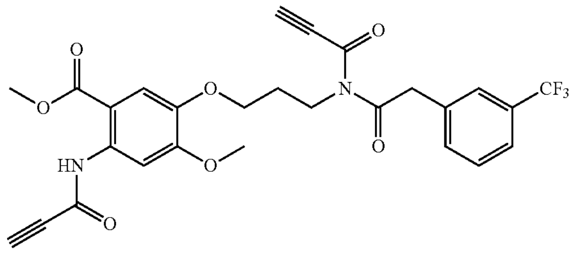 [SMILES: C#CC(=O)Nc1cc(OC)c(OCCCN(C(=O)C#C)C(=O)Cc2cccc(C(F)(F)F)c2)cc1C(=O)OC]

Following the procedure described for compound 4, reaction of 57t (75 mg, 0.17 mmol), propiolic acid (0.021 mL, 0.34 mmol) and N, N'-dicyclohexylcarbodiimide (70 mg, 0.34 mmol) in $CH_2Cl_2$ (15 mL) under $N_2$ afforded 58t (92 mg, 99%). $^1$H NMR (500 MHz, $CDCl_3$) δ 11.74 (s, 1H), 8.40 (s, 1H), 7.85 (s, 1H), 7.49 (m, 2H), 7.41 (m, 2H), 7.34 (t, J=7.4 Hz, 2H), 4.13 (t, J=6.3 Hz, 2H), 3.91 (s, 3H), 3.89 (s, 3H), 3.78 (m, 1H) 3.64 (s, 2H) 3.59 (m, 1H), 2.99 (s, 1H), 2.68 (s, 1H), 1.84 (tt, J=6.3, 6.8 Hz, 2H).

methyl 4-methoxy-2-propiolamido-5-(3-(N-(2-(4-(trifluoromethyl)phenyl)acetyl)propiolamido) propoxy)benzoate (58u)

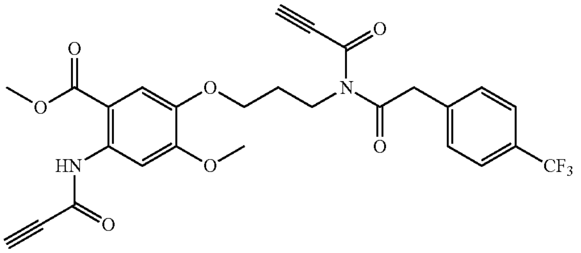 [SMILES: C#CC(=O)Nc1cc(OC)c(OCCCN(C(=O)C#C)C(=O)Cc2ccc(C(F)(F)F)cc2)cc1C(=O)OC]

Following the procedure described for compound 4, reaction of 57u (102 mg, 0.23 mmol), propiolic acid (0.029 mL, 0.46 mmol) and N, N'-dicyclohexylcarbodiimide (96 mg, 0.46 mmol) in $CH_2Cl_2$ (15 mL) under $N_2$ afforded 58u (115 mg, 91%). $^1$H NMR (500 MHz, $CDCl_3$) δ 11.74 (s, 1H), 8.41 (s, 1H), 7.86 (s, 1H), 7.54 (d, J=8.2 Hz, 2H), 7.35 (d, J=8.0 Hz, 2H), 4.13 (t, J=6.3 Hz, 2H), 3.91 (s, 3H), 3.90 (s, 3H), 3.79 (m, 1H), 3.64 (d, 2H), 3.60 (m, 1H), 2.99 (s, 1H), 2.69 (s, 1H), 1.83 (tt, J=6.3, 6.8 Hz, 2H).

methyl 4-methoxy-2-propiolamido-5-(3-(N-propioloyloxazole-5-carboxamido)propoxy)benzoate (58v)

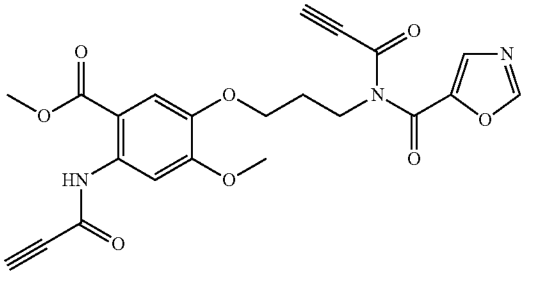 [SMILES: C#CC(=O)Nc1cc(OC)c(OCCCN(C(=O)C#C)C(=O)c2cnco2)cc1C(=O)OC]

Following the procedure described for compound 4, reaction of 57v (100 mg, 0.29 mmol), propiolic acid (0.035 mL, 0.57 mmol) and N, N'-dicyclohexylcarbodiimide (118 mg, 0.57 mmol) in $CH_2Cl_2$ (15 mL) under $N_2$ afforded 58v (118 mg, 91%). $^1$H NMR (500 MHz, $CDCl_3$) δ 11.72 (s, 1H), 8.40 (s, 1H), 7.97 (s, 1H), 7.89 (s, 1H), 7.72 (s, 1H), 4.37 (t, J=6.4 Hz, 2H), 3.91 (s, 6H), 3.87 (m, 1H), 3.70 (m, 1H), 2.99 (s, 1H), 2.69 (s, 1H), 1.97 (tt, J=6.3, 6.8 Hz, 2H), Scheme 18

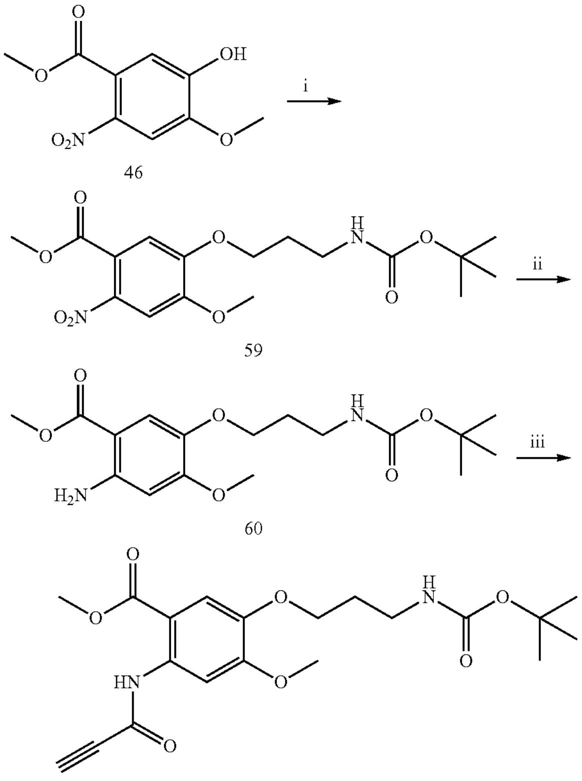

46

59

60

61

Reagents and conditions: (i) 3-(boc-amino)-1-propanol, DIAD, $Ph_3P$, THF, RT; (ii) Zn, AcOH, THF, RT; (iii) propiolic acid, DCC, $CH_2Cl_2$, 0° C.

methyl 5-(3-((tert-butoxycarbonyl)amino)propoxy)-4-methoxy-2-nitrobenzoate (59)

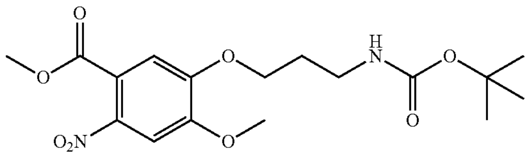 [SMILES: COC(=O)c1cc(OCCCNC(=O)OC(C)(C)C)c(OC)cc1[N+](=O)[O-]]

To a solution of 46 (300 mg, 1.32 mmol) and triphenylphosphine (692 mg, 2.64 mmol) in dry THF (30 mL) was added 3-(boc-amino)-1-propanol (0.270 mL, 1.58 mmol) and diisopropyl azodicarboxylate (6.93 mL, 35.19 mmol) dropwise in an ice-bath. The resulting solution was stirred under $N_2$ at RT for 6 h. The reaction mixture was suspended in $H_2O$ (150 mL) and then extracted with EtOAc (3×150 mL). The combined organic layer was dried over $MgSO_4$, filtered and concentrated in vacuo. The residue was purified by silica gel chromatography (EtOAc/n-hexane=1:3) to afford 59 (500 mg, 99%). $^1H$ NMR (300 MHz, $CDCl_3$) δ 7.43 (s, 1H), 7.04 (s, 1H), 5.18 (s, 1H), 4.16 (t, J=5.9 Hz, 2H), 3.95 (s, 3H), 3.88 (s, 3H), 3.34 (m, 2H), 2.04 (m, 2H), 1.43 (m, 9H).

methyl 2-amino-5-(3-((tert-butoxycarbonyl)amino) propoxy)-4-methoxybenzoate (60)

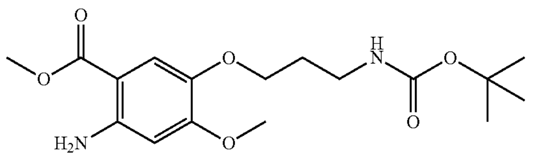

Following the procedure described for compound 38, reaction of 59 (50 mg, 0.13 mmol) in HOAc/THF=1:4 (10 mL) was added Zn (85 mg, 1.30 mmol) and the mixture was stirred at RT under $N_2$ to afford 60 (33 mg, 72%). $^1H$ NMR (300 MHz, $CDCl_3$) δ 7.29 (s, 1H), 7.11 (s, 1H), 5.58 (s, 2H), 5.45 (s, 2H), 3.99 (t, J=5.8 Hz, 2H), 3.84 (s, 3H), 3.82 (s, 3H), 3.33 (m, 2H), 1.94 (m, 2H), 1.43 (s, 9H).

Methyl 5-(3-((tert-butoxycarbonyl)amino)propoxy)-4-methoxy-2-propiolamidobenzoate (61)

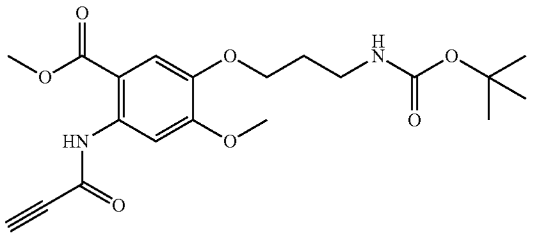 [SMILES: C#CC(=O)Nc1cc(OC)c(OCCCNC(=O)OC(C)(C)C)cc1C(=O)OC]

Following the procedure described for compound 4, reaction of 60 (33 mg, 0.09 mmol) in dry $CH_2Cl_2$ (10 mL) was added propiolic acid (0.009 mL, 0.14 mmol) and N, N'-dicyclohexylcarbodiimide (29 mg, 0.14 mmol) in dry $CH_2Cl_2$ (5 mL) dropwise in an ice-bath to afford 61 (37 mg, 98%). $^1H$ NMR (300 MHz, $CDCl_3$) δ 11.56 (s, 1H), 8.32 (s, 1H), 7.44 (s, 2H), 4.07 (t, J=5.6 Hz, 2H), 3.93 (s, 3H), 3.90 (s, 3H), 3.35 (m, 2H), 1.99 (m, 2H), 1.43 (s, 9H).

Scheme 19

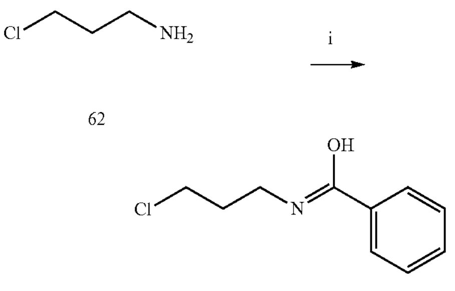

62

63

-continued

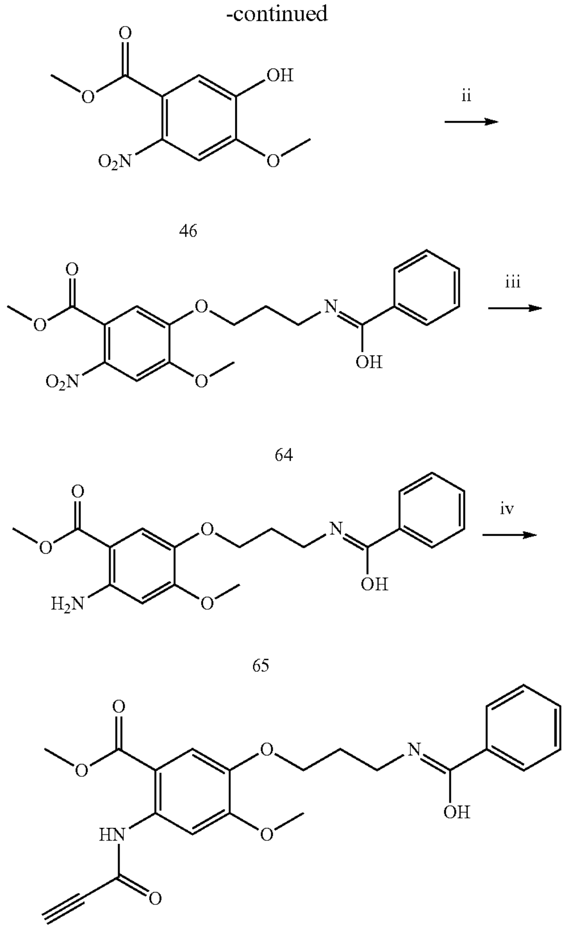

46

64

65

66

Reagents and conditions: benzoic acid, DCC, $CH_2Cl_2$, RT; (ii) $K_2CO_3$, DMF, 100° C: (iii) Zn, AcOH, THF, RT; (iv) propiolic acid, DCC, $CH_2Cl_2$, 0° C.

(Z)—N-(3-chloropropyl)benzimidic acid (63)

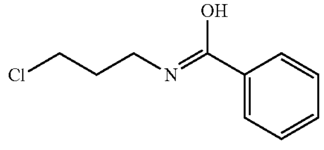 [SMILES: O/C(=N\CCCCl)c1ccccc1]

To a solution of 62 (100 mg, 0.77 mmol) in dry $CH_2Cl_2$ (10 mL) was added benzoic acid (140 mg 1.12 mmol) and N, N'-dicyclohexylcarbodiimide (238 mg, 1.15 mmol) in dry $CH_2Cl_2$ (5 mL) dropwise in an ice-bath. The resulting solution was stirred under $N_2$ at RT for 12 h. The reaction mixture was suspended in $H_2O$ (50 mL) and then extracted with EtOAc (3×50 mL). The combined organic layer was dried over $MgSO_4$, filtered and concentrated in vacuo. The mixture was filtered and washed with EtOAc/n-hexane=1:1 (10 mL). The residue was purified by silica gel chromatography (EtOAc/n-hexane=1:3) to afford 63 (142 mg, 93%).

$^1$H NMR (300 MHz, $CDCl_3$) δ 7.74 on, 2H), 7.45 (m, 3H), 6.38 (s, 1H), 3.62 (m, 4H), 2.11 (m, 2H).

(Z)—N-(3-(2-methoxy-5-(methoxycarbonyl)-4-nitrophenoxy)propyl)benzimidic acid (64)

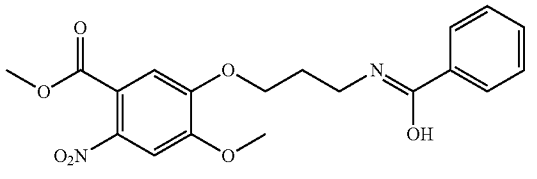

Following the procedure described for compound 2, reaction of 46 (1.72 g, 7.59 mmol) and $K_2CO_3$ (2.10 g, 15.17 mmol) in DMF (150 mL) was added 63 (1.50 g, 7.59 mmol). The resulting solution was heated to 100° C. under $N_2$ to afford 64 (359 mg, 12%). $^1$H NMR (300 MHz, $CDCl_3$) δ 7.78 (m, 2H), 7.45 (m, 4H), 7.08 (s, 1H), 6.91 (s, 1H), 4.25 (t, J=5.7 Hz, 2H), 3.88 (s, 3H), 3.76 (s, 3H), 3.70 (m, 2H), 2.19 (m, 2H).

(Z)—N-(3-(4-amino-2-methoxy-5-(methoxycarbonyl)phenoxy)propyl)benzimidic acid (65)

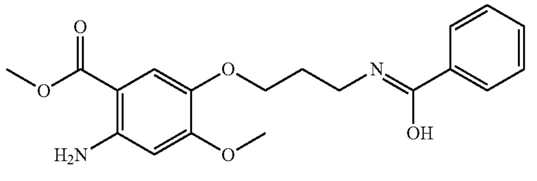 [SMILES: COC(=O)c1cc(OCCC/N=C(\O)c2ccccc2)c(OC)cc1[N+](=O)[O-]]

Following the procedure described for compound 38, reaction of 64 (80 mg, 0.21 mmol) in HOAc/THF=1:4 (10 mL) was added Zn (134 mg, 2.06 mmol) and the mixture was stirred at RT under $N_2$ to afford 65 (69 mg, 93%). $^1$H NMR (300 MHz, $CDCl_3$) δ 7.80 (m, 2H), 7.42 (m, 3H), 7.33 (s, 1H), 7.29 (s, 1H), 6.10 (s, 1H), 5.60 (s, 2H), 4.10 (t, J=5.5 Hz, 2H), 3.82 (s, 3H), 3.69 (m, 2H), 3.62 (s, 3H), 2.09 (m, 2H).

(Z)—N-(3-(2-methoxy-5-(methoxycarbonyl)-4-propiolamidophenoxy)propyl)benzimidic acid (66)

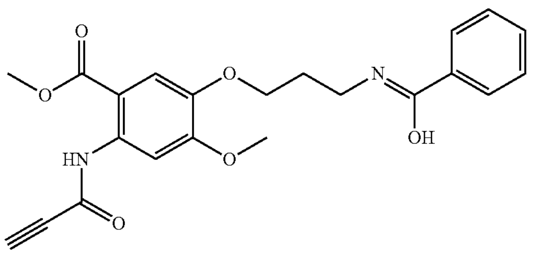 [SMILES: C#CC(=O)Nc1cc(OC)c(OCCC/N=C(\O)c2ccccc2)cc1C(=O)OC]

Following the procedure described for compound 4, reaction of 65 (35 mg, 0.10 mmol) in dry $CH_2Cl_2$ (10 mL) was added propiolic acid (0.010 mL, 0.15 mmol) and N, N'-dicyclohexylcarbodiimide (30 mg, 0.15 mmol) in dry $CH_2Cl_2$ (5 mL) dropwise in an ice-bath to afford 66 (26 mg, 65%). $^1$H NMR (300 MHz, $CDCl_3$) δ 11.54 (s, 2H), 8.30 (s, 1H), 7.79 (m, 2H), 7.44 (m, 4H), 7.16 (s, 1H), 4.17 (t, J=5.5 Hz, 2H), 3.90 (s, 3H), 3.70 (m, 5H), 2.92 (s, 2H), 2.14 (m, 2H).

Scheme 20

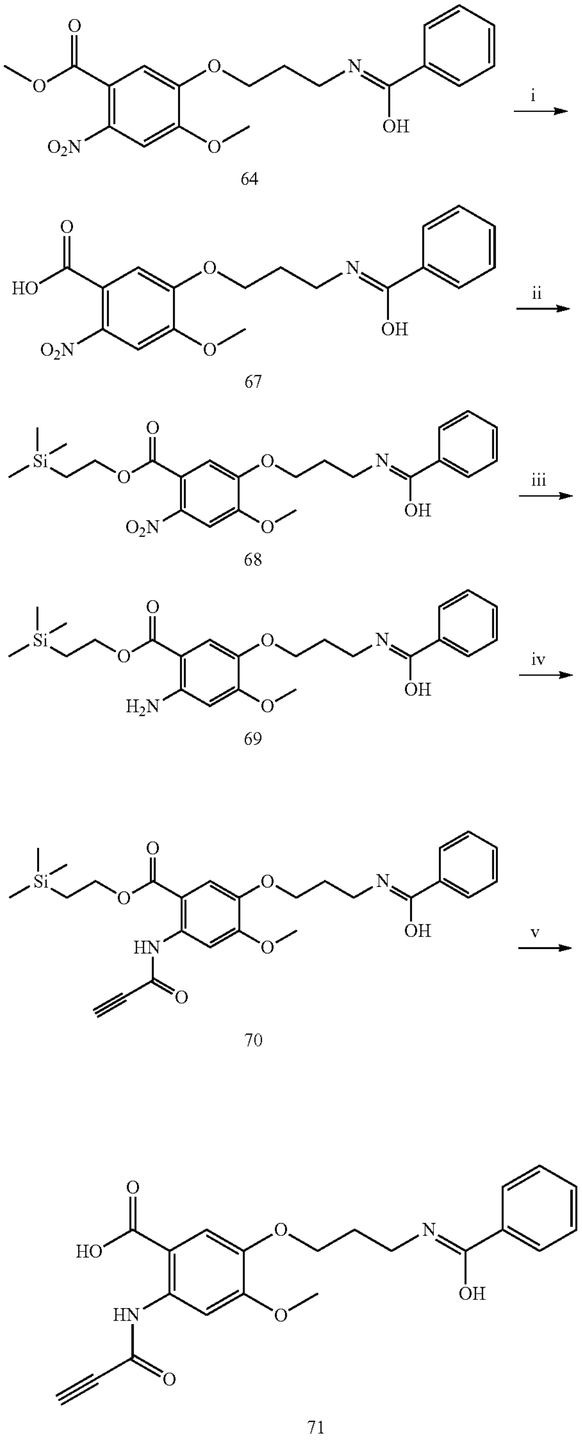

Reagents and conditions: (i) NaOH, MeOH, THF, RT; (ii) $(CH_3)_2Si(CH_2)_2OH$, $Ph_3P$, DIAD, THF, RT; (iii) Zn, AcOH, THF, RT; (iv) propiolic acid, DCC, $CH_2Cl_2$, 0° C.; (v) TBAF, THF, RT.

(Z)-5-(3-((hydroxy(phenyl)methylene)amino) propoxy-4-methoxy-2-nitrobenzoic acid (67)

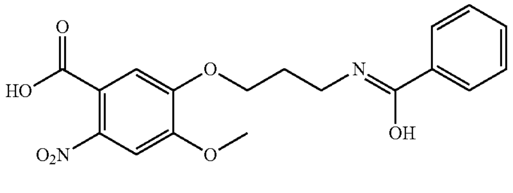 [SMILES: COc1cc([N+](=O)[O-])c(C(=O)O)cc1OCCC/N=C(\O)c1ccccc1]

To a solution of 64 (229 mg, 0.59 mmol) in MeOH (20 mL) and THF (20 mL) was added 5N NaOH (2.5 mL) in an ice-bath. The reaction mixture was stirred at RT under $N_2$ for 8 h. The resulting solution was acidified to pH 2 and extracted with 1N HCl (50 mL) and EtOAc (3×50 mL). The combined organic layer was dried over $MgSO_4$, filtered and concentrated in vacuo. The residue was recrystallized to afford 67 (220 mg, 99%). $^1$H NMR (300 MHz, MeOD) δ 7.84 (m, 2H), 7.52 (m, 4H), 7.31 (s, 1H), 4.28 (t, J=6.0 Hz, 2H), 3.88 (s, 3H), 3.64 (t, J=6.6 Hz, 2H), 2.19 (m, 2H).

(Z)—N-(3-(2-methoxy-4-nitro-5-((2-(trimethylsilyl) ethoxy)carbonyl)phenoxy)propyl)benzimidic acid (68)

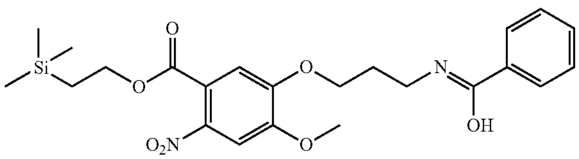

To a solution of 67 (210 mg, 0.56 mmol) and triphenylphosphine (294 mg, 1.12 mmol) in dry THF (30 mL) was added 2-trimethylsilyl)ethanol (0.097 mL, 0.67 mmol) and diisopropyl azodicarboxylate (0.133 mL, 0.67 mmol) dropwise in an ice-bath. The resulting solution was stirred under $N_2$ for 3 h. The reaction mixture was suspended in $H_2O$ (100 mL) and then extracted with EtOAc (3×100 mL). The combined organic layer was dried over $MgSO_4$, filtered and concentrated in vacuo. The residue was purified by silica gel chromatography (EtOAc/n-hexane=1:2) to afford 68 (221 mg, 83%). $^1$H NMR (300 MHz, $CDCl_3$) δ 7.78 (m, 2H), 7.47 (m, 3H), 7.39 (s, 1H), 7.07 (s, 1H), 6.91 (s, 1H), 4.38 (m, 2H), 4.25 (t, J=5.7 Hz, 2H), 3.75 (s, 3H), 3.71 (m, 2H), 2.19 (m, 2H), 1.07 (m, 2H), 0.04 (s, 9H).

(Z)—N-(3-(4-amino-2-methoxy-5-((2-(trimethylsilyl)ethoxy)carbonyl)phenoxy)propyl)benzimidic acid (69)

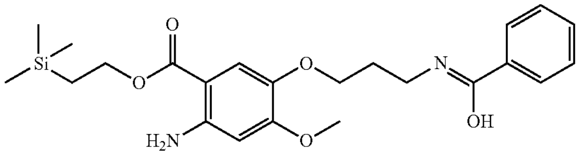 [SMILES: COc1cc([N+](=O)[O-])c(C(=O)OCC[Si](C)(C)C)cc1OCCC/N=C(\O)c1ccccc1]

Following the procedure described for compound 38, reaction of 68 (50 mg, 0.11 mmol) in HOAc/THF=1:4 (10 mL) was added Zn (69 mg, 1.05 mmol) and the mixture was stirred at RT under $N_2$ to afford 69 (40 mg, 85%). $^1$H NMR (300 MHz, $CDCl_3$) δ 7.80 (m, 2H), 7.42 (m, 3H), 7.34 (s, 1H), 7.31 (s, 1H), 6.09 (s, 1H), 5.60 (s, 2H), 4.33 (m, 2H), 4.09 (t, J=7.1 Hz, 2H), 3.69 (m, 2H), 3.61 (s, 3H), 2.09 (m, 2H), 1.09 (m, 2H), 0.06 (m, 9H).

(Z)—N-(3-(2-methoxy-4-propiolamido-5-((2-(trimethylsilyl)ethoxy)carbonyl)phenoxy)propyl)benzimidic acid (70)

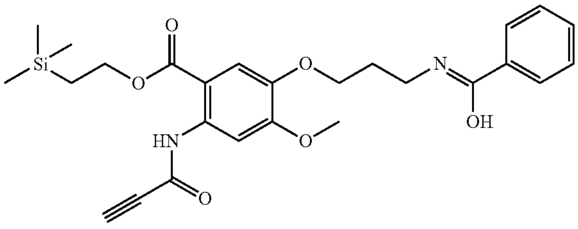 [SMILES: C#CC(=O)Nc1cc(OC)c(OCCC/N=C(\O)c2ccccc2)cc1C(=O)OCC[Si](C)(C)C]

Following the procedure described for compound 4, reaction of 69 (170 mg, 0.38 mmol) in dry $CH_2Cl_2$ (10 mL) was added propiolic acid (0.035 mL, 0.15 mmol) and N, N'-dicyclohexylcarbodiimide (118 mg, 0.57 mmol) in dry $CH_2Cl_2$ (5 mL) dropwise in an ice-bath to afford 70 (180 mg, 95%). $^1$H NMR (300 MHz, $CDCl_3$) δ 11.64 (s, 1H), 8.31 (s, 1H), 7.80 (m, 2H), 7.43 (m, 4H), 7.17 (s, 2H), 4.40 (m, 2H), 4.17 (t, J=5.5 Hz 2H), 3.71 (m, 5H), 2.91 (s, 1H), 2.14 (m, 2H), 1.13 (m, 2H), 0.07 (s, 9H).

(Z)-5-(3-((hydroxy(phenyl)methylene)amino) propoxy)-4-methoxy-2-propiolamidobenzoic acid (71)

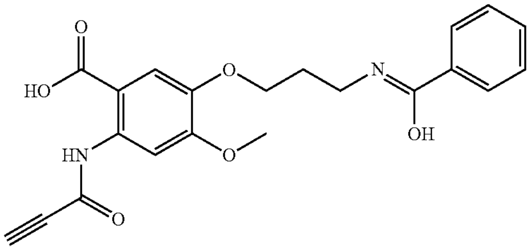 [SMILES: C#CC(=O)Nc1cc(OC)c(OCCC/N=C(\O)c2ccccc2)cc1C(=O)O]

To a solution of 70 (50 mg, 0.10 mmol) in dry THF (2 mL) was added TBAF (1M in THF, 0.50 mL, 0.50 mmol) dropwise at RT. The resulting solution was stirred under $N_2$ for 12 h. The reaction mixture was extracted with 1 N $HCl_{(aq)}$ (50 mL) and EtOAc (3×50 mL). The combined organic layer was dried over $MgSO_4$, filtered and concentrated in vacuo. The residue was purified by silica gel chromatography (MeOH/$CH_2Cl_2$=3:97) to afford 71 (19 mg, 48%). $^1$H NMR (300 MHz, DMSO) δ 11.87 (s, 1H), 8.52 (t, J=5.5 Hz, 1H), 8.08 (s, 1H), 7.83 (m, 2H), 7.48 (m, 3H), 4.47 (s, 1H), 4.04 (t, J=6.2 Hz, 2H), 3.80 (s, 3H), 3.02 (m, 2H), 1.98 (m 2H).

PDIA4 Assay

Recombinant PDI proteins PDIA4 (23 pM) was incubated with insulin (0.2 mM) and DTT (0.1 mM) in the presence of vehicle and compounds at the indicated doses for 30 min at 25° C. The mixture was, measured using a SpectraMax i3x reader at 595 nm based on the manufacturer's instructions (Molecular device, CA, USA). Inhibition of the enzymatic activity PDIA4 is calculated by the formula, 100%×($OD_{595}$ of vehicle−$OD_{595}$ of CP)/($OD_{595}$ of vehicle) as published previously.

Glucose-Stimulated Insulin Secretion

Min6 cells were grown in complete Dulbecco's modified Eagle medium (DMEM) medium containing 10% fetal bovine serum, 100 units/ml penicillin and 100 g/ml streptomycin in a 5% CO2 incubator in the presence of 3.3 mM glucose unless indicated otherwise. Min6 cells were pre-incubated in serum-free oxygen-saturated Krebs-Ringer bicarbonate (KRB) buffer containing 3.3 mM glucose at 37° C. for 30 min. The cells ($7.5\times10^4$) were then incubated with KRB buffer containing high glucose (16.7 mM) or low glucose (3.3 mM) for an additional 30 min. The supernatants were collected for insulin ELISA assay.

Cell Viability Test

Min6 cells were cultured at 37° C. in complete medium. Cell cytotoxicity was determined using WST-1 (4-[3-(4-Iodophenyl)-2-(4-nitrophenyl)-2H-5-tetrazolio]-1,3-benzene Disulfonate) according to the manutkturet's guidelines. Briefly, the cells were grown in a 95-well plate containing complete medium in the presence of the indicated compounds for 24 h. Following PBS washing, WST-1 was added into each well for additional 20 min incubation. After removing the medium, the cells in the plate were measured with a SpectraMax i3x reader at 450 nm.

Statistics

Data from three or more independent experiments are presented as the mean±standard deviation (SD). Comparisons between multiple groups were performed using ANOVA unless indicated otherwise. $P<0.05$ (*), $<0.01$ () or $<0.001$() was considered to be statistically significant between control and treatment groups.

Tables 1-5 show $IC_{50}$ values of PDIA4 inhibitors.

| CPD | MW | Structure | IC50(μM) |
|---|---|---|---|
| P1 | 362.4 | 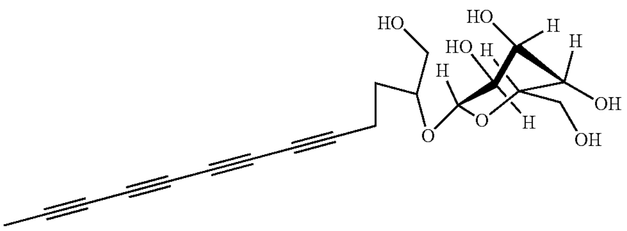 | 210.2 |
| P2 | 200.2 | 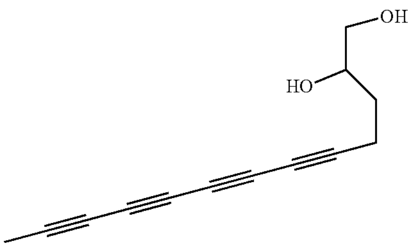 | 167.9 |
| C1 | 256.3 | 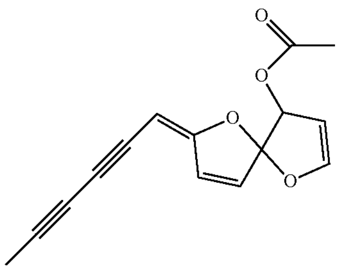 [SMILES: CC#CC#C/C=C1\C=CC2(OC=CC2OC(C)=O)O1] | 66.5 |
| C2 | 158.2 | 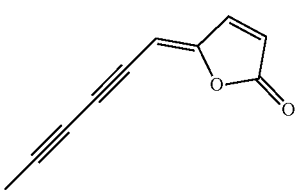 | 96.5 |

-continued
| CPD | MW | Structure | IC50(μM) |
|---|---|---|---|
| C3 | 186.2 | 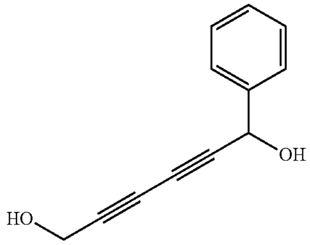 [SMILES: OCC#CC#CC(O)c1ccccc1] | 186.0 |
| C4 | 145.2 | 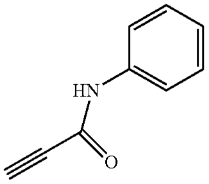 | 182.7 |
| C5 | 430.5 | 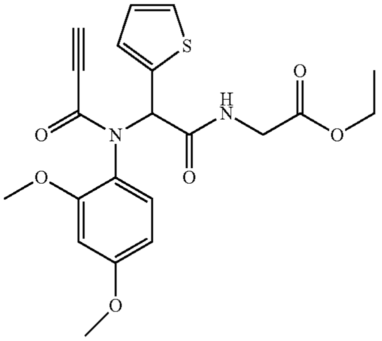 [SMILES: C#CC(=O)N(c1ccc(OC)cc1OC)C(C(=O)NCC(=O)OCC)c1cccs1] | 759.7 |
| C6 | 296.3 | 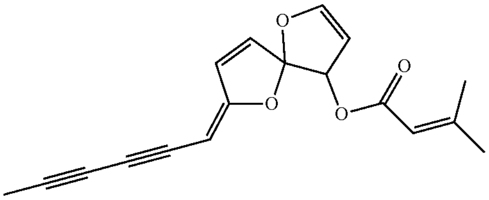 [SMILES: CC#CC#C/C=C1\C=CC2(OC=CC2OC(=O)C=C(C)C)O1] | 753.1 |
| C7 | 162.2 | 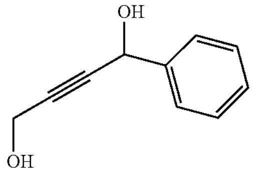 [SMILES: OCC#CC(O)c1ccccc1] | >1000 |
| C8 | 202.3 | 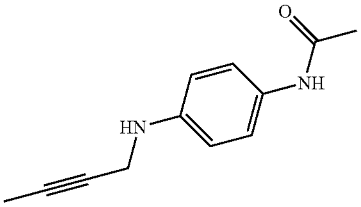 | >1000 |

-continued
| CPD | MW | Structure | IC50(μM) |
|---|---|---|---|
| C9 | 346.4 | 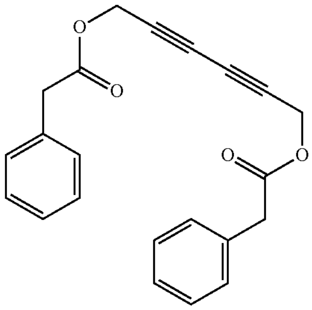 [SMILES: O=C(Cc1ccccc1)OCC#CC#CCOC(=O)Cc1ccccc1] | >1000 |
| C10 | 318.3 | 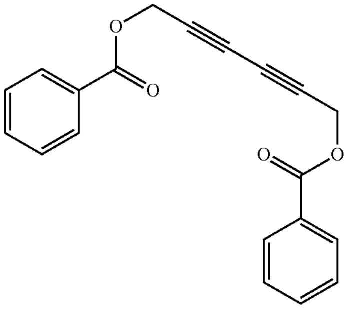 [SMILES: O=C(OCC#CC#CCOC(=O)c1ccccc1)c1ccccc1] | >1000 |
TABLE 2
| CPD | MW | Structure | IC50(μM) |
|---|---|---|---|
| C11 | 246.2 | 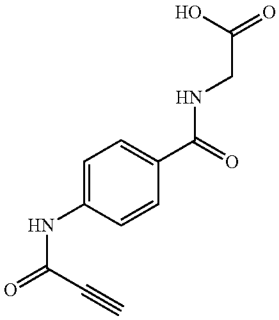 [SMILES: C#CC(=O)Nc1ccc(C(=O)NCC(=O)O)cc1] | 27.6 |
| C12 | 203.2 | 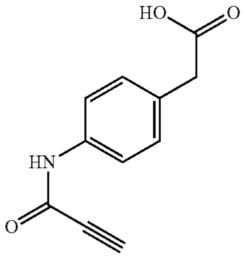 | 92.1 |
| 8 | 249.2 | 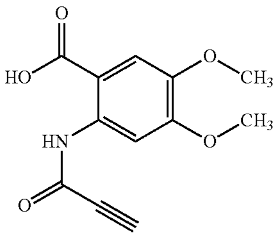 [SMILES: C#CC(=O)Nc1cc(OC)c(OC)cc1C(=O)O] | 4.0 |
TABLE 2-continued
| CPD | MW | Structure | IC50(μM) |
|---|---|---|---|
| C13 | 189.2 | 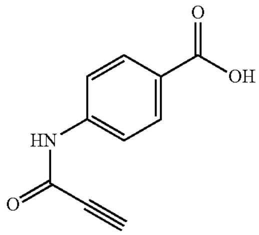 | 57.3 |
| C14 | 205.2 | 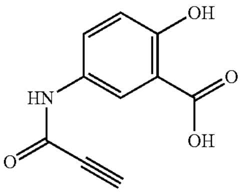 | 55.7 |
TABLE 3
| CFO | MW | IC50 (μM) |
|---|---|---|
| 16 | 325.32 | 13.3 |
| 22 | 279.25 | 4.3 |
| 45 | 277.28 | 1.0 |
| 14 | 415.44 | 84.9 |
| 20 | 293.27 | 42.5 |
| 4 | 263.25 | 11.7 |
| 43 | 319.36 | 430.6 |
| 30 | 347.41 | >300 |
| 29 | 305.3 | >300 |
| 10 | 249.22 | 1.6 |
| 21 | 277.21 | >1000 |
| 44 | 225.24 | >1000 |

TABLE 3-continued

| CFO | MW | IC50 (μM) |
|---|---|---|
| 19 | 241.24 | >1000 |
| 3 | 211.22 | >1000 |
| 9 | 197.19 | >1000 |
| 55 | 284.27 | >1000 |

TABLE 4

| CPD | MW | IC50 (μM) |
|---|---|---|
| 50a | 422.39 | 48.8 |
| 50b | 436.42 | 4.3 |
| 50c | 450.45 | 5.6 |
| 54 | 448.43 | 3.3 |
| 58a | 462.46 | 4.7 |
| 40 | 448.43 | 3.9 |
| 58d | 480.45 | 2.4 |
| 58c | 480.45 | 2.7 |
| 58b | 480.45 | 4.2 |
| 58e | 498.44 | 2.4 |
| 58h | 492.48 | 3.7 |
| 58g | 492.48 | 3.3 |
| 58f | 522.5 | 2.6 |
| 61 | 406.4 | 4.7 |
| 58i | 476.5 | 1.9 |
| 58j | 494.5 | 1.8 |
| 58r | 510.9 | 1.6 |
| 58m | 506.5 | 1.3 |
| 58o | 506.5 | 2.1 |
| 7 | 349.5 | 78.7 |
| 66 | 410.4 | 4.4 |
| 70 | 496.6 | 7.5 |
| 71 | 396.4 | 6.2 |
| 58p | 566.6 | 3.3 |
| 58l | 494.5 | 1.4 |
| 58t | 544.5 | 0.8 |
| 58s | 544.5 | 1.0 |
| 58k | 494.5 | 1.2 |
| 58u | 544.5 | 2.4 |
| 58n | 506.5 | 1.4 |
| 58q | 510.9 | 1.6 |
| 58v | 453.4 | 0.3 |

TABLE 5

| CPD | EC50(μM) | CC50(μM) | SI (CC50/EC50) |
|---|---|---|---|
| CCF642 | 0.25 | 23.9 | 95.6 |
| P1 | 1.55 | >100 | >64.5 |
| 8 | 0.06 | >100 | >1666.7 |
| 58v | 0.005 | >100 | >20000 |
| 58t | 0.03 | >100 | >3333 |
| 58s | 0.02 | 64.9 | 3245 |

RESULTS

Screening of PDIA4 Inhibitors from Hits to Lead Compounds.

Figure 2:
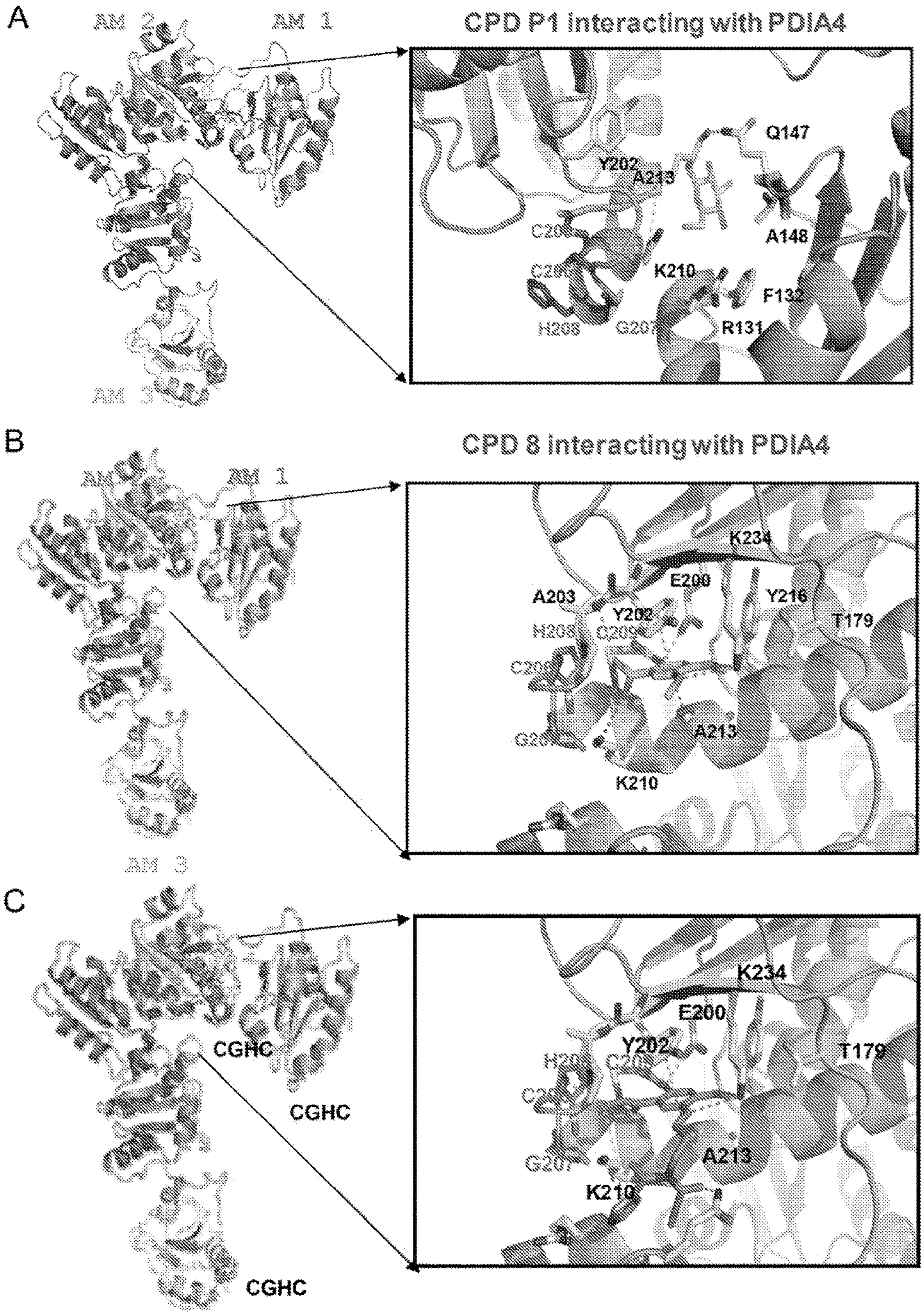
FIG. 2 shows molecular docking indicating the interaction between the selected PDIA4 inhibitors and active motifs (AMs) of PDIA4. (A) AM 1, 2 and 3 represent the first, second and third CGHC domains. The sulfur, nitrogen and oxygen atoms are shown in yellow, blue, and red, respectively. The hydrogen bond and hydrophobic interaction between CPD P1 and the amino acid residues of PDIA4 model are shown, respectively. (B) Similar to (A), molecular docking indicating the interaction between the selected CPD 8 and active motifs (AMs) of PDIA4.

Virtual screening and PDIA4 were applied to search hits, leads and/or drug candidates as described in FIG. 1. The details of virtual screening are delineated in the experimental procedures (FIG. 1). Out of 261 phytochemicals, cytopiloyne (CPD P1, Table 1) and cytopiloyne aglycone (CPD P2, Table 1) were identified as two best hits. The molecular docking of CPD P1 into PDIA4 with 3 active motifs is shown in FIG. 2. PDIA4 assay platform was established to measure the half maximal inhibitory concentration ($IC_{50}$) of CPD P2 (167.9 μM, Table 1).

Characterization of PDIA4-Based Drug Candidates.

Next, based on the pharmacophore features of CP/CPA and the binding pocket of PDIA4, ten compounds with 1 to 3 carbon/carbon triple bonds (CCTB), including (E)-7-(hexa-2,4-diyn-1-ylidene)-1,6-dioxaspiro[4,4]nona-2,8-dien-4-ylacetate (C1), (Z)-5-(hexa-2,4-diyn-1-ylidene) furan-2(5H)-one (C2), 1-phenylhexa-2,4-diyne-1,6-diol. (C3), N-phenylpropiolamide (C4), ethyl (2-(N-(2,4-dimethoxyphenyl)propiolamido)-2-(thiophen-2-yl)acetyl)glycinate (C5), (E)-7-(hexa-2,4-diyn-1-ylidene)-1,6-dioxaspiro [4,4]nona-2,8-dien-4-yl 3-methylbut-2-enoate (C6), 1-phenylbut-2-yne-1,4-diol (C7), N-(4-(but-2-yn-1-ylamino)phenyl)acetamide (C8), hexa-2,4-diyne-1,6-diyl bis(2-phenylacetate), and hexa-2,4-diyne-1 (C9) and 6-diyl dibenzoate (C10), were selected from the ZINC database using the virtual screening and measured for the $IC_{50}$ values in an attempt to determine the core structure of leads (Table 1). N-phenylpropiolamide (C4) ($IC_{50}$=182.7 μM, Table 1) was selected as the active core structure to do substructure search for leads. Consequently, (4-propiolamidobenzoyl) glycine (C11), 2-(4-propiolamidophenyl)acetic acid (C12), 4,5-dimethoxy-2-propiolamidobenzoic acid (8), 4-propiolamidobenzoic acid (C13), and 2-hydroxy-5-propiolamidobenzoic acid (C14), containing the core structure of N-phenylpropiolamide (C4), were selected and tested for the $IC_{50}$ values (Table 2). As a result, 4,5-dimethoxy-2-propiolamidobenzoic acid (8) stood out as a potential lead with the $IC_{50}$ value of 4 μM, which is 53 times higher than the hit, CPU P1 (Table 2). 4,5-dimethoxy-2-propiolamidobenzoic acid (8) was synthesized from 4,5-dimethoxy-2-nitrobenzoic acid (1) was based on Scheme 2.

For optimization of 4,5-dimethoxy-2-propiolamidobenzoic acid (8), 4,5-dimethoxy-2-nitrobenzoic acid (1) was chemically modified into compounds 2-8 based on Schemes 1 and 2. As a consequence, 4,5-dimethoxy-2-propiolamidobenzoic acid (8) stood out as a potential lead with the $IC_{50}$ value of 4 μM, which is 40 times higher than the hit, CPA (Tables 1 and 2). Furthermore, chemical modification of 4,5-dimethoxy-2-propiolainidobenzoic acid (8) was conducted based on Schemes 3-20. Compounds 9-58v were synthesized and tested for PDIA4 inhibition (Table 1). Their $IC_{50}$ values are shown in Tables 3 and 4. The details about the synthesis and structural elucidation of CPDs 1-58v were described in the Chemistry section of Material and methods. Therefore, several compounds, 8, 58v, 58s, and 58t, had low IC50 values and can be used as drug candidates.

Pharmacological Effect of the Selected PDIA4 Inhibitors on Insulin Secretion and Cell Viability in β-Cells.

Figure 3:
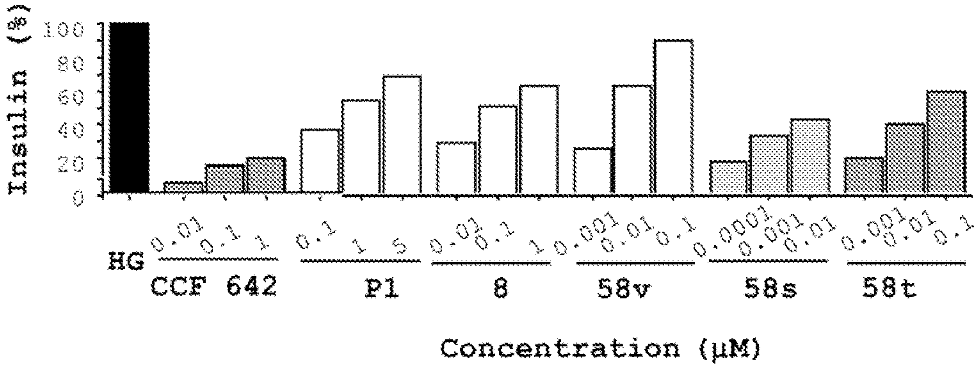
FIG. 3 shows insulin-releasing effect and cytotoxicity of drug candidates. (A) Effect of drug candidates on insulin secretion in β-cells. Min6 cells were incubated in serum-free oxygen-saturated Krebs-Ringer bicarbonate (KRB) buffer containing high glucose (16.7 mM), CCF642 and drug candidates for 30 min. The supernatants were collected for insulin ELISA assay. (B) Min6 cells were incubated with PBS, CCF642 and drug candidates, respectively, for 24 h. Following PBS washing, WST-1 was added into each well for additional 20 min incubation.
Figure 3:
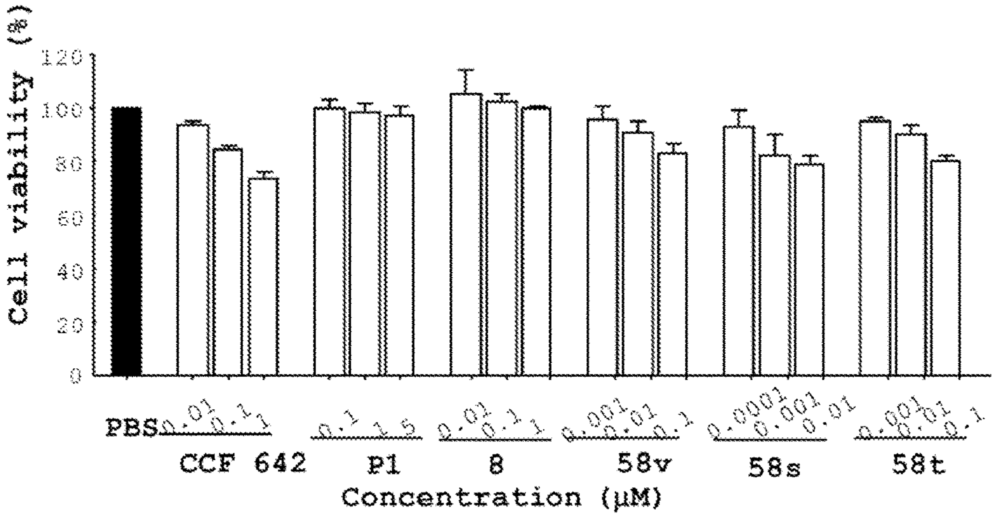

Next, we examined the effect of the selected PDIA4 inhibitors, CCF642, a commercial PDIA4 inhibitor, and CPDs P1, 8, 58v, 58s, and 58t on insulin-releasing action in Min6, a mouse β-cells. We found that CCF642 and CPDs P1, 8, 58v, 58s, and 58t had EC50 values of 0.25, 1.55, 0.06, 0.005, 0.03 and 0.02 μM, respectively (FIG. 3 and Table 2). In contrast, slight effect of insulin release in Min6 cells. Accordingly, CCF642 and CPDs P1, 8, 58v, 58s, and 58t had CC50 values of 23.9, >100, >100, >100, >100, and 64.9, respectively (FIG. 3 and Tables 1-4). The data suggest that like CCF642, CPDs P1, 8, 58v, 58s, and 58t could augment insulin secretion in β-cells. The molecular docking of CPD 8 into PDIA4 with 3 active motifs is shown in FIG. 2. The data showed that CPD 8 fit better to PDIA4 than CPD P1 (FIG. 2).

Pharmacological Effect of the Selected PDIA4 Inhibitors on Diabetes in db/db Mice.

Figure 4:
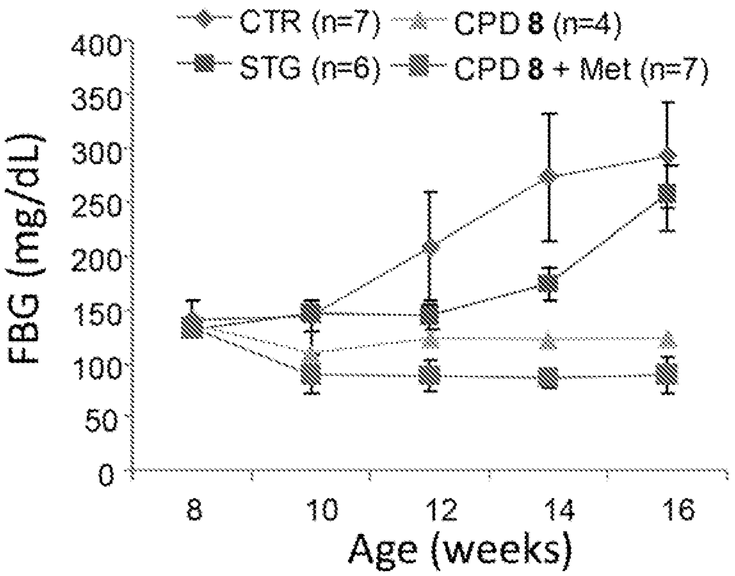
FIG. 4 shows CPD8 per se and in combination with metformin can treat and reverse diabetes in $Lepr^{db/db}$ mice. (A-B) New-onset diabetes, $Lepr^{db/db}$ mice, are grouped and treated with PBS vehicle (CTR), sitagliptin (STG, 30 Mg/kg), CPD8 (2.5 mg/kg), and a combination of CPD8 (2.5 mg/kg) and metformin 960 mg/kg) (CPD8+Met) for the indicated time. Fasting blood glucose (FBG (A)) and postprandial blood glucose (PBG (B)) of the mice were monitored. The value (n) is number of mice indicated in parentheses.
Figure 4:
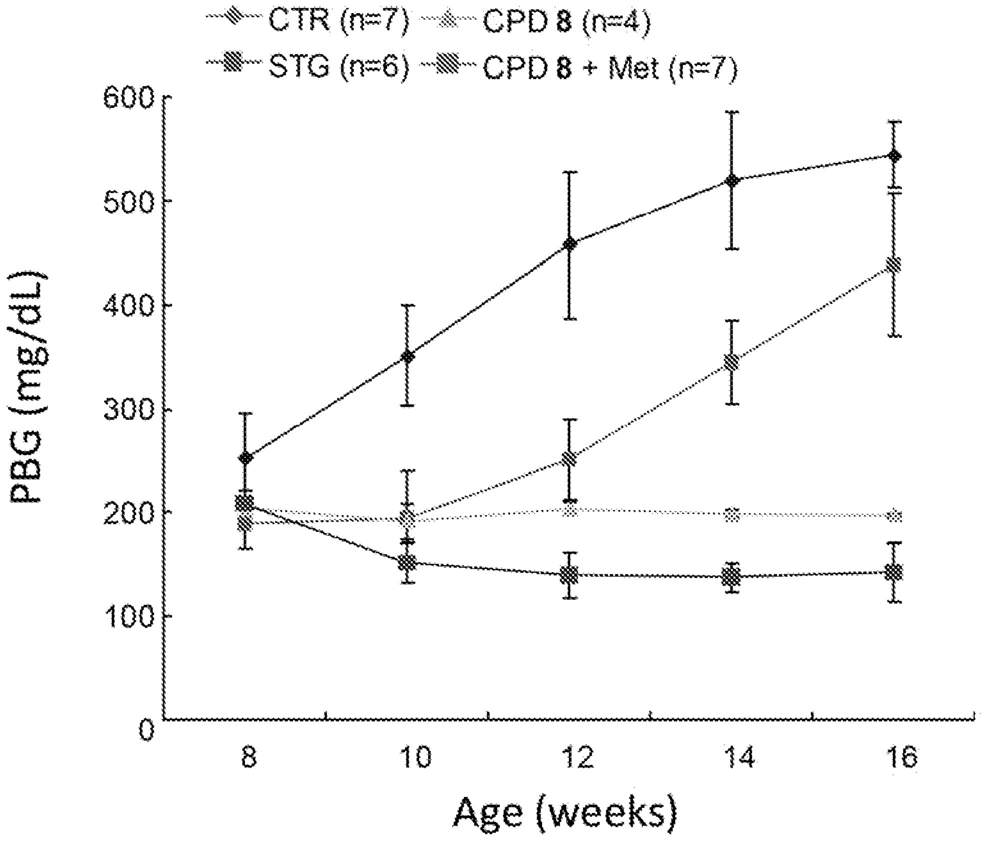

Moreover, we examined the in vivo anti-diabetes effect of CPD 8, one of drug candidates for Pdia4 inhibition, in db/db mice, a mouse model of type 2 diabetes. As anticipated, 30 mg/kg of sitagliptin (STG), which was used as a positive control, significantly reduced fasting blood glucose (FBG) in db/db mice (FIG. 4A). CPD 8, at the close of 2.5 mg/kg, significantly decreased FBG in db/db mice (FIG. 3A). Further, a combination of CPD 8 (2.5 mg/kg) and metformin (60 mg/kg) decreased FBG more than CPD 8 alone in db/db mice (FIG. 4A). Accordingly, 30 mg/kg of sitagliptin, which was used as a positive control, significantly reduced post-prandial blood glucose (PBG) in db/db mice (FIG. 4B). CPD 8, at the dose of 2.5 mg/kg, significantly decreased. PBG in db/db mice (FIG. 4B). Further, a combination of CPD 8 (2.5 mg/kg) and metformin (60 mg/kg) decreased PBG more than CPD8 alone in db/db mice (FIG. 4B). The overall data demonstrate that CPD 8, one of the PDIA4-based drug candidates, per se and in combination can reverse type 2 diabetes in db/db mice.

In summary, pancreatic β-cell failure is a hallmark of type 2 diabetes (T2D). Strategies to preserve β-cell function/mass at the early diabetic stage, which can reverse T2D, are highly demanded. The invention relates to screening PDIA4-based inhibitors from hits to leads using a combination of molecular docking and PDIA4 bioassays. N-phenylpropiolamide (C4) was identified as active core structure of PDIA4 inhibitors. 4,5-dimethoxy-2-propiolamidobenzoic acid (8) was identified as a lead using a combination of chemical synthesis, molecular docking and PDIA4 bioassays. Based on the structure and activity relationship between compounds and PDIA4, 48 compounds (Table 6) were synthesized and characterized. As a result, several drug candidates with the $IC_{50}$ values from 4 μM to 300 nM, including CPDs P1, 8, 58v, 58s, and 58t, were identified. Those compounds were tested for β-cell function and diabetes treatment. Like CCF642, a commercial PDIA4 inhibitor, CPDs P1, 8, 58v, 58s, and 58t, had a higher activity for insulin secretion in β-cells. Accordingly, CPD 8, alone and in combination could treat and reverse T2D in db/db mice, a diabetic mouse model. The overall data suggest PDIA4 as a novel therapeutic target of type 2 diabetes (T2D). Table 6 illustrates compounds of the invention.

TABLE 6

(I)

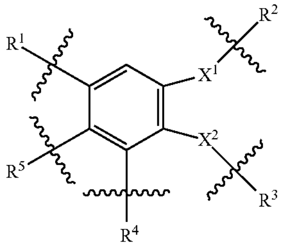

| | | |
|---|---|---|
| 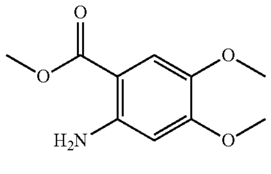 3 | 3: methyl 2-amino-4,5-dimethoxybenzoate; | R1 = CH3O—CO—<br>R2 = CH3<br>R3 = CH3; R4 = H<br>R5 = amino (—NH2)<br>X1 = O; X2 = O |
| 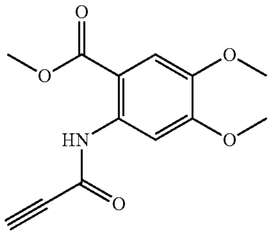 4 | 4: methyl 4,5-dimethoxy-2-propiolamidobenzoate; | R1 = CH3O—CO—<br>R2 = CH3<br>R3 = CH3; R4 = H<br>R5 = —NH—CO—CCH<br>X1 = O; X2 = O |
| 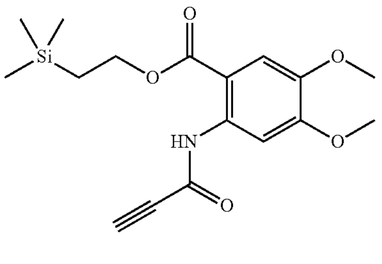 7 | 7: 2-(trimethylsily Dethyl 4,5-dimethoxy-2-propiolamidobenzoate; | R1 = $(CH3)_3$—Si—CH2—CH2—O—CO—<br>R2 = CH3<br>R3 = CH3; R4 = H<br>R5 = —NH—CO—CCH<br>X1 = O; X2 = O |

TABLE 6-continued

| (I) | | |
|---|---|---|
| 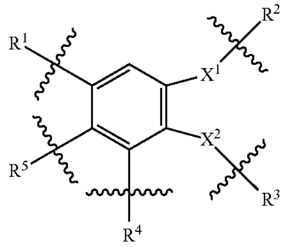 | | |
| 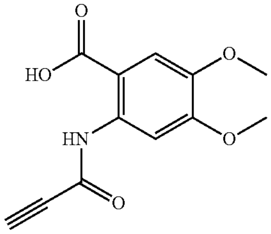<br>8 | 8: 4,5-dimethoxy-2-propiolamidobenzoic acid; | R1 = HO—CO—<br>R2 = CH3<br>R3 = CH3<br>R4 = H<br>R5 = —NH—CO—CCH<br>X1 = O; X2 = O |
| 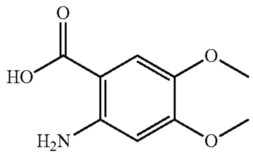<br>9 | 9: 2-amino-4,5-dimethoxybenzoic acid; | R1 = HO—CO—<br>R2 = CH3<br>R3 = CH3; R4 = H<br>R5 = amino (—NH2)<br>X1 = O; X2 = O |
| 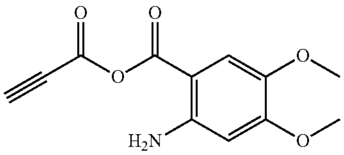<br>10 | 10: 2-amino-4,5-dimethoxybenzoic propiolic anhydride; | R1 = HCC—CO—O—CO—<br>R2 = CH3<br>R3 = CH3; R4 = H<br>R5 = amino (—NH2)<br>X1 = O; X2 = O |
| 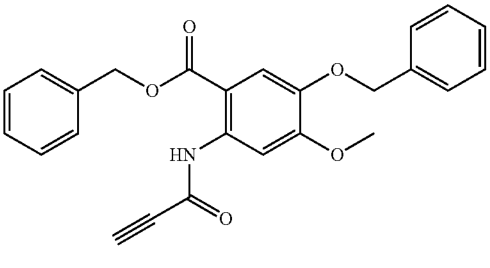<br>14 | 14: benzyl 5-(benzyloxy)-4-methoxy-2-propiolamidobenzoate;<br>Benzyl = $C_6H_5$—$CH_2$—<br>Phenyl = $C_6H_5$ | R1 = benzyl-O—CO—<br>R2 = benzyl (—$CH_2$—$C_6H_5$<br>R3 = CH3;<br>R4 = H<br>R5 = —NH—CO—CCH<br>X1 = O; X2 = O |
| 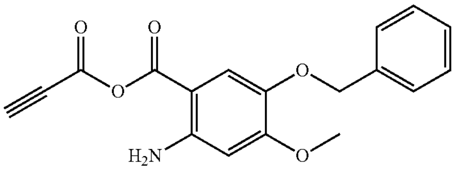<br>16 | 16: 2-amino-5-(benzyloxy)-4-methoxybenzoic propiolic anhydride | R1 = HCC—CO—O—CO—<br>R2 = benzyl<br>R3 = CH3;<br>R4 = H<br>R5 = amino (—NH2)<br>X1 = O; X2 = O |

TABLE 6-continued

| | | |
|---|---|---|
| 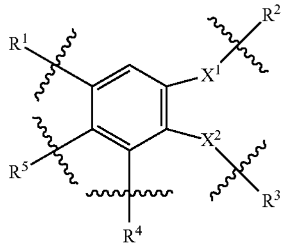 (I) | | |
| 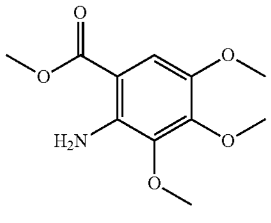 19 | 19: methyl 2-amino-3,4,5-trimethoxybenzoate; | R1 = CH3O—CO—<br>R2 = —CH3<br>R3 = —CH3<br>R4 = CH3—O—<br>R5 = amino (—NH2)<br>X1 = O; X2 = O |
| 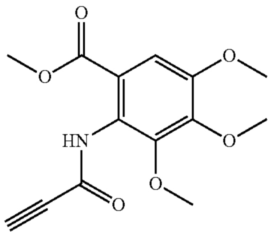 20 | 20: methyl 3,4,5-trimethoxy-2-propiolamidobenzoate; | R1 = CH3—O—CO—<br>R2 = CH3<br>R3 = CH3<br>R4 = —O—CH3<br>R5 = HCC—CO—NH—<br>X1 = O; X2 = O |
| 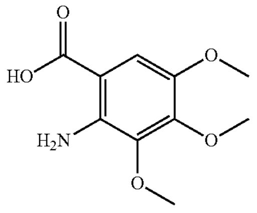 21 | 21: methyl 2-amino-3,4,5-trimethoxybenzoate; | R1 = HO—CO—<br>R2 = CH3<br>R3 = CH3<br>R4 = CH3—O—<br>R5 = amino (—NH2)<br>X1 = O; X2 = O |
| 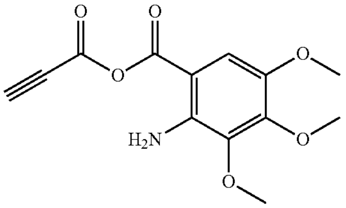 22 | 22: 2-amino-3,4,5-trimethoxybenzoic propiolic anhydride; | R1 = HCC—CO—O—CO—<br>R2 = CH3<br>R3 = CH3<br>R4 = CH3—O—<br>R5 = amino (—NH2)<br>X1 = O; X2 = O |
| 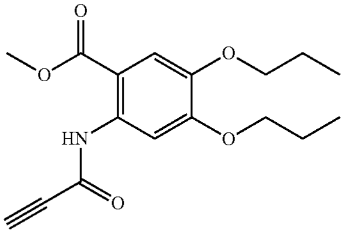 29 | 29: methyl 2-propiolamido-4,5-dipropoxybenzoate; | R1 = CH3—O—CO—<br>R2 = CH3—(CH2)2—<br>R3 = CH3—(CH2)2—<br>R4 = —H<br>R5 = HCC—CO—NH—<br>X1 = O; X2 = O |

TABLE 6-continued (I)

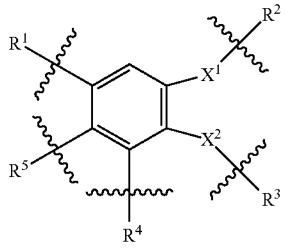

| | | |
|---|---|---|
| 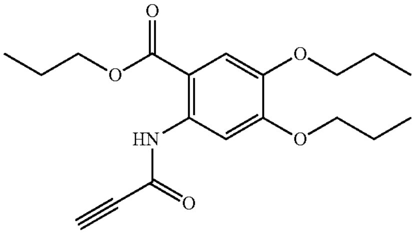<br>30 | 30: propyl 2-propiolamido-4,5-dipropoxybenzoate; | R1 = CH3—(CH2)$_2$—O—CO—<br>R2 = CH3—(CH2)2—<br>R3 = CH3—(CH2)2—<br>R4 = H<br>R5 = HCC—CO—NH—<br>X1 = O; X2 = O |
| 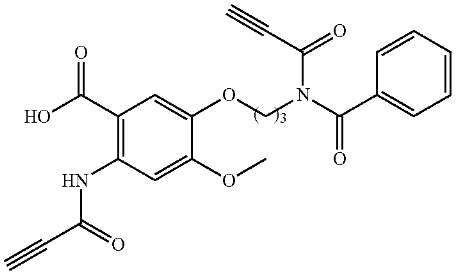<br>40 | 40: 4-methoxy-2-propiolamido-5-(3-(N-propioloylbenzamido)propoxy) benzoic acid; | R1 = HO—CO—<br>R2 = CH2)3—N—(CO—CCH)-benzoyl<br>R3 = —CH3;<br>R4 = H<br>R5 = —NH—CO—CCH<br>X1 = O; X2 = O |
| 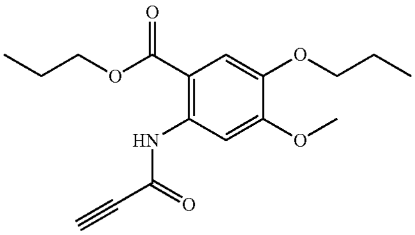<br>43 | 43: propyl 4-methoxy-2-propiolamido-5-propoxybenzoate; | R1 = CH3—(CH2)$_2$—O—CO—<br>R2 = CH3—(CH2)2—<br>R3 = —CH3;<br>R4 = H<br>R5 = —NH—CO—CCH<br>X1 = O; X2 = O |
| 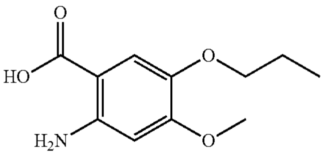<br>44 | 44: 2-amino-4-methoxy-5-propoxybenzoic acid; | R1 = HO—CO—<br>R2 = —(CH$_2$)$_2$—CH3<br>R3 = CH3<br>R4 = CH3—O—<br>R5 = amino (—NH2)<br>X1 = O; X2 = O |
| 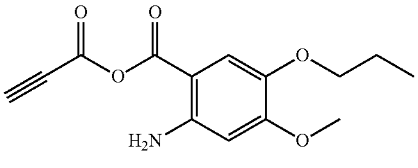<br>45 | 45: 2-amino-4-methoxy-5-propoxybenzoic propiolic anhydride; | R1 = HCC—CO—O—CO—<br>R2 = —(CH$_2$)$_2$—CH3<br>R3 = CH3;<br>R4 = H<br>R5 = amino (—NH2)<br>X1 = O; X2 = O |

TABLE 6-continued

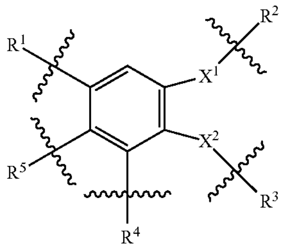

(I)

| | | |
|---|---|---|
| 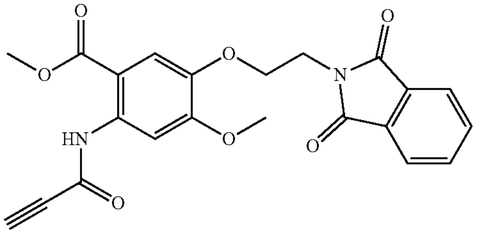<br>50a | 50a: methyl 5-(2-(1,3-dioxoisoindolin-2-yl)ethoxy)-4-methoxy-2-propiolamidobenzoate; | R1 = CH3—O—CO—<br>R2 = —(CH2)2-(1,3-dioxoisoindolin-2-yl)<br>R3 = —CH3;<br>R4 = H<br>R5 = —NH—CO—CCH<br>X1 = O; X2 = O |
| 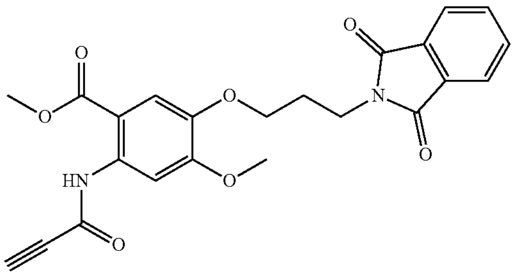<br>50b | 50b: methyl 5-(3-(1,3-dioxoisoindolin-2-yl)propoxy)-4-methoxy-2-propiolamidobenzoate; | R1 = CH3—O—CO—<br>R2 = —$(CH_2)_3$-(1,3-dioxoisoindolin-2-yl)<br>R3 = —CH3;<br>R4 = H<br>R5 = —NH—CO—CCH<br>X1 = O; X2 = O |
| 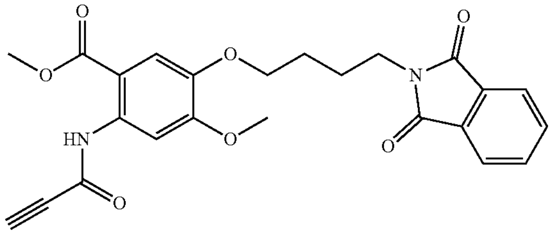<br>50c | 50c: methyl 5-(4-(1,3-dioxoisoindolin-2-yl)butoxy)-4-methoxy-2-propiolamidobenzoate; | R1 = CH3—O—CO—<br>R2 = —$(CH_2)_4$-(1,3-dioxoisoindolin-2-yl)<br>R3 = —CH3;<br>R4 = H<br>R5 = —NH—CO—CCH<br>X1 = O; X2 = O |
| 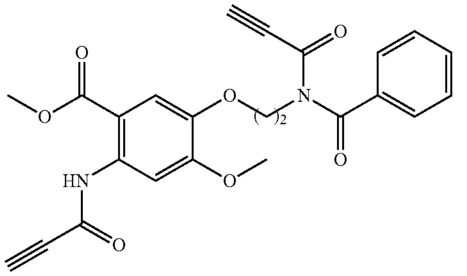<br>54 | 54: methyl 4-methoxy-2-propiolamido-5-(2-(N-propioloylbenzamido)ethoxy) benzoate; | R1 = CH3—O—CO—<br>R2 = —$(CH_2)_2$—N—(CO—CCH)-benzoyl<br>R3 = —CH3;<br>R4 = H<br>R5 = —NH—CO—CCH |

TABLE 6-continued

| | | |
|---|---|---|
| 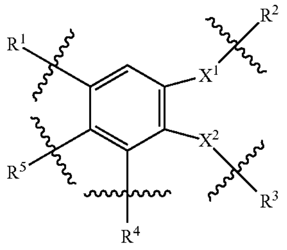 | | (I) |
| 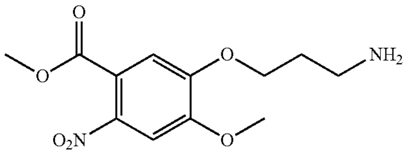<br>55 | 55: methyl 5-(3-aminopropoxy)-4-methoxy-2-nitrobenzoate; | R1 = CH3—O—CO—<br>R2 = NH2—(CH2)3—<br>R3 = CH3—; R4 = —H<br>R5 = —NO2<br>X1 = O; X2 = O |
| 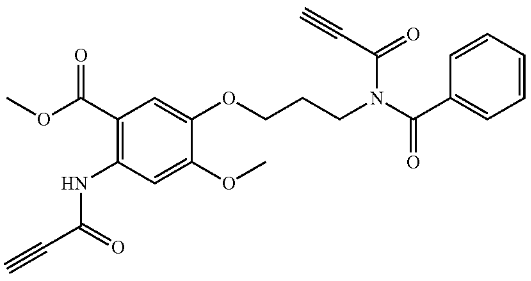<br>58a | 58a: methyl 4-methoxy-2-propiolamido-5-(3-(N-propioloylbenzamido)propoxy) benzoate; | R1 = CH3—O—CO—<br>R2 = —$(CH_2)_3$—N—(CO—CCH)-benzoyl<br>R3 = —CH3; R4 = H<br>R5 = —NH—CO—CCH<br>X1 = O; X2 = O |
| 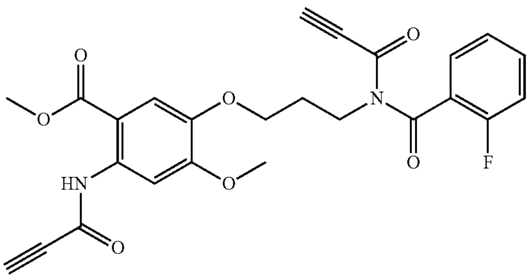<br>58b | 58b: methyl 5-(3-(2-fluoro-N-propioloylbenzamido)propoxy)-4-methoxy-2-propiolamidobenzoate; | R1 = CH3—O—CO—<br>R2 = —$(CH_2)_3$—N—(CO—CCH)-benzoyl-(2-fluoro)<br>R3 = —CH3; R4 = H<br>R5 = —NH—CO—CCH<br>X1 = O; X2 = O |
| 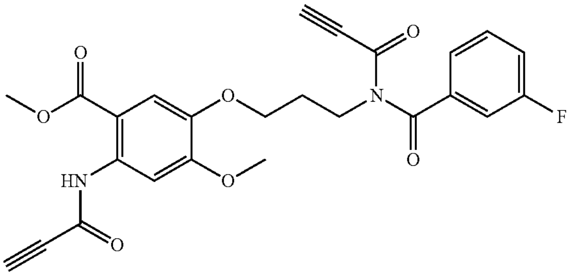<br>58c | 58e: methyl 5-(3-(3-fluoro-N-propioloylbenzamido)propoxy)-4-methoxy-2-propiolamidobenzoate; | R1 = CH3—O—CO—<br>R2 = —$(CH_2)_3$—N—(CO—CCH)-benzoyl-3-fluoro<br>R3 = —CH3;<br>R4 = H<br>R5 = —NH—CO—CCH<br>X1 = O; X2 = O |

TABLE 6-continued (I)

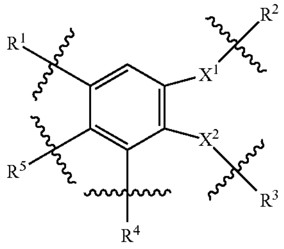

| | | |
|---|---|---|
| 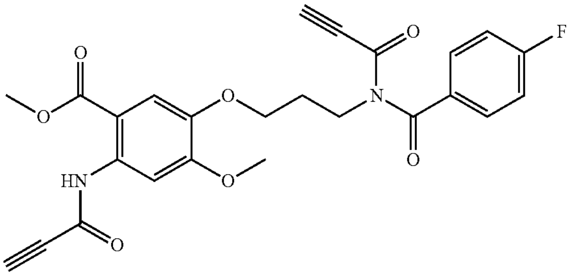<br>58d | 58d: methyl 5-(3-(4-fluoro-N-propioloylbenzamido)propoxy)-4-methoxy-2-propiolamidobenzoate; | R1 = CH3—O—CO—<br>R2 = —$(CH_2)_3$—N—(CO—CCH)-benzoyl-(4-fluoro)<br>R3 = —CH3;<br>R4 = H<br>R5 = —NH—CO—CCH<br>X1 = O; X2 = O |
| 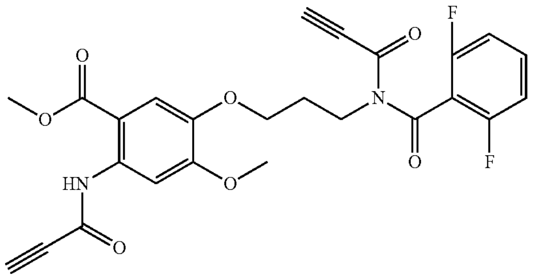<br>58e | 58e: methyl 5-(3-(2,6-difluoro-N-propioloylbenzamido)propoxy)-4-methoxy-2-propiolamidobenzoate; | R1 = CH3—O—CO—<br>R2 = —$(CH_2)_3$—N—(CO—CCH)-benzoyl-(2,6-difluoro)<br>R3 = —CH3;<br>R4 = H<br>R5 = —NH—CO—CCH<br>X1 = O; X2 = O |
| 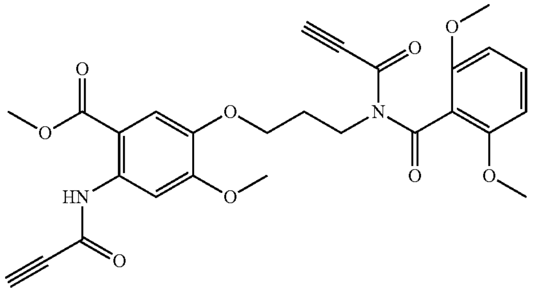<br>58f | 58f: methyl 5-(3-(2,6-dimethoxy-N-propioloylbenzamido)propoxy)-4-methoxy-2-propiolamidobenzoate; | R1 = CH3—O—CO—<br>R2 = —$(CH_2)_3$—N—(CO—CCH)-benzoyl-(2,6-dimethoxy)<br>R3 = —CH3;<br>R4 = H<br>R5 = —NH—CO—CCH<br>X1 = O; X2 = O |
| 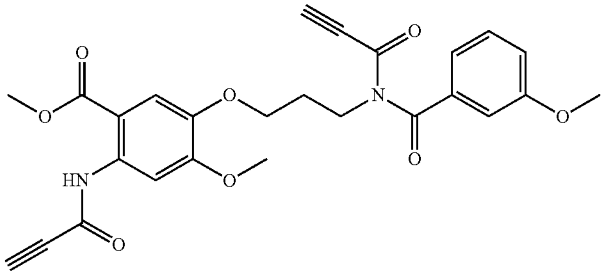<br>58g | 58g: methyl 4-methoxy-5-(3-(3-methoxy-N-propioloylbenzamido)propoxy)-2-propiolamidobenzoate; | R1 = CH3—O—CO—<br>R2 = —$(CH_2)_3$—N—(CO—CCH)-benzoyl-(3-methoxy)<br>R3 = —CH3;<br>R4 = H<br>R5 = —NH—CO—CCH<br>X1 = O; X2 = O |

TABLE 6-continued (I)

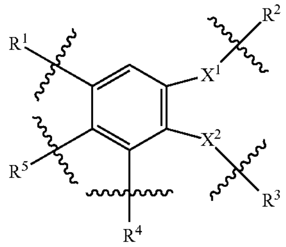

| | | |
|---|---|---|
| 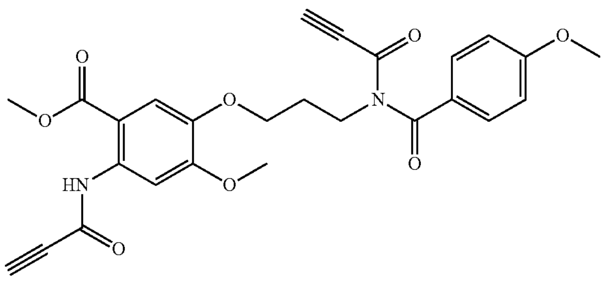 [SMILES: C#CC(=O)Nc1cc(OC)c(OCCCN(C(=O)C#C)C(=O)c2ccc(OC)cc2)cc1C(=O)OC]<br>58h | 58h: methyl 4-methoxy-5-(3-(4-methoxy-N-propioloylbenzamido)propoxy)-2-propiolamidobenzoate; | R1 = CH3—O—CO—<br>R2 = —$(CH_2)_3$—N—(CO—CCH)-benzoyl-(4-methoxy)<br>R3 = —CH3;<br>R4 = H<br>R5 = —NH—CO—CCH<br>X1 = O; X2 = O |
| 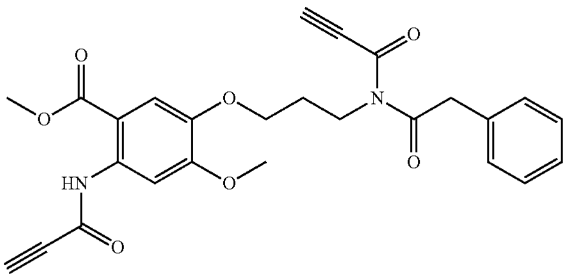 [SMILES: C#CC(=O)Nc1cc(OC)c(OCCCN(C(=O)C#C)C(=O)Cc2ccccc2)cc1C(=O)OC]<br>58i | 58i: methyl 4-methoxy-5-(3-(N-(2-phenylacetyl)propiolamido) propoxy)-2-propiolamidobenzoate; | R1 = CH3—O—CO—<br>R2 = —$(CH_2)_3$—N—(CO—CCH)—CO—CH2-phenyl<br>R3 = —CH3;<br>R4 = H<br>R5 = —NH—CO—CCH<br>X1 = O; X2 = O |
| 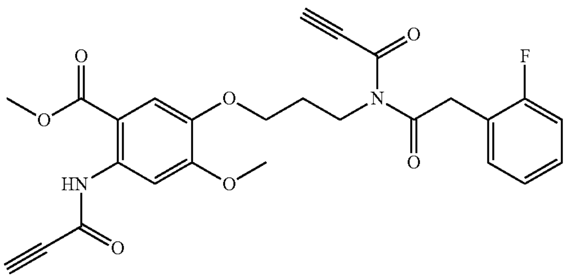 [SMILES: C#CC(=O)Nc1cc(OC)c(OCCCN(C(=O)C#C)C(=O)Cc2ccccc2F)cc1C(=O)OC]<br>58j | 58j: methyl 5-(3-(N-(2-(2-fluorophenyl)acetyl)propiolamido) propoxy)-4-methoxy-2-propiolamidobenzoate; | R1 = CH3—O—CO—<br>R2 = —$(CH_2)_3$—N—(CO—CCH)—CO—CH2-phenyl-(2-fluoro)<br>R3 = —CH3;<br>R4 = H<br>R5 = —NH—CO—CCH<br>X1 = O; X2 = O |
| 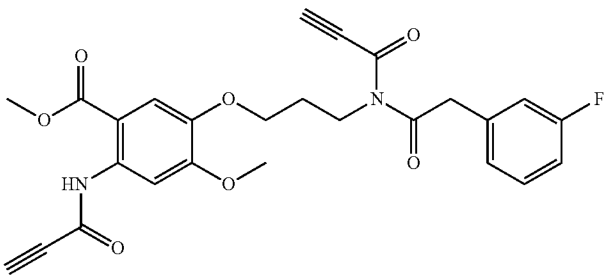 [SMILES: C#CC(=O)Nc1cc(OC)c(OCCCN(C(=O)C#C)C(=O)Cc2cccc(F)c2)cc1C(=O)OC]<br>58k | 58k: methyl 5-(3-(N-(2-(3-fluorophenyl)acetyl)propiolamido) propoxy)-4-methoxy-2-propiolamidobenzoate; | R1 = CH3—O—CO—<br>R2 = —$(CH_2)_3$—N—(CO—CCH)—CO—CH2-phenyl-(3-fluoro)<br>R3 = —CH3;<br>R4 = H<br>R5 = —NH—CO—CCH<br>X1 = O; X2 = O |

TABLE 6-continued (I)

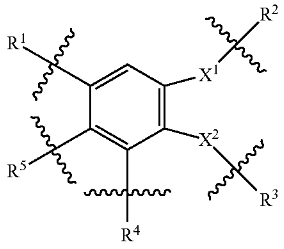

| | | |
|---|---|---|
| 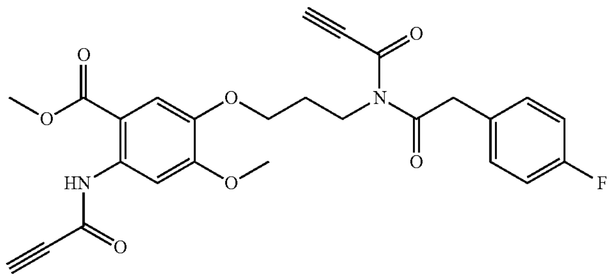 [SMILES: C#CC(=O)Nc1cc(OC)c(OCCCN(C(=O)C#C)C(=O)Cc2ccc(F)cc2)cc1C(=O)OC]<br>58l | 58l: methyl 5-(3-(N-(2-(4-fluorophenyl)acetyl)propiolamido)propoxy)-4-methoxy-2-propiolamidobenzoate; | R1 = CH3—O—CO—<br>R2 = —$(CH_2)_3$—N—(CO—CCH)—CO—CH2-phenyl-(4-fluoro)<br>R3 = —CH3;<br>R4 = H<br>R5 = —NH—CO—CCH<br>X1 = O; X2 = O |
| 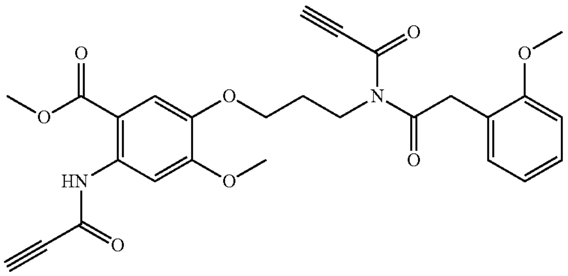 [SMILES: C#CC(=O)Nc1cc(OC)c(OCCCN(C(=O)C#C)C(=O)Cc2ccccc2OC)cc1C(=O)OC]<br>58m | 58m: methyl 4-methoxy-5-(3-(N-(2-(2-methoxyphenyl)acetyl)propiolamido)propoxy)-2-propiolamidobenzoate; | R1 = CH3—O—CO—<br>R2 = —$(CH_2)_3$—N—(CO—CCH)—CO—CH2-phenyl-(2-methoxy)<br>R3 = —CH3;<br>R4 = H<br>R5 = —NH—CO—CCH<br>X1 = O; X2 = O |
| 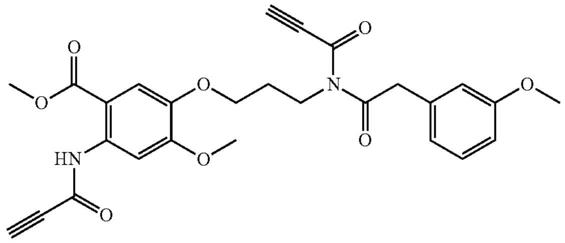 [SMILES: C#CC(=O)Nc1cc(OC)c(OCCCN(C(=O)C#C)C(=O)Cc2cccc(OC)c2)cc1C(=O)OC]<br>58n | 58n: methyl 4-methoxy-5-(3-(N-(2-(3-methoxyphenyl)acetyl)propiolamido)propoxy)-2-propiolamidobenzoate; | R1 = CH3—O—CO—<br>R2 = —$(CH_2)_3$—N—(CO—CCH)—CO—CH2-phenyl-(3-methoxy)<br>R3 = —CH3;<br>R4 = H<br>R5 = —NH—CO—CCH<br>X1 = O; X2 = O |
| 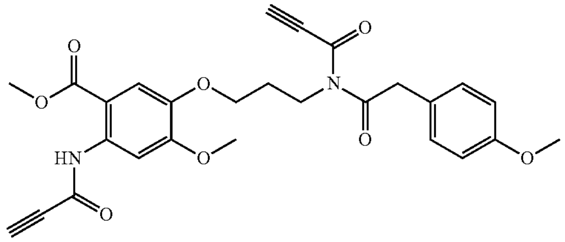<br>58o | 58o: methyl 4-methoxy-5-(3-(N-(2-(4-methoxyphenyl)acetyl)propiolamido)propoxy)-2-propiolamidobenzoate; | R1 = CH3—O—CO—<br>R2 = —$(CH_2)_3$—N—(CO—CCH)—CO—CH2-phenyl-(4-methoxy)<br>R3 = —CH3;<br>R4 = H<br>R5 = —NH—CO—CCH<br>X1 = O; X2 = O |

TABLE 6-continued

| | | |
|---|---|---|
| 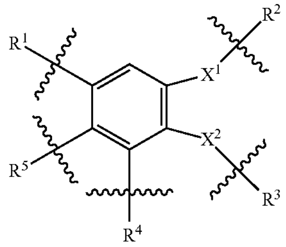 | | (I) |
| 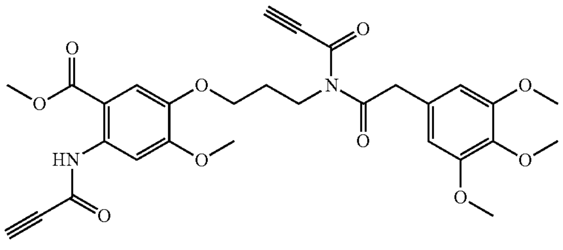 [SMILES: C#CC(=O)Nc1cc(OC)c(OCCCN(C(=O)C#C)C(=O)Cc2cc(OC)c(OC)c(OC)c2)cc1C(=O)OC]<br>58p | 58p: methyl 4-methoxy-2-propiolamido-5-(3-(N-(2-(3,4,5-trimethoxyphenyl)acetyl) propiolamido)propoxy)benzoate; | R1 = CH3—O—CO—<br>R2 = —$(CH_2)_3$—N—(CO—CCH)—CO—CH2-phenyl-3,4,5-trimethoxy)<br>R3 = —CH3;<br>R4 = H<br>R5 = —NH—CO—CCH<br>X1 = O; X2 = O |
| 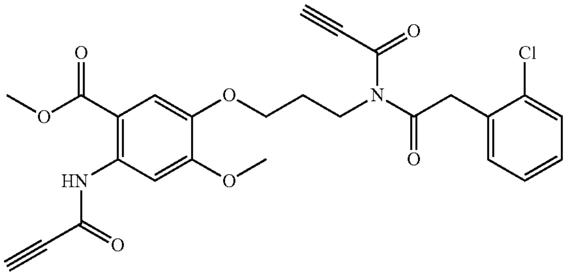 [SMILES: C#CC(=O)Nc1cc(OC)c(OCCCN(C(=O)C#C)C(=O)Cc2ccccc2Cl)cc1C(=O)OC]<br>58q | 58q: methyl 5-(3-(N-(2-(2-chlorophenyl)acetyl)propiolamido) propoxy)-4-methoxy-2-propiolamidobenzoate; and | R1 = CH3—O—CO—<br>R2 = —$(CH_2)_3$—N—(CO—CCH)—CO—CH2-phenyl-(2-chloro)<br>R3 = —CH3; R4 = H<br>R5 = —NH—CO—CCH<br>X1 = O; X2 = O |
| 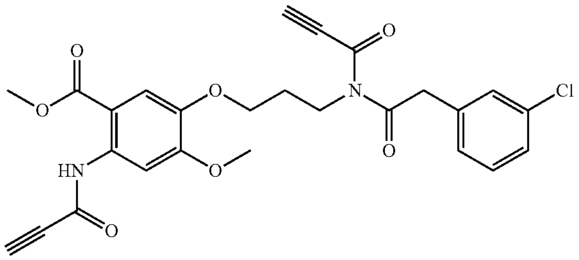 [SMILES: C#CC(=O)Nc1cc(OC)c(OCCCN(C(=O)C#C)C(=O)Cc2cccc(Cl)c2)cc1C(=O)OC]<br>58r | 58r: methyl 5-(3-(N-(2-(3-chlorophenyl)acetyl)propiolamido) propoxy)-4-methoxy-2-propiolamidobenzoate; | R1 = CH3—O—CO—<br>R2 = —$(CH_2)_3$—N—(CO—CCH)—CO—CH2-phenyl-(3-chloro)<br>R3 = —CH3;<br>R4 = H<br>R5 = —NH—CO—CCH<br>X1 = O; X2 = O |
| 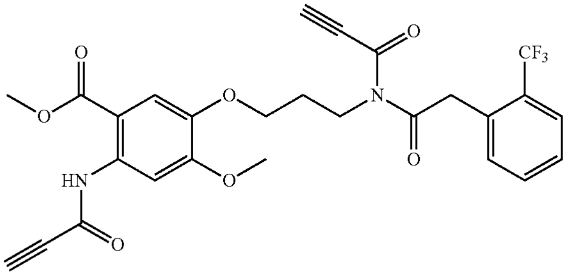 [SMILES: C#CC(=O)Nc1cc(OC)c(OCCCN(C(=O)C#C)C(=O)Cc2ccccc2C(F)(F)F)cc1C(=O)OC]<br>58s | 58s: methyl 4-methoxy-2-propiolamido-5-(3-(N-(2-(2-(trifluoromethyl)phenyl)acetyl) propiolamido)propoxy)benzoate; | R1 = CH3—O—CO—<br>R2 = —$(CH_2)_3$—N—(CO—CCH)—CO—CH2-phenyl-(2-trifluoromethyl)<br>R3 = —CH3;<br>R4 = H<br>R5 = —NH—CO—CCH<br>X1 = O; X2 = O |

TABLE 6-continued

| | | |
|---|---|---|
| 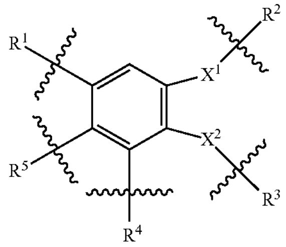 | | (I) |
| 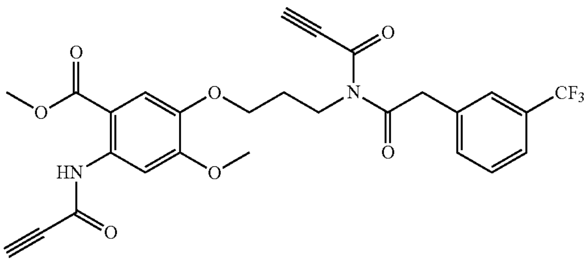 [SMILES: C#CC(=O)Nc1cc(OC)c(OCCCN(C(=O)C#C)C(=O)Cc2cccc(C(F)(F)F)c2)cc1C(=O)OC]<br>58t | 58t: methyl 4-methoxy-2-propiolamido-5-(3-(N-(2-(3-(trifluoromethyl)phenyl)acetyl) propiolamido)propoxy)benzoate; | R1 = CH3—O—CO—<br>R2 = —$(CH_2)_3$—N—(CO—CCH)—CO—CH2-phenyl-(3-trifluoromethyl)<br>R3 = —CH3;<br>R4 = H<br>R5 = —NH—CO—CCH<br>X1 = O; X2 = O |
| 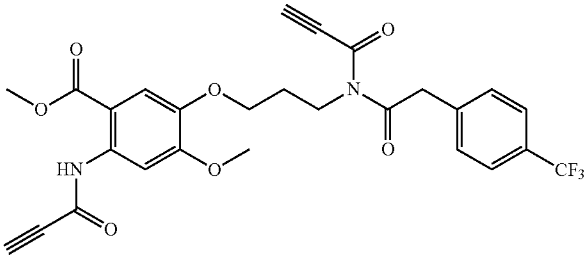 [SMILES: C#CC(=O)Nc1cc(OC)c(OCCCN(C(=O)C#C)C(=O)Cc2ccc(C(F)(F)F)cc2)cc1C(=O)OC]<br>58u | 58u: methyl 4-methoxy-2-propiolamido-5-(3-(N-(2-(4-(trifluoromethyl)phenyl)acetyl) propiolamido)propoxy)benzoate; | R1 = CH3—O—CO—<br>R2 = —$(CH_2)_3$—N—(CO—CCH)—CO—CH2-phenyl-(4-trifluoromethyl)<br>R3 = —CH3;<br>R4 = H<br>R5 = —NH—CO—CCH<br>X1 = O; X2 = O |
| 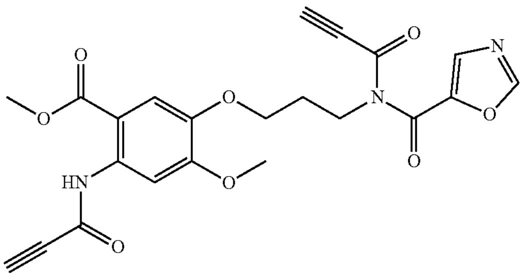 [SMILES: C#CC(=O)Nc1cc(OC)c(OCCCN(C(=O)C#C)C(=O)c2cnco2)cc1C(=O)OC]<br>58v | 58v: methyl 4-methoxy-2-propiolamido-5-(3-(N-propioloyloxazole-5-carboxamido)propoxy)benzoate; | R1 = CH3—O—CO—<br>R2 = —$(CH_2)_3$—N—(CO—CCH)—CO-oxazole)<br>R3 = —CH3;<br>R4 = H<br>R5 = —NH—CO—CCH<br>X1 = O; X2 = O |
| 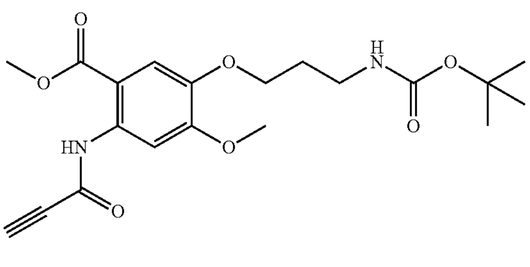 [SMILES: C#CC(=O)Nc1cc(OC)c(OCCCNC(=O)OC(C)(C)C)cc1C(=O)OC]<br>61 | 61: methyl 5-(3-((tert-butoxycarbonyl)amino)propoxy)-4-methoxy-2-propiolamidobenzoate; | R1 = CH3—O—CO—<br>R2 = —$(CH_2)_3$—NH—CO—O—C-trimethyl)<br>R3 = —CH3;<br>R4 = H<br>R5 = —NH—CO—CCH<br>X1 = O; X2 = O |

TABLE 6-continued

| | | |
|---|---|---|
| 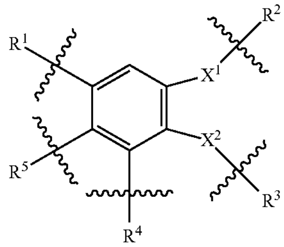 | | (I) |
| 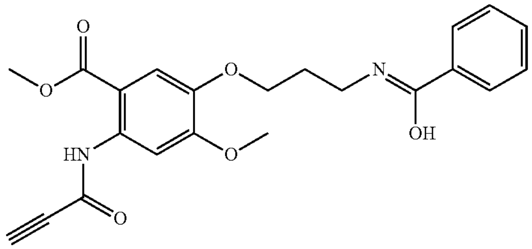 [SMILES: C#CC(=O)Nc1cc(OC)c(OCCC/N=C(\O)c2ccccc2)cc1C(=O)OC] 66 | 66: (Z)-N-(3-(2-methoxy-5-(methoxycarbonyl)-4-propiolamidophenoxy)propyl) benzimidic acid; | R1 = CH3—O—CO—<br>R2 = —$(CH_2)_3$—N═C—OH—phenyl<br>R3 = —CH3;<br>R4 = H<br>R5 = —NH—CO—CCH<br>X1 = O; X2 = O |
| 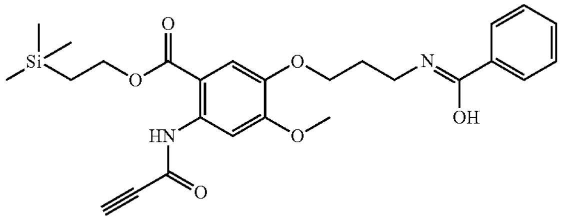 [SMILES: C#CC(=O)Nc1cc(OC)c(OCCC/N=C(\O)c2ccccc2)cc1C(=O)OCC[Si](C)(C)C] 70 | 70: (Z)-N-(3-(2-methoxy-4-propiolamido-5-((2-(trimethylsilyl)ethoxy)carbonyl) phenoxy)propyl)benzimidic acid; | R1 = $(CH_3)_3$—Si—O—CO—<br>R2 = —$(CH_2)_3$—N═C—OH—phenyl<br>R3 = —CH3;<br>R4 = H<br>R5 = —NH—CO—CCH<br>X1 = O; X2 = O |
| 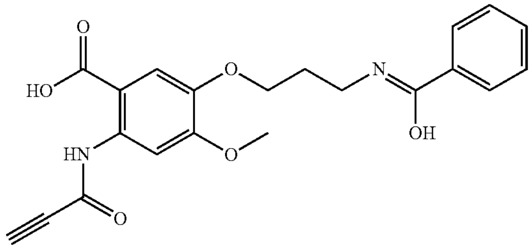 [SMILES: C#CC(=O)Nc1cc(OC)c(OCCC/N=C(\O)c2ccccc2)cc1C(=O)O] 71 | 71: (2)-5-(3-((hydroxy(phenyl)methylene) amino)propoxy)-4-methoxy-2-propiolamidobenzoic acid; | R1 = HO—CO—<br>R2 = —$(CH_2)_3$—N═C—OH—phenyl<br>R3 = —CH3;<br>R4 = H<br>R5 = —NH—CO—CCH<br>X1 = O; X2 = O |

All references cited and discussed in this specification are incorporated herein by reference in their entireties and to the same extent as it each reference as individually incorporated by reference.

What is claimed is:

1. A protein disulfide-isomerase A4 (PDIA4) inhibitor or a PDIA4 inhibitor anti-diabetic drug or an insulin-secretion augmenting agent which is a PDIA4 inhibitor, being selected from the group consisting of:

4

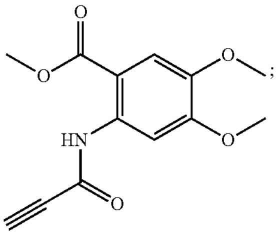 ;

-continued
7
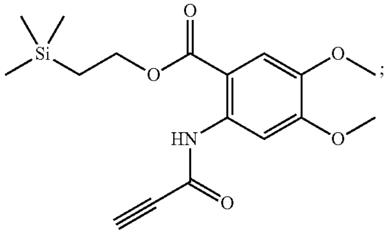
10
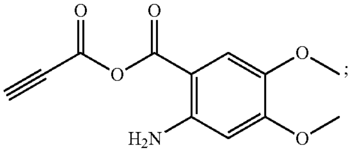
14
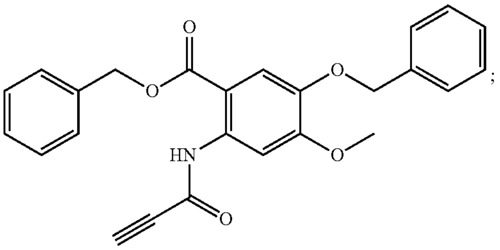
16
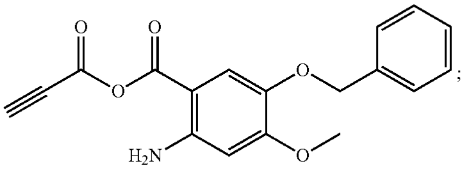
20
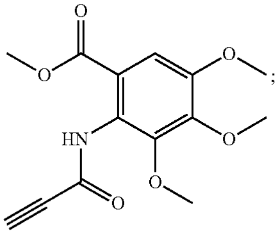
22
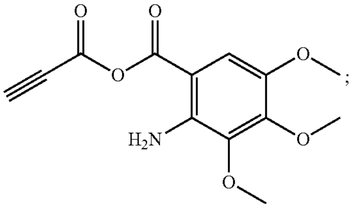
40
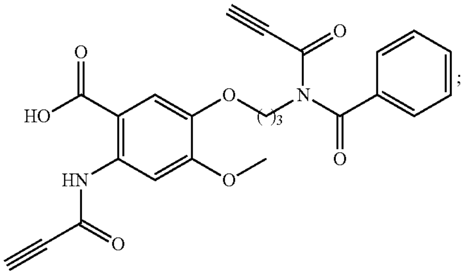
-continued
45
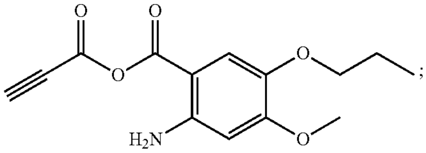
50a
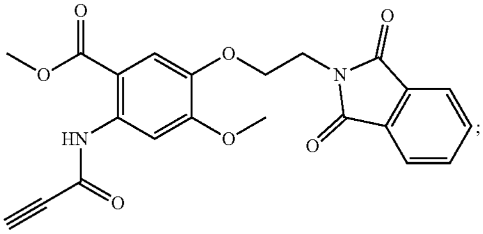
50b
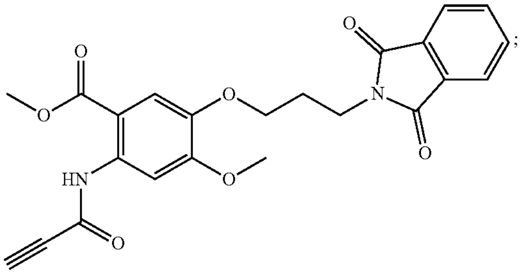
50c
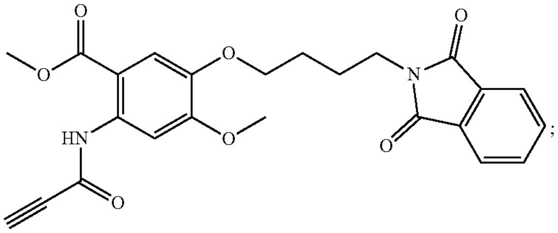
54
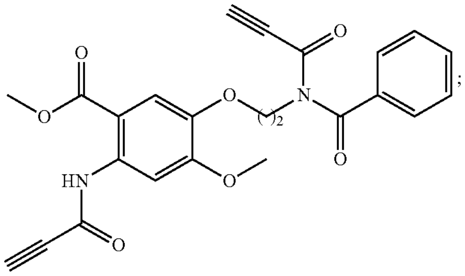
58a
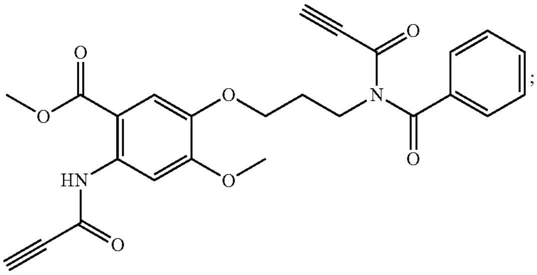

-continued
58b
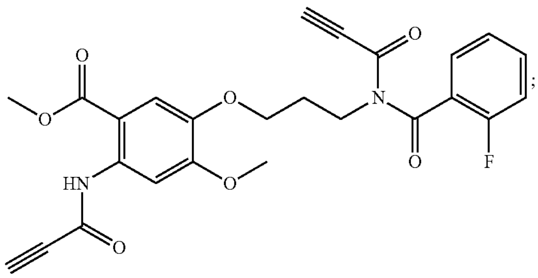
58c
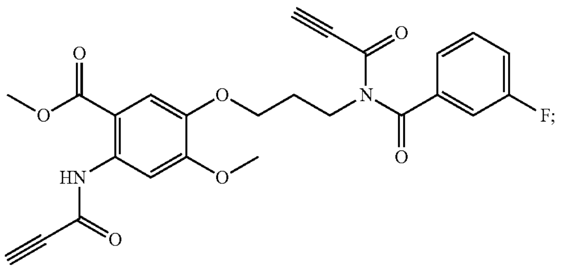
58d
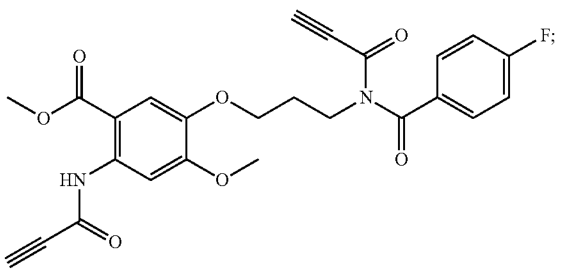
58e
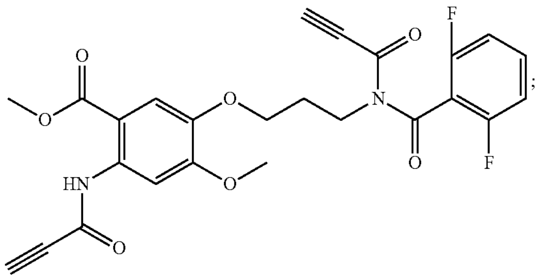
58f
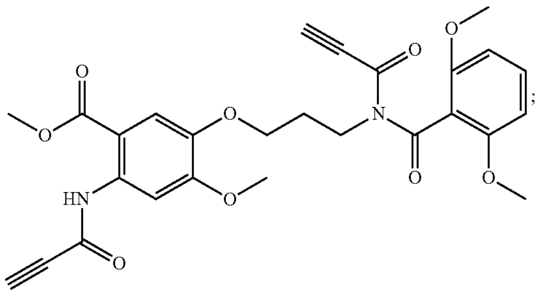
-continued
58g
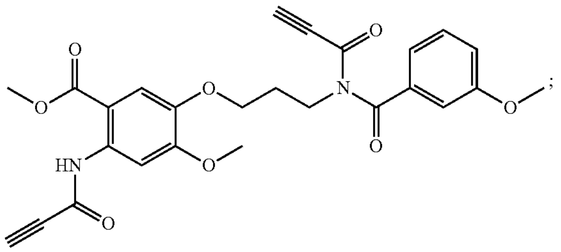
58h
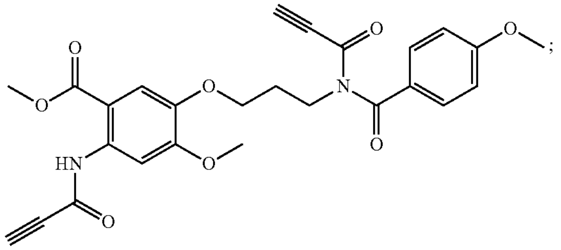
58i
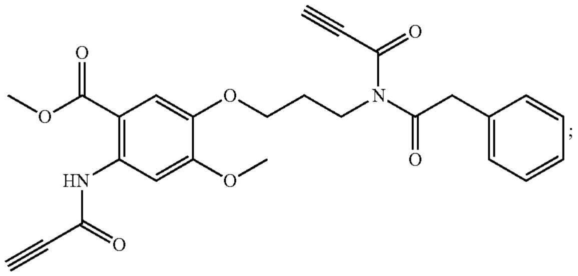
58j
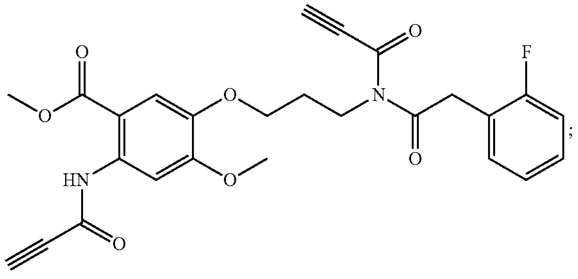
58k
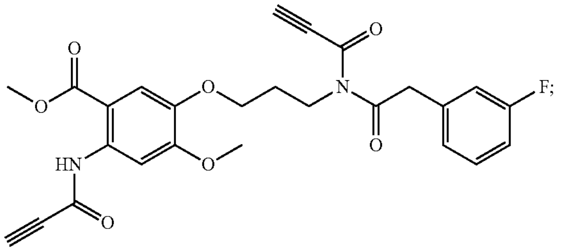

-continued
58l
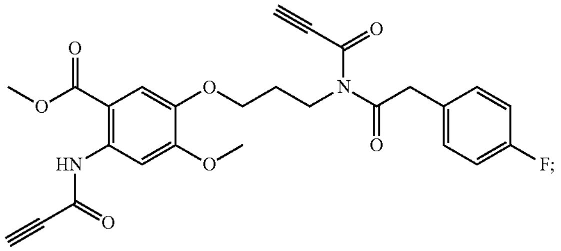
58m
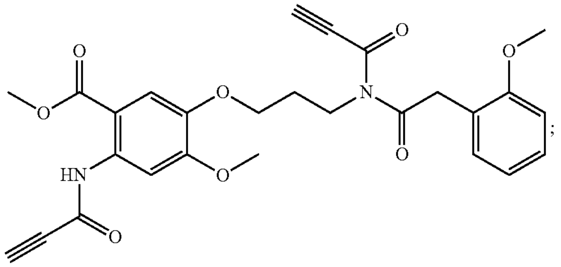
58n
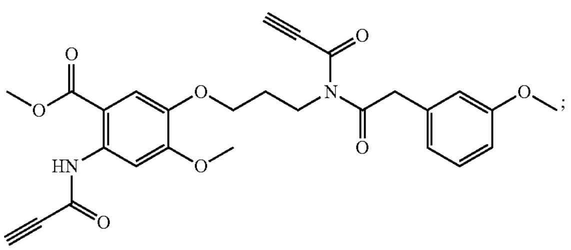
58o
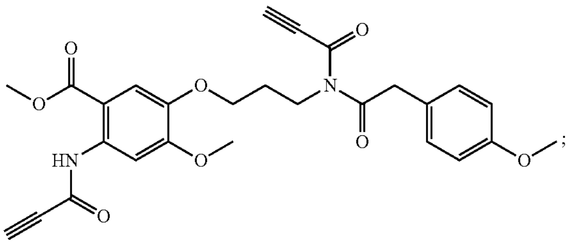
58p
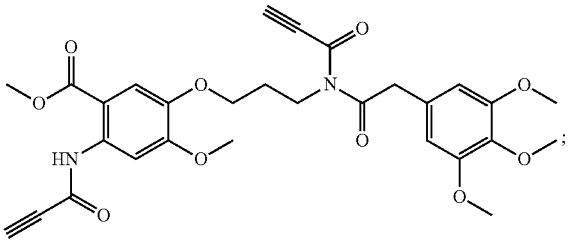
-continued
58q
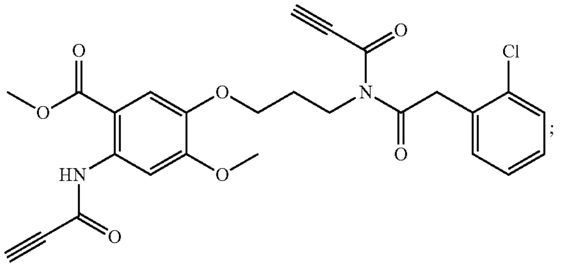
58r
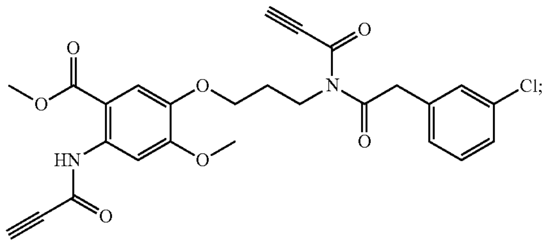
58s
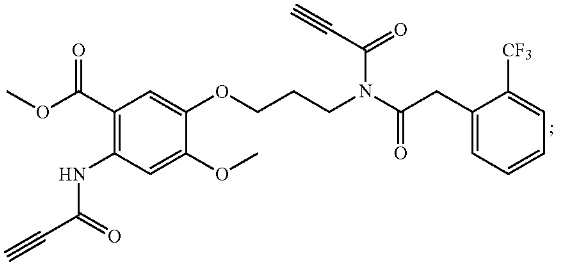
58t
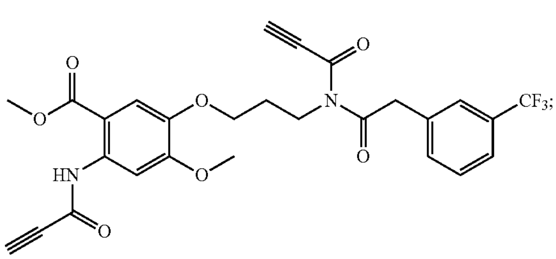
58u
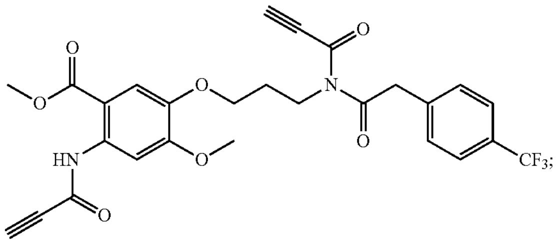

-continued
58v
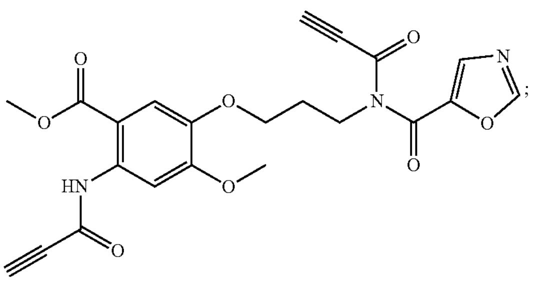
61
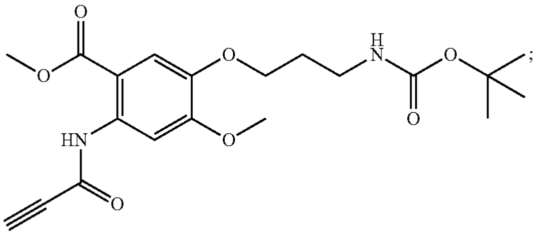
66
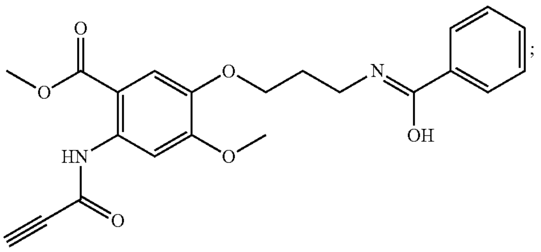
70
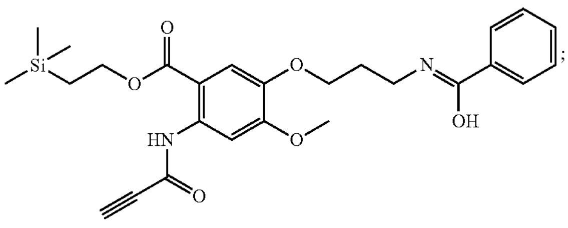
71
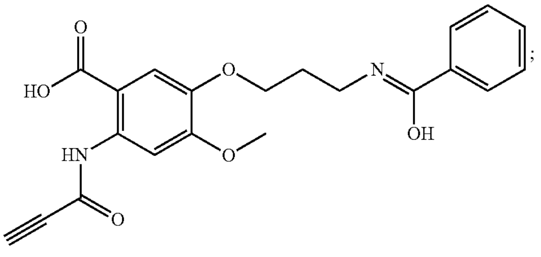
and pharmaceutically acceptable salts thereof.
2. A PDIA4 inhibitor-containing pharmaceutical composition, comprising:
(i) a PDIA4 inhibitor selected from the group consisting of:
4
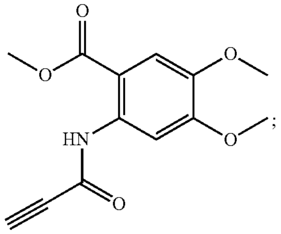
7
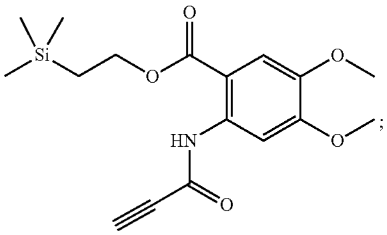
8
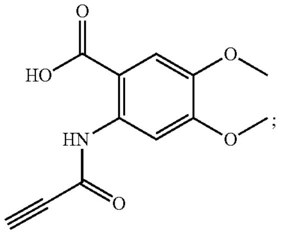
10
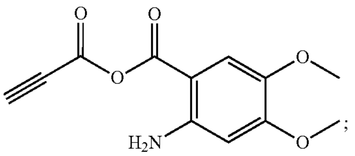
14
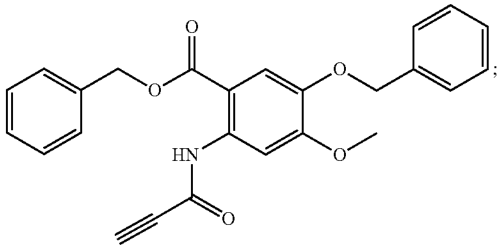
16
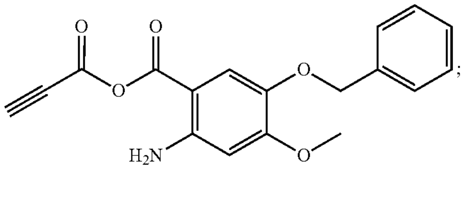
20
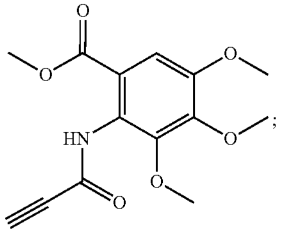

-continued
22
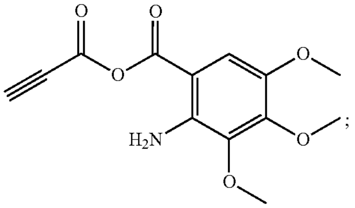
40
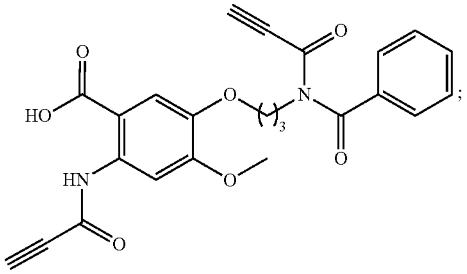
45
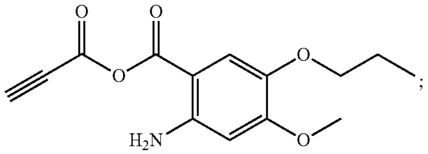
50a
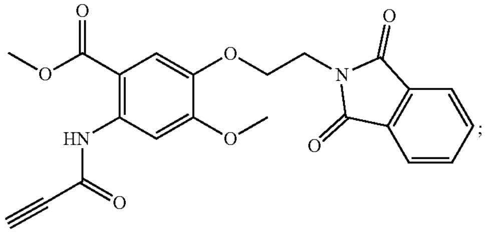
50b
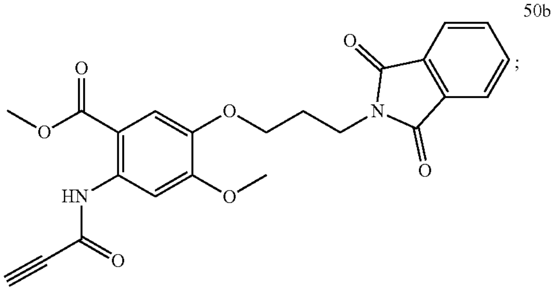
50c
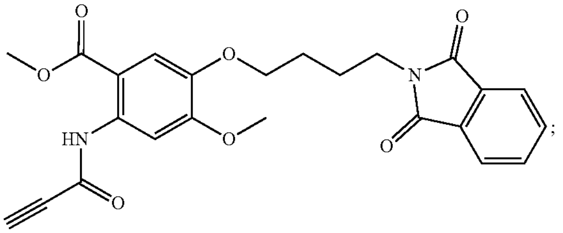
-continued
54
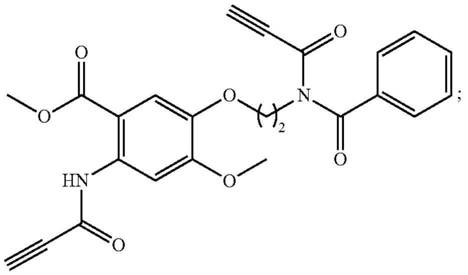
58a
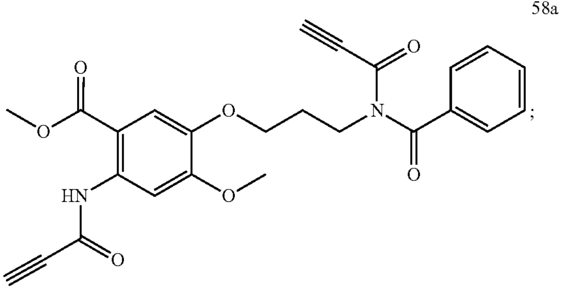
58b
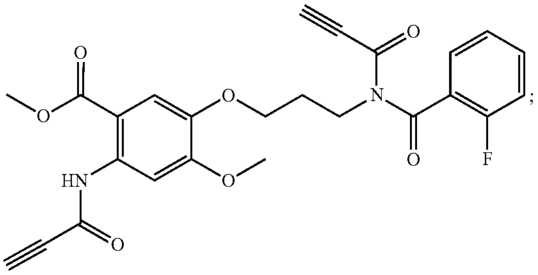
58c
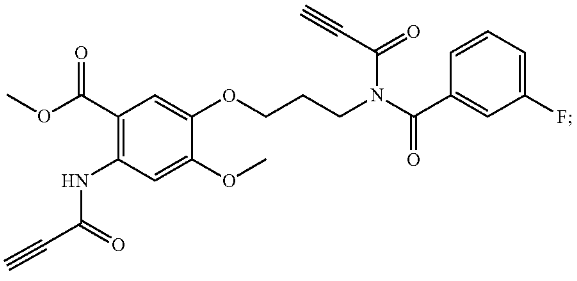
58d
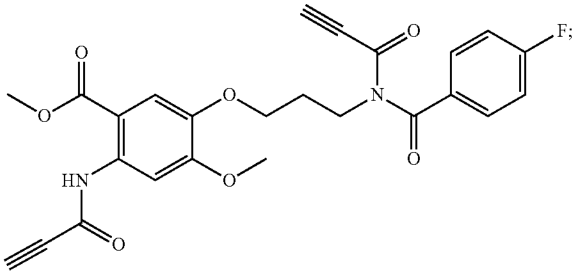

-continued
58e
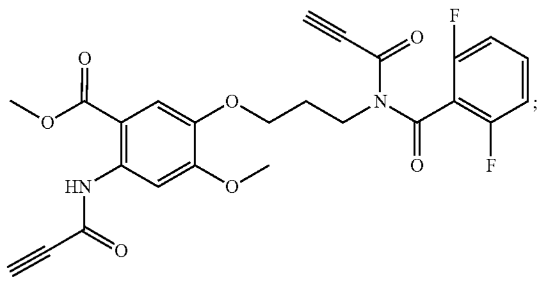
58f
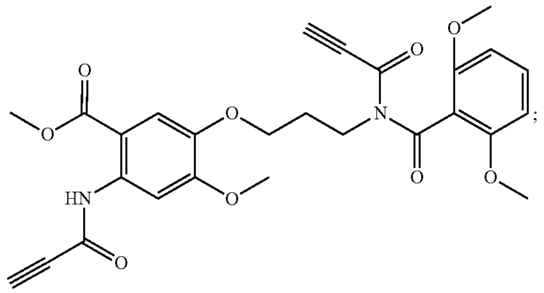
58g
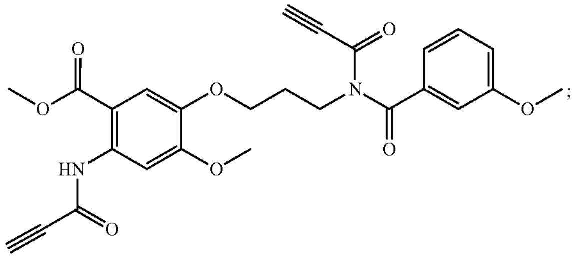
58h
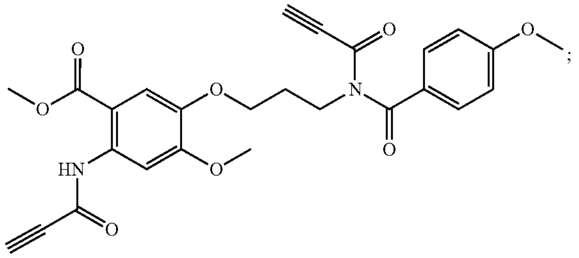
58i
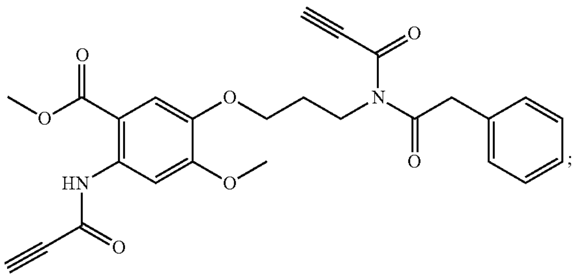
-continued
58j
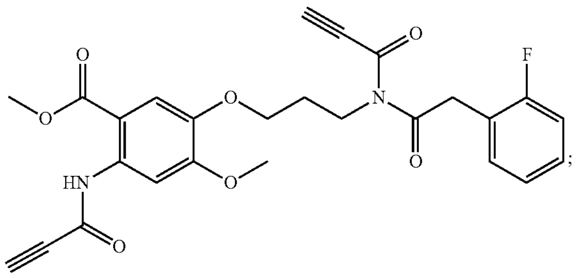
58k
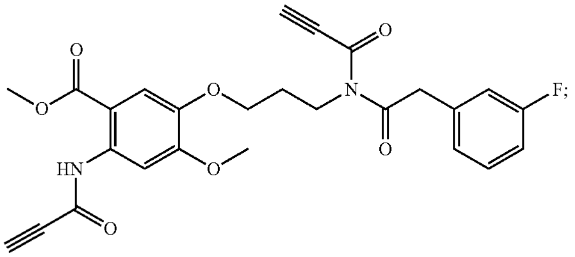
58l
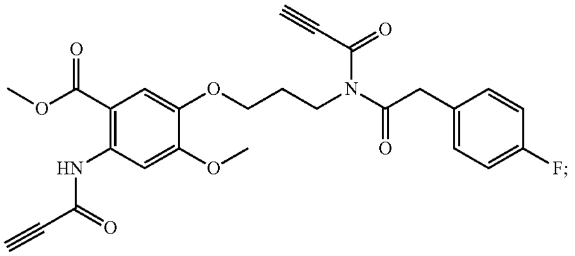
58m
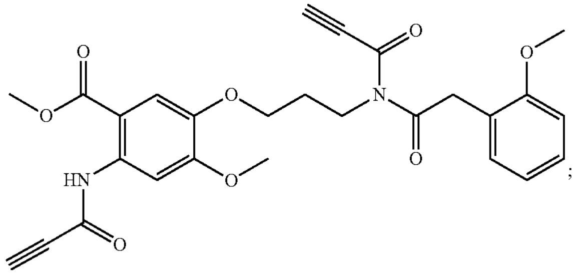
58n
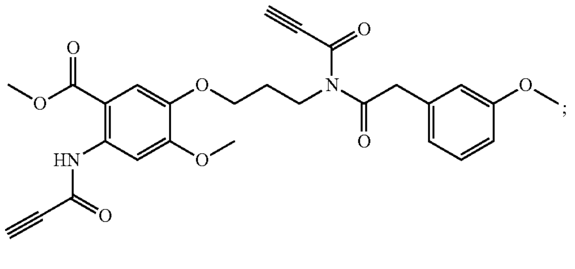

-continued
58o
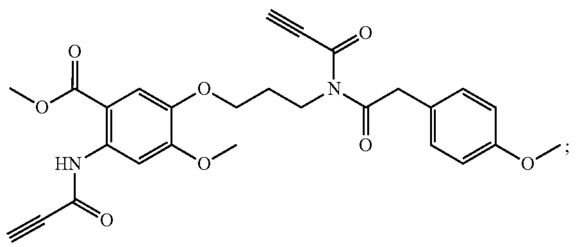
58p
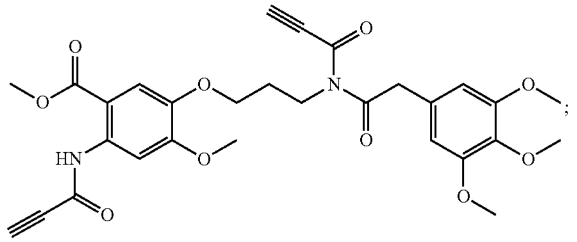
58q
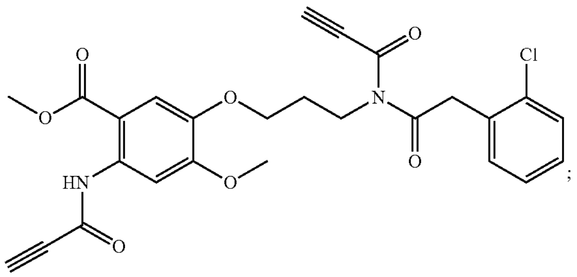
58r
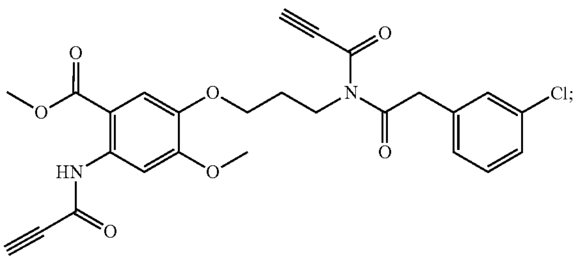
58s
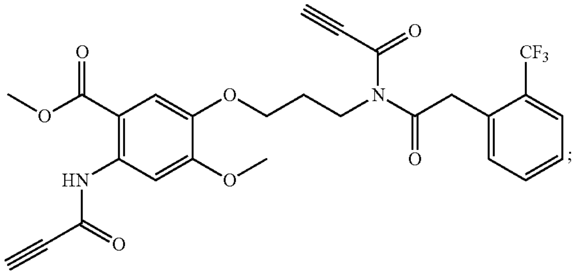
-continued
58t
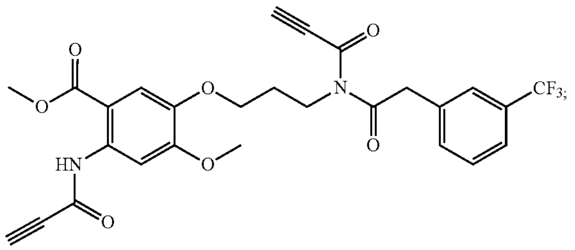
58u
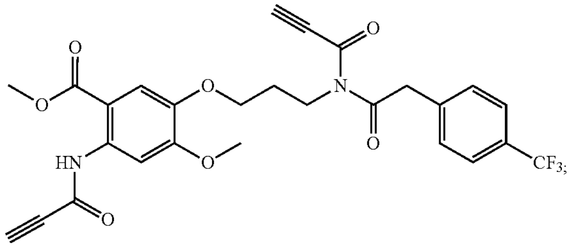
58v
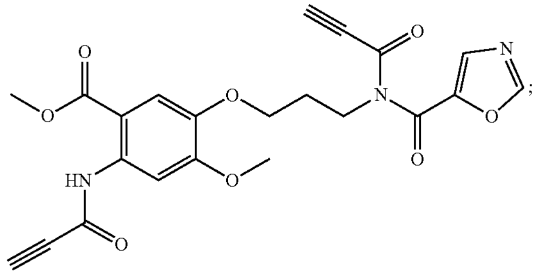
61
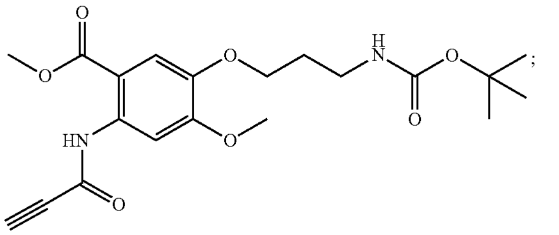
66
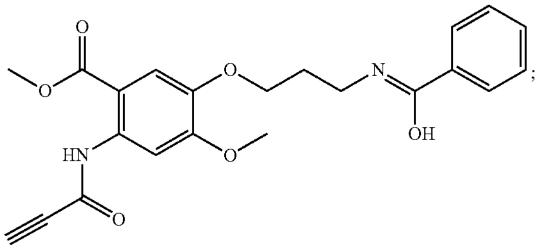
70
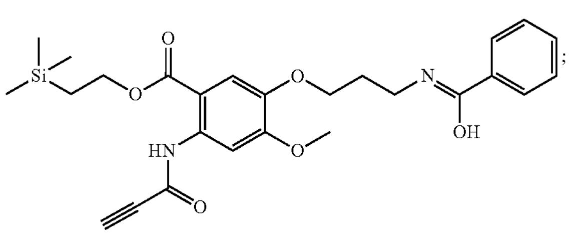

-continued

71

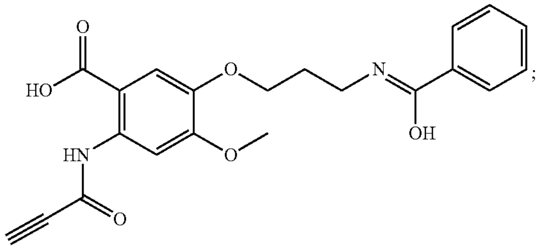

and pharmaceutically acceptable salts thereof; and (ii) a pharmaceutically acceptable carrier or excipient.

3. The PDIA4 inhibitor-containing pharmaceutical composition of claim 2, wherein the PDIA4 inhibitor is selected from the group consisting of:

8

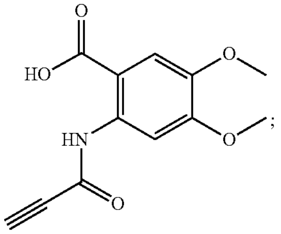

58v

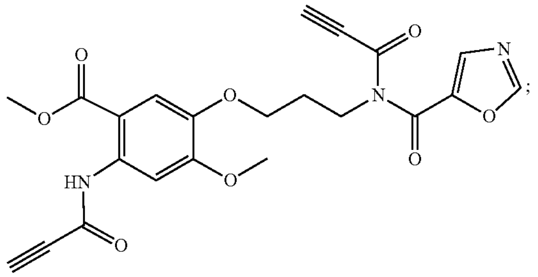

58t

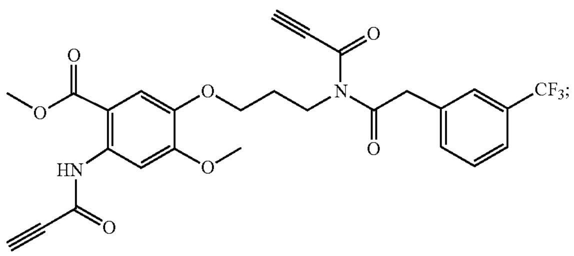

58s

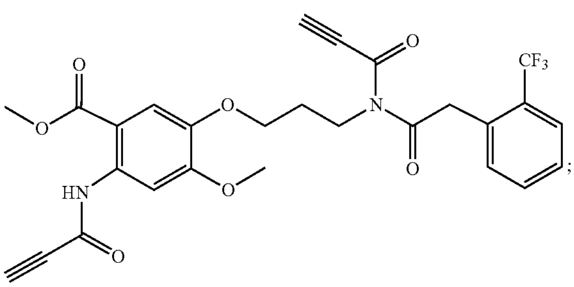

and pharmaceutically acceptable salts thereof.

4. The PDIA4 inhibitor-containing pharmaceutical composition of claim 3, wherein the PDIA4 inhibitor is

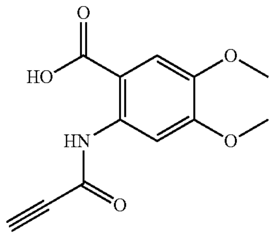 [SMILES: C#CC(=O)Nc1cc(OC)c(OC)cc1C(=O)O]

8, or a pharmaceutically acceptable salt thereof.

5. The PDIA4 inhibitor-containing pharmaceutical composition of claim 3, further comprising metformin.

6. The PDIA4 inhibitor-containing pharmaceutical composition of 5, wherein the PDIA4 inhibitor is selected from

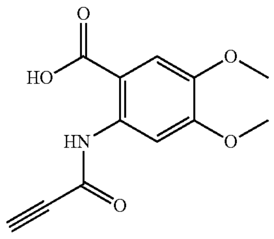 [SMILES: C#CC(=O)Nc1cc(OC)c(OC)cc1C(=O)O]

8 or a pharmaceutically acceptable salt thereof.

7. The PDIA4 inhibitor-containing pharmaceutical composition of claim 3, wherein the PDIA4 inhibitor is selected from

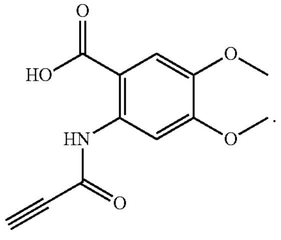 [SMILES: C#CC(=O)Nc1cc(OC)c(OC)cc1C(=O)O]

8.

8. A PDIA4 inhibitor-containing pharmaceutical composition, comprising:

(i) a PDIA4 inhibitor selected from the group consisting of:

4

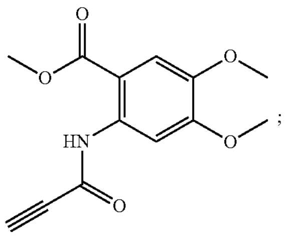

-continued
7
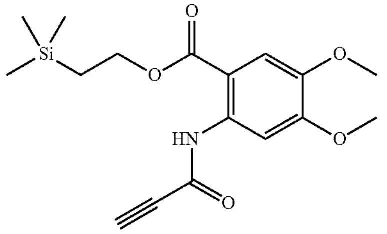
;
8
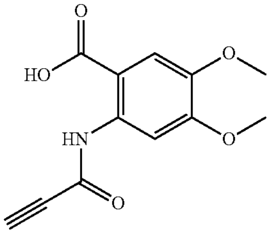 [SMILES: C#CC(=O)Nc1cc(OC)c(OC)cc1C(=O)O]
;
10
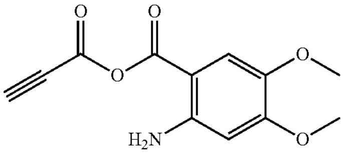
;
14
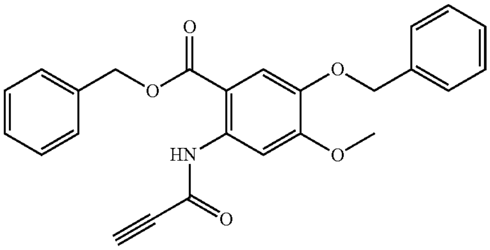
;
16
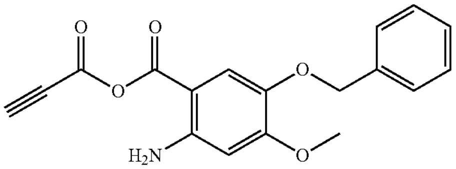
;
20
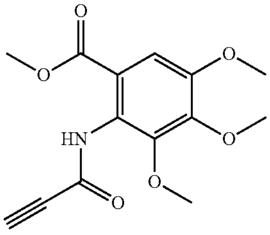
;
22
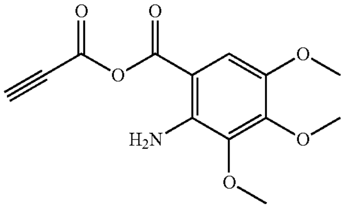
;
-continued
40
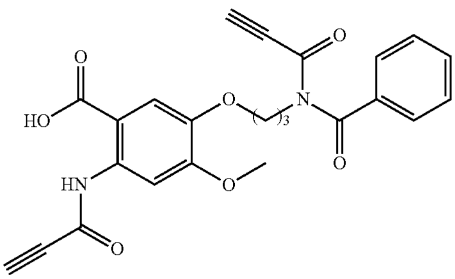
;
45
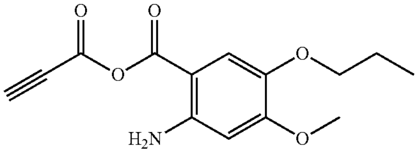
;
50a
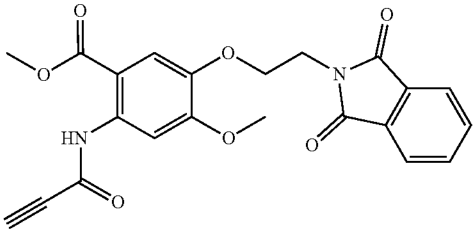
;
50b
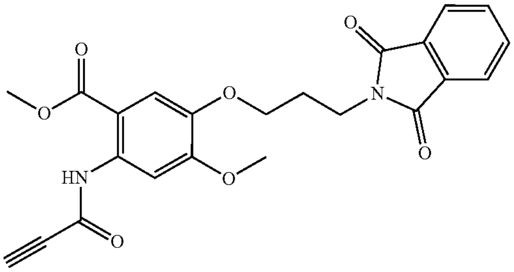
;
50c
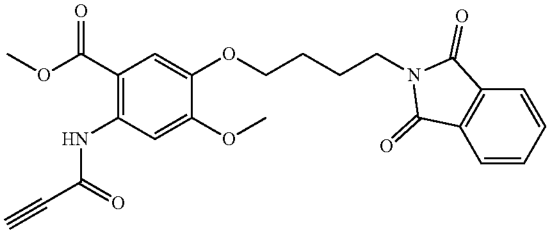
;
54
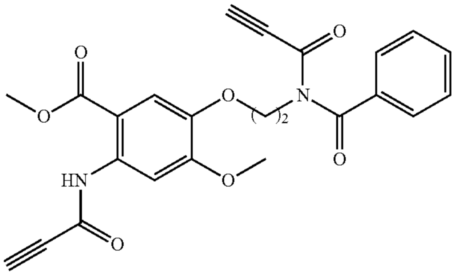

-continued
58a
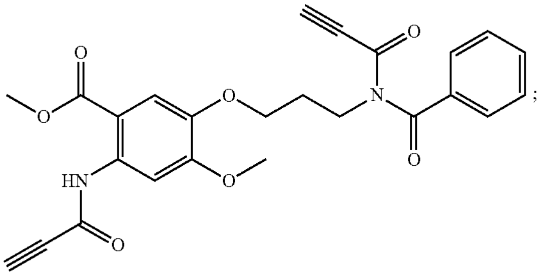
58b
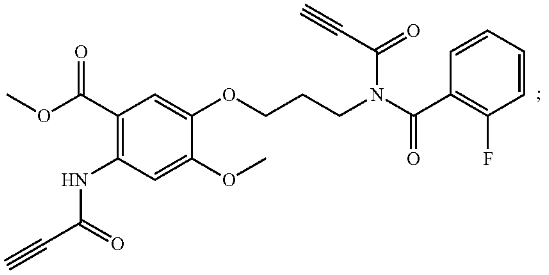
58c
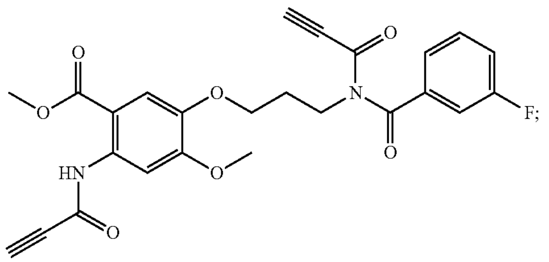
58d
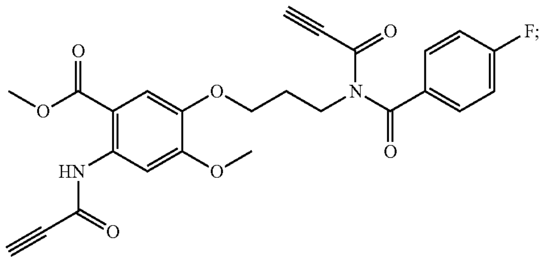
58e
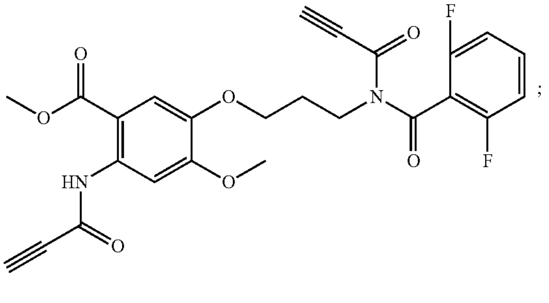
-continued
58f
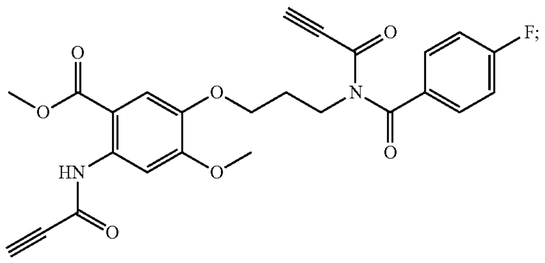
58g
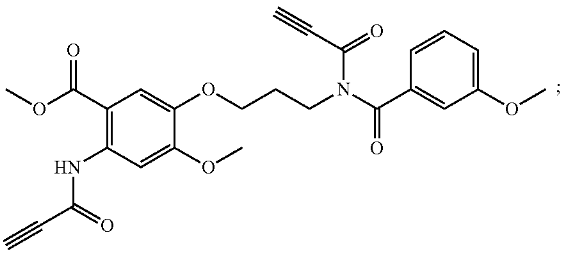
58h
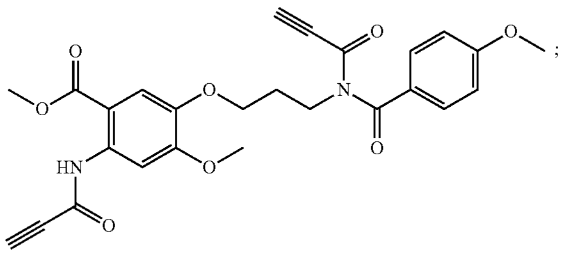
58i
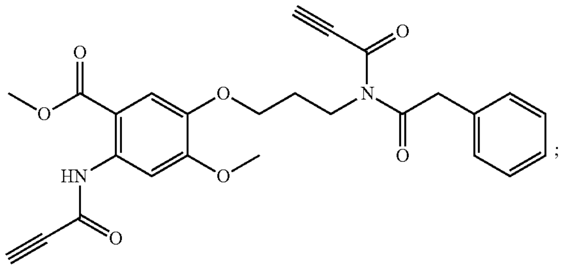
58j
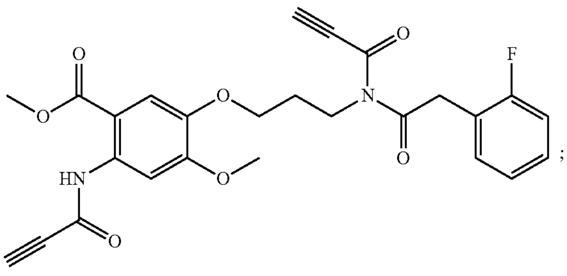

-continued
58k
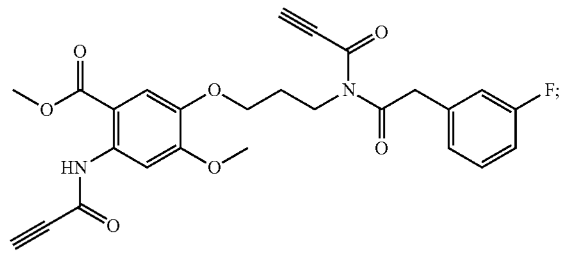
58l
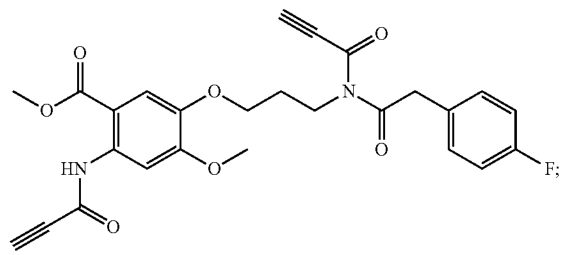
58m
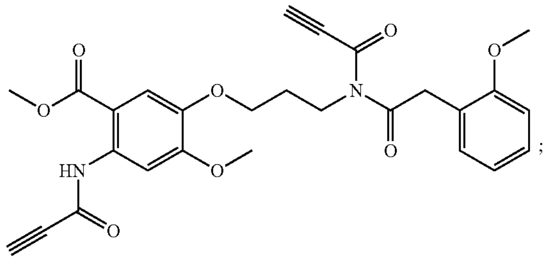
58n
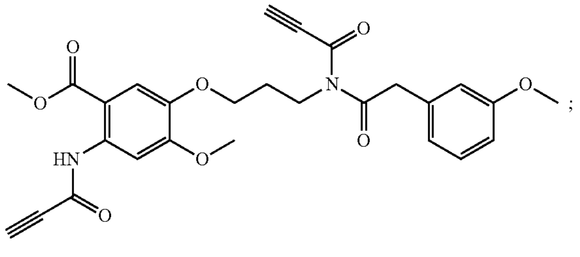
58o
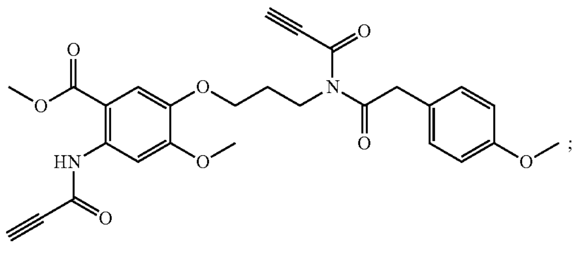
-continued
58p
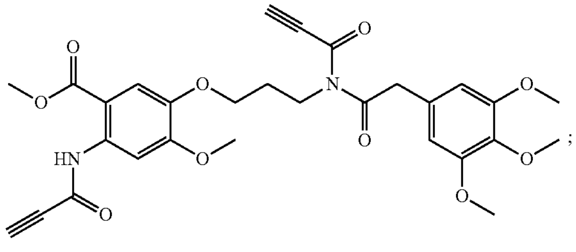
58q
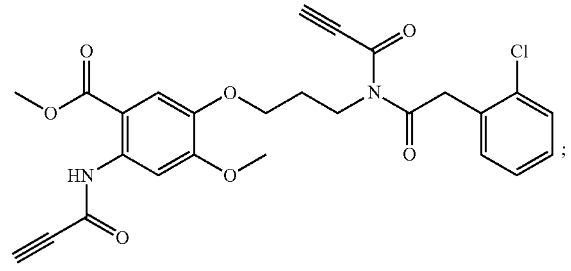
58r
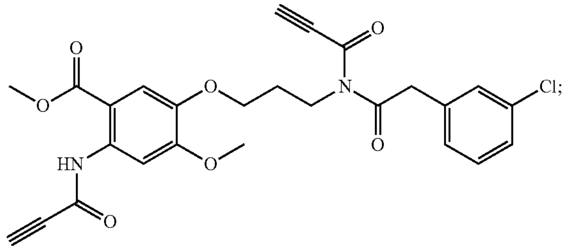
58s
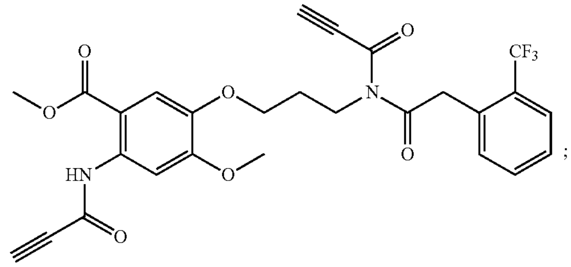
58t
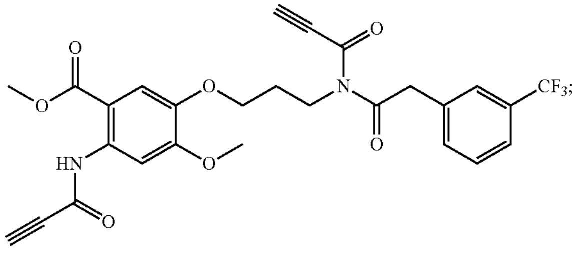

-continued

58u

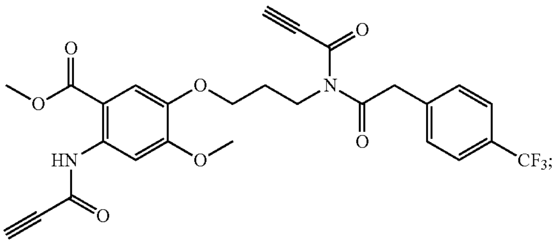

58v

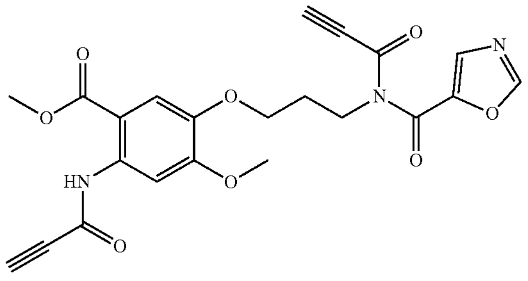
;

61

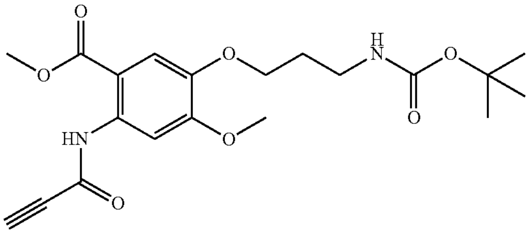
;

66

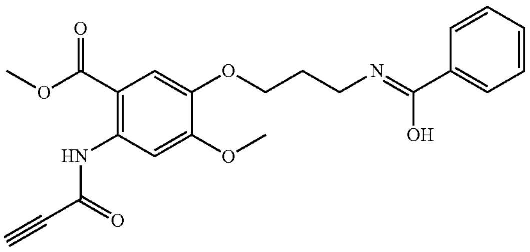
;

70

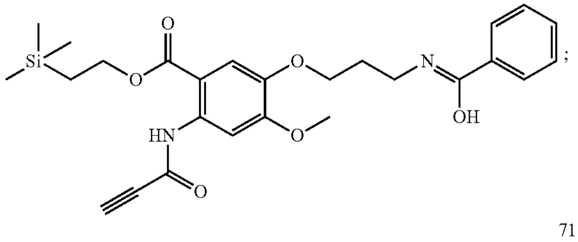
;

71

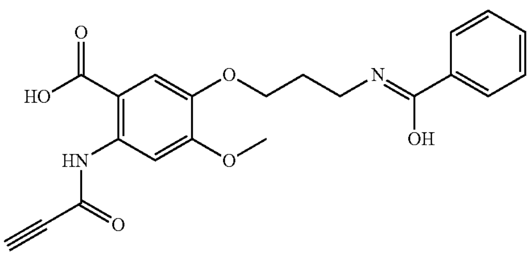
;

and pharmaceutically acceptable salts thereof, and
(ii) metformin.

9. The PDIA4 inhibitor-containing pharmaceutical composition of claim 8, wherein the PDIA4 inhibitor is selected from

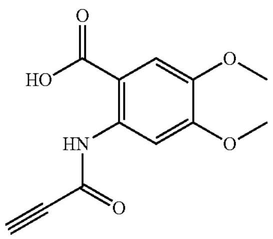 [SMILES: C#CC(=O)Nc1cc(OC)c(OC)cc1C(=O)O]

8 or a pharmaceutically acceptable salt thereof.

10. A method of augmenting insulin secretion from pancreatic β-cells and treating diabetes, comprising:

administering to a subject in need thereof a therapeutically effective amount of the PDIA4 inhibitor-containing pharmaceutical composition of claim 2.

11. A method of augmenting insulin secretion from pancreatic β-cells and/or treating diabetes, comprising:

administering to a subject in need thereof a therapeutically effective amount of the PDIA4 inhibitor-containing pharmaceutical composition of claim 3.

12. A method of augmenting insulin secretion from pancreatic β-cells, treating diabetes and/or reversing and returning blood glucose concentration to a normal level, comprising:

administering to a subject in need thereof a therapeutically effective amount of the PDIA4 inhibitor-containing pharmaceutical composition of claim 5.

13. The method of claim 12, wherein the PDIA4 inhibitor is selected from

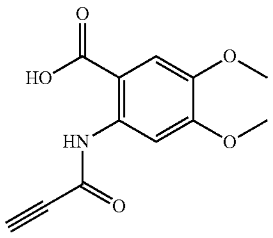 [SMILES: C#CC(=O)Nc1cc(OC)c(OC)cc1C(=O)O]

8 or a pharmaceutically acceptable salt thereof.

14. The method of claim 10, wherein the PDIA4 inhibitor is selected from

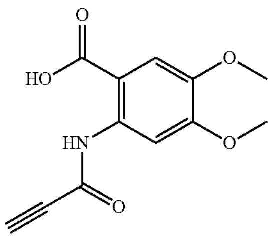 [SMILES: C#CC(=O)Nc1cc(OC)c(OC)cc1C(=O)O]

8 or a pharmaceutically acceptable salt thereof.

15. The method of claim 11, wherein the PDIA4 inhibitor is selected from

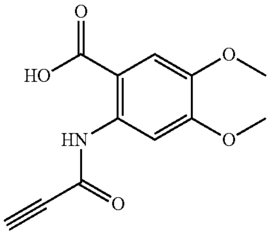 [SMILES: C#CC(=O)Nc1cc(OC)c(OC)cc1C(=O)O]

8.

16. The method of claim 12, wherein the PDIA4 inhibitor is selected from

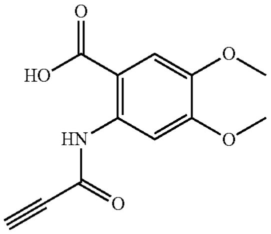 [SMILES: C#CC(=O)Nc1cc(OC)c(OC)cc1C(=O)O]

8 or a pharmaceutically acceptable salt thereof.

17. The method of claim 13, wherein the PDIA4 inhibitor is selected from

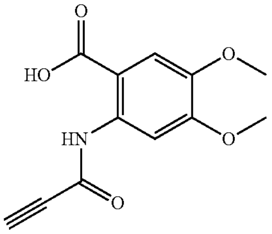

8 or a pharmaceutically acceptable salt thereof.

18. A method of inhibiting PDIA4 activity, said method comprising:

causing the PDIA4 inhibitor-containing pharmaceutical composition of claim 2 to be in contact with PDIA4 and thereby inhibiting the PDIA4 activity.

* * * * *